US012578329B2

(12) United States Patent
Ohmuro

(10) Patent No.: US 12,578,329 B2
(45) Date of Patent: * Mar. 17, 2026

(54) REAGENT KIT CONTAINING POLYPEPTIDE FOR USE IN DETECTION OF INTERMOLECULAR INTERACTIONS

(71) Applicant: SHIMADZU CORPORATION, Kyoto (JP)

(72) Inventor: Yuki Ohmuro, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/748,727

(22) Filed: May 19, 2022

(65) Prior Publication Data

US 2022/0373540 A1 Nov. 24, 2022

(30) Foreign Application Priority Data

May 19, 2021 (JP) ................................. 2021-084687

(51) Int. Cl.
| | |
|---|---|
| G01N 33/535 | (2006.01) |
| C07K 19/00 | (2006.01) |
| C12N 5/10 | (2006.01) |
| C12N 9/02 | (2006.01) |
| C12N 15/09 | (2006.01) |
| C12Q 1/26 | (2006.01) |
| G01N 21/76 | (2006.01) |
| G01N 33/543 | (2006.01) |

(52) U.S. Cl.
CPC ........... *G01N 33/535* (2013.01); *C07K 19/00* (2013.01); *C12N 5/10* (2013.01); *C12N 9/0069* (2013.01); *C12N 15/09* (2013.01); *C12Q 1/26* (2013.01); *G01N 21/763* (2013.01); *G01N 33/543* (2013.01); *C07K 2319/01* (2013.01)

(58) Field of Classification Search
CPC .. G01N 33/535; G01N 21/763; G01N 33/543; C07K 19/00; C07K 2319/01; C12N 5/10; C12N 9/0069; C12N 15/09; C12Q 1/26
See application file for complete search history.

(56) References Cited

U.S. PATENT DOCUMENTS

| | | | |
|---|---|---|---|
| 10,214,766 B2 | 2/2019 | Kim et al. | |
| 10,533,231 B2 | 1/2020 | Kim et al. | |
| 2007/0275428 A1* | 11/2007 | Gambhir .................. | C12Q 1/66 |
| | | | 435/8 |
| 2014/0242574 A1 | 8/2014 | Inouye et al. | |
| 2015/0284813 A1 | 10/2015 | Kim et al. | |
| 2016/0281129 A1 | 9/2016 | Kim et al. | |
| 2018/0265850 A1 | 9/2018 | Kim | |

FOREIGN PATENT DOCUMENTS

| | | |
|---|---|---|
| JP | 3048466 | 6/2000 |
| JP | 2013-544100 | 12/2013 |
| JP | 2014-100137 | 6/2014 |
| JP | 2018-126127 | 8/2018 |
| JP | 2018-126128 | 8/2018 |
| WO | 2012/071631 | 6/2012 |
| WO | 2014/065047 | 5/2014 |
| WO | 2017/057752 | 4/2017 |

OTHER PUBLICATIONS

Ahern, H. (1995). Biochemical, reagent kits offer scientists good return on investment. Scientist, 9(15), 20. (Year: 1995).*
Kim, S. B., Takenaka, Y., & Torimura, M. (2011). A bioluminescent probe for salivary cortisol. Bioconjugate Chemistry, 22(9), 1835-1841. (Year: 2011).*
Takenaka, Y., Yamaguchi, A., Tsuruoka, N., Torimura, M., Gojobori, T., & Shigeri, Y. (2012). Evolution of bioluminescence in marine planktonic copepods. Molecular biology and evolution, 29(6), 1669-1681. (Year: 2012).*
Delroisse, J., Duchatelet, L., Flammang, P., & Mallefet, J. (2021). Leaving the dark side? Insights into the evolution of luciferases. Frontiers in Marine Science, 8, 673620. (Year: 2021).*
Hunt, E., Moutsiopoulou, A., Ioannou, S. et al. Truncated Variants of Gaussia Luciferase with Tyrosine Linker for Site-Specific Bioconjugate Applications. Sci Rep 6, 26814 (2016). https://doi.org/10.1038/srep26814 (Year: 2016).*
Office Action issued Feb. 9, 2023 in corresponding U.S. Appl. No. 17/550,495.
Office Action issued Nov. 25, 2022 in U.S. Appl. No. 17/550,495.
U.S. Appl. No. 17/550,495, filed Dec. 14, 2021 in the Name of Yuki Ohmuro.
Kim, S.B., et al., "Creation of Artificial Luciferases for Bioassays", Bioconjugate Chem. 2013, vol. 24, pp. 2067-2075.

(Continued)

*Primary Examiner* — Louise W Humphrey
*Assistant Examiner* — Kimberly Breen
(74) *Attorney, Agent, or Firm* — Wenderoth, Lind & Ponack, L.L.P.

(57) ABSTRACT

A reagent kit comprising a first polypeptide including a part in any one of amino acid sequences (A) to (C), and a second polypeptide including a part in any one of amino acid sequences (A) to (C), which are consistent of different sequences from a sequence of the first polypeptide;

(A) an amino acid sequence in SEQ ID NO: 1 with deletion of an amino acid sequence from position 1 to 69 and an amino acid sequence from position 204 to 221, (B) an amino acid sequence in SEQ ID NO: 1 with deletion of an amino acid sequence from position 1 to 69 and deletion or substitution of at least one of amino acid residues at positions 146 to 156, (C) the amino acid sequence (A) or (B) with further deletion of at least one of amino acid residues at positions 70 to 74.

4 Claims, 37 Drawing Sheets

Specification includes a Sequence Listing.

(56) References Cited

OTHER PUBLICATIONS

NanoBit® PPI Starter Systems <https://www.promega.jp/products/protein-interactions/live-cell-protein-interactions/nanobit-ppi-starter-systems/?catNum=N2014>*Japanese<https://www.promega.jp/en/products/protein-interactions/live-cell-protein-interactions/nanobit-ppi-starter-systems/?catNum=N2014&cs=y>, with English translation.

Remy, I., et al., "A highly sensitive protein-protein interaction assay based on *Gaussia* luciferase", Nature Methods vol. 3 No. 12, Dec. 2006, pp. 977-979.

Kricka, et al., "Chemiluminescent Methods for Detecting and Quantitating Enzyme Activity", Methods in Enzymology, vol. 305 (2000) pp. 370-390.

Hamilton, et al., "Clinical Evaluation of the ZstatFlu—II Test: a Chemiluminescent Rapid Diagnostic Test for Influenza Virus", Journal of Clinical Microbiology, vol. 40, No. 7, (2002), pp. 2331-2334.

Ho, et al., "Reporter Enzyme Inhibitor Study to Aid Assembly of Orthogonal Reporter Gene Assays", ACS Chem. Biol. (2013), vol. 8, pp. 1009-1017.

Auld, et al., "Characterization and Use of TurboLuc Luciferase as a Reporter for High-Throughput Assays", Biochemistry (2018), vol. 57, pp. 4700-4706.

Secreted Luciferase Reporter Assay—Takara Bio Inc. http://catalog.takara-bio.co.jp/product/basic_info.php?unitid=U100005159 with machine translation inserted in red font.

Hall, et al., "Engineered Luciferase Reporter from a Deep Sea Shrimp Utilizing a Novel Imidazopyrazinone Substrate", ACS Chem. Biol. (2012) vol. 7, pp. 1848-1857.

Kim, et al., "Fabrication of a New Lineage of Artificial Luciferases from Natural Luciferase Pools", ACS Comb. Sci. (2017), vol. 19, pp. 594-599.

Markova, et al., "Shining Light on the Secreted Luciferases of Marine Copepods: Current Knowledge and Applications", Photochemistry and Photobiology, (2019), vol. 95, pp. 705-721.

Hunt et al., "Truncated Variants of *Gaussia* Luciferase with Tyrosine Linker for Site-Specific Bioconjugate Applications", Scientific Reports 6:26814 DOI: 10.1038/srep26814 (2016), 11 pages.

Takenaka et al., "Two forms of secreted and thermostable luciferases from the marine copepod crustacean, *Metridia pacifica*", Gene (2008), 425 pp. 28-35.

Kim, S.B., et al., "Functional artificial luciferases as an optical readout for bioassays", Biochemical and Biophysical Research Communication 448 (2014) pp. 418-423.

Ooe, et al., "Properties of the enzyme luciferase", Kogaku to Seibutsu (Science and Organisms) vol. 52, No. 1, (2014) pp. 59-60, machine translation.

TurboLuc Luciferase One-Step Glow Assay Kit—Thermo Fisher Scientific. 2015. https://www.thermofisher.com/order/catalog/product/88263#/88263 ha.

Sung Bae Kim et al., Molecular Imaging of Retinoic Acids in Live Cells Using Single Chain Bioluminescence Probes, (Apr. 2019), ACS Comb. Sci, vol. 21, pp. 473 481.

Japanese Office Action issued Aug. 13, 2024, in corresponding Japanese Patent Application No. 2021-084687, with English translation.

Japanese Office Action issued Feb. 12, 2025 in corresponding Japanese Patent Application No. 2021-084687, with English translation.

Japanese Office Action issued Nov. 11, 2025 in corresponding Japanese Application No. 2021-199158, with English translation.

Office Action issued Jun. 24, 2025 in Japanese Patent Application No. 2021-199158, with English-language Translation.

* cited by examiner

Comparison of amino acid sequences of picALuc30 and picALuc16

```
                                                                    54
ALuc30 wt    1 HHHHHHHHDIVGVEGKFGTTDLETDLFTIVEDMNVISRDTDVDANRADRGRRGKLPGKKL
ALuc16 wt    1 PTENKDDIDIVGVEGKFGTTDLETDLFTIVEDMNVISRDTDVDANRADRGRRGKLPGKKL
                       *********************************************

122    128
ALuc30 wt   61 PLEVLKELEANAQKAGCTRGCLICLSHIKCTAKMKKWLPGRCESWEGDKETGQGGIGEAI
ALuc16 wt   61 PLEVLKELEANAQKAGCTRGCLICLSHIKCTAKMKKWLPGRCESWEGDKETGQGGIGEAI
               *********** * *********************************************

175
ALuc30 wt  121 VDIPEIPGFKELAPMEQFIAQVDLCADCTTGCLKGLANVKCSALLKKWLPSRCAGFADKI
ALuc16 wt  121 VDIPEIPGFKDLEPMEQFIAQVDLCVDCTTGCLKGLANVKCSDLLKKWLPSRCATFASKI
               ********** *  ***********  **************** ***********  *  *

193
ALuc30 wt  181 QAQVDTIKGAGGS
ALuc16 wt  181 QAQVDKIKGAGGS
               ***** *******
```

□ : picALuc sequence
96% identity (picALuc sequence)

FIG.6

Comparison of amino acid sequences of picALuc30 and picALuc48

FIG.7

Comparison of amino acid sequences of picALuc48 and picALuc16

```
ALuc48 wt    1 PTENKDDIDIVGVEGKFGTTDLETDLFTIVEDMNVISRDTDVDANRADRGRRQHGGLPGK  54
ALuc16 wt    1 PTENKDDIDIVGVEGKFGTTDLETDLFTIVEDMNVISRDTDVDANRADRGRRQK--LPGK  54
               ***********************************************************

ALuc48 wt   61 KMPLEVLLELEANAQRAGCTRGCLICLSKIKCTAKMKKWLPGRCESWAGDKETGQGGITE
ALuc16 wt   59 KLPLEVLKELEANAQKAGCTRGCLICLSHIKCTAKMKKWLPGRCESWEGDKETGQGGIG-
               * *****  *** **** *** ***** * ********** ** ********** ** *

ALuc48 wt  121 EETVDIPEIPGFKDLEPMEQFIAQVDLCVDCTTGGLKGLANVKCSDLLKKWLPSRCATFA 178
ALuc16 wt  118 EAIVDIPEIPGFKDLEPMEQFIAQVDLCVDCTTGGLKGLANVKCSDLLKKWLPSRCATFA 175
               * ***********************************************************

ALuc48 wt  181 SKIQAQVDKIKGAGGS 196
ALuc16 wt  178 SKIQAQVDKIKGAGGS 193
               ****************
```

□ : picALuc sequence

90% identity (picALuc sequence)

Error bar :± 1 SD(n=3)

Error bar :±1SD(n=3)

Error bar :±1SD(n=3)

Error bar : ± 1SD(n=3)

FIG.24

Error bar :±1SD(n=3)

FIG.26

FKBP-4-77aa
23-120aa-FRB

FKBP-23-120aa
4-22aa-FRB

FIG.37

SEQUENCE LISTING

```
<160> NUMBER OF SEQ ID NOS: 91

<210> SEQ ID NO 1
<211> LENGTH: 221
<212> TYPE: PRT
<213> ORGANISM: Artificial Sequence
<220> FEATURE:
<223> OTHER INFORMATION: ALucCM (common artificial luciferase)
<220> FEATURE:
<221> NAME/KEY: misc_feature
<222> LOCATION: (3)..(7)
<223> OTHER INFORMATION: Xaa(3)=any a.a. Xaa(5)=hydrophilic a.a.
      Xaa(4,6,7)=aliphatic a.a.
<220> FEATURE:
<221> NAME/KEY: misc_feature
<222> LOCATION: (10)..(11)
<223> OTHER INFORMATION: Xaa(10,11)=aliphatic a.a.
<220> FEATURE:
```

-continued

```
<221> NAME/KEY: misc_feature
<222> LOCATION: (13)..(13)
<223> OTHER INFORMATION: Xaa(13)=hydrophobic a.a.
<220> FEATURE:
<221> NAME/KEY: misc_feature
<222> LOCATION: (15)..(16)
<223> OTHER INFORMATION: Xaa(16)=hydrophobic a.a. Xaa(15)=aliphatic a.a.
<220> FEATURE:
<221> NAME/KEY: misc_feature
<222> LOCATION: (20)..(29)
<223> OTHER INFORMATION: Xaa(20,21,24-29)=any a.a. Xaa(22,23)=any or no
      a.a.
<220> FEATURE:
<221> NAME/KEY: misc_feature
<222> LOCATION: (31)..(35)
<223> OTHER INFORMATION: Xaa(31,32,35)=any a.a. Xaa(33,34)=aliphatic
      a.a.
<220> FEATURE:
<221> NAME/KEY: misc_feature
<222> LOCATION: (37)..(37)
<223> OTHER INFORMATION: Xaa(37)=any a.a.
<220> FEATURE:
<221> NAME/KEY: misc_feature
<222> LOCATION: (39)..(41)
<223> OTHER INFORMATION: Xaa(39,40)=aliphatic or no a.a.
      Xaa(41)=aliphatic a.a.
<220> FEATURE:
<221> NAME/KEY: misc_feature
<222> LOCATION: (62)..(69)
<223> OTHER INFORMATION: Xaa(64-66,69)=any a.a. Xaa(67)=hydrophilic a.a.
      Xaa(63,68)=aliphatic a.a. Xaa(62)=negative a.a.
<220> FEATURE:
<221> NAME/KEY: misc_feature
<222> LOCATION: (72)..(78)
<223> OTHER INFORMATION: Xaa(76,77)=any or no a.a. Xaa(75)=hydrophilic
      a.a. Xaa(74)=aliphatic or no a.a. Xaa(78)=aliphatic a.a.
      Xaa(72,73)=positive or no a.a.
<220> FEATURE:
<221> NAME/KEY: misc_feature
<222> LOCATION: (83)..(83)
<223> OTHER INFORMATION: Xaa(83)=aliphatic a.a.
<220> FEATURE:
<221> NAME/KEY: misc_feature
<222> LOCATION: (85)..(86)
<223> OTHER INFORMATION: Xaa(85,86)=any a.a.
<220> FEATURE:
<221> NAME/KEY: misc_feature
<222> LOCATION: (89)..(90)
<223> OTHER INFORMATION: Xaa(89,90)=any a.a.
<220> FEATURE:
<221> NAME/KEY: misc_feature
<222> LOCATION: (97)..(97)
<223> OTHER INFORMATION: Xaa(97)=positive a.a.
<220> FEATURE:
<221> NAME/KEY: misc_feature
<222> LOCATION: (101)..(101)
<223> OTHER INFORMATION: Xaa(101)=hydrophilic a.a.
<220> FEATURE:
<221> NAME/KEY: misc_feature
<222> LOCATION: (110)..(110)
<223> OTHER INFORMATION: Xaa(110)=positive a.a.
<220> FEATURE:
<221> NAME/KEY: misc_feature
<222> LOCATION: (119)..(119)
<223> OTHER INFORMATION: Xaa(119)=hydrophilic a.a.
<220> FEATURE:
<221> NAME/KEY: misc_feature
<222> LOCATION: (129)..(129)
<223> OTHER INFORMATION: Xaa(129)=any a.a.
<220> FEATURE:
<221> NAME/KEY: misc_feature
<222> LOCATION: (137)..(137)
<223> OTHER INFORMATION: Xaa(137)=aliphatic a.a.
<220> FEATURE:
<221> NAME/KEY: misc_feature
<222> LOCATION: (140)..(144)
<223> OTHER INFORMATION: Xaa(140)=any or no a.a. Xaa(141-144)=any a.a.
<220> FEATURE:
<221> NAME/KEY: misc_feature
```

```
<222> LOCATION: (148)..(151)
<223> OTHER INFORMATION: Xaa(148-151)=any or no a.a.
<220> FEATURE:
<221> NAME/KEY: misc_feature
<222> LOCATION: (159)..(161)
<223> OTHER INFORMATION: Xaa(159,161)=any a.a. Xaa(160)=aliphatic a.a.
<220> FEATURE:
<221> NAME/KEY: misc_feature
<222> LOCATION: (174)..(174)
<223> OTHER INFORMATION: Xaa(174)=hydrophobic a.a.
<220> FEATURE:
<221> NAME/KEY: misc_feature
<222> LOCATION: (188)..(188)
<223> OTHER INFORMATION: Xaa(188)=any a.a.
<220> FEATURE:
<221> NAME/KEY: misc_feature
<222> LOCATION: (191)..(191)
<223> OTHER INFORMATION: Xaa(191)=any a.a.
<220> FEATURE:
<221> NAME/KEY: misc_feature
<222> LOCATION: (202)..(203)
<223> OTHER INFORMATION: Xaa(202)=any a.a. Xaa(203)=aliphatic a.a.
<220> FEATURE:
<221> NAME/KEY: misc_feature
<222> LOCATION: (206)..(206)
<223> OTHER INFORMATION: Xaa(206)=any a.a.
<220> FEATURE:
<221> NAME/KEY: misc_feature
<222> LOCATION: (211)..(211)
<223> OTHER INFORMATION: Xaa(211)=negative a.a.
<220> FEATURE:
<221> NAME/KEY: misc_feature
<222> LOCATION: (214)..(214)
<223> OTHER INFORMATION: Xaa(211)=hydrophilic a.a.
<220> FEATURE:
<221> NAME/KEY: misc_feature
<222> LOCATION: (218)..(218)
<223> OTHER INFORMATION: Xaa(218)=hydrophobic a.a.

<400> SEQUENCE: 1

Met Met Xaa Xaa Xaa Xaa Xaa Phe Ala Xaa Xaa Cys Xaa Ala Xaa Xaa
1               5                   10                  15

Gln Ala Asn Xaa Xaa Xaa Xaa Xaa Xaa Xaa Xaa Xaa Xaa Asp Xaa Xaa
                20                  25                  30

Xaa Xaa Xaa Gly Xaa Phe Xaa Xaa Xaa Asp Leu Glu Thr Asp Leu Phe
        35                  40                  45

Thr Ile Val Glu Asp Met Asn Val Ile Ser Arg Asp Thr Xaa Xaa Xaa
    50                  55                  60

Xaa Xaa Xaa Xaa Xaa Arg Gly Xaa Xaa Xaa Xaa Xaa Xaa Pro Gly
65                  70                  75                  80

Lys Lys Xaa Pro Xaa Xaa Val Leu Xaa Xaa Leu Glu Ala Asn Ala Gln
                85                  90                  95

Xaa Ala Gly Cys Xaa Arg Gly Cys Leu Ile Cys Leu Ser Xaa Ile Lys
            100                 105                 110

Cys Thr Ala Lys Met Lys Xaa Trp Leu Pro Gly Arg Cys Glu Ser Trp
        115                 120                 125

Xaa Gly Asp Lys Glu Thr Gly Gln Xaa Gly Ile Xaa Xaa Xaa Xaa Xaa
    130                 135                 140

Val Asp Ile Xaa Xaa Xaa Xaa Pro Glu Ile Pro Gly Phe Lys Xaa Xaa
145                 150                 155                 160

Xaa Pro Met Glu Gln Phe Ile Ala Gln Val Asp Leu Cys Xaa Asp Cys
            165                 170                 175

Thr Thr Gly Cys Leu Lys Gly Leu Ala Asn Val Xaa Cys Ser Xaa Leu
            180                 185                 190

Leu Lys Lys Trp Leu Pro Ser Arg Cys Xaa Xaa Phe Ala Xaa Lys Ile
        195                 200                 205
```

```
Gln Ala Xaa Val Asp Xaa Ile Lys Gly Xaa Gly Gly Ser
    210             215             220

<210> SEQ ID NO 2
<211> LENGTH: 8
<212> TYPE: PRT
<213> ORGANISM: Artificial Sequence
<220> FEATURE:
<223> OTHER INFORMATION: ALuc partial sequence

<400> SEQUENCE: 2

Pro Thr Glu Asn Lys Asp Asp Ile
1               5

<210> SEQ ID NO 3
<211> LENGTH: 8
<212> TYPE: PRT
<213> ORGANISM: Artificial Sequence
<220> FEATURE:
<223> OTHER INFORMATION: ALuc partial sequence

<400> SEQUENCE: 3

Ala Thr Ile Asn Glu Glu Asp Ile
1               5

<210> SEQ ID NO 4
<211> LENGTH: 10
<212> TYPE: PRT
<213> ORGANISM: Artificial Sequence
<220> FEATURE:
<223> OTHER INFORMATION: ALuc partial sequence

<400> SEQUENCE: 4

Ala Thr Ile Asn Glu Asn Phe Glu Asp Ile
1               5                   10

<210> SEQ ID NO 5
<211> LENGTH: 8
<212> TYPE: PRT
<213> ORGANISM: Artificial Sequence
<220> FEATURE:
<223> OTHER INFORMATION: ALuc partial sequence

<400> SEQUENCE: 5

His His His His His His His His
1               5

<210> SEQ ID NO 6
<211> LENGTH: 7
<212> TYPE: PRT
<213> ORGANISM: Artificial Sequence
<220> FEATURE:
<223> OTHER INFORMATION: ALuc partial sequence

<400> SEQUENCE: 6

Glu Lys Leu Ile Ser Glu Glu
1               5

<210> SEQ ID NO 7
<211> LENGTH: 8
<212> TYPE: PRT
<213> ORGANISM: Artificial Sequence
<220> FEATURE:
<223> OTHER INFORMATION: ALuc partial sequence

<400> SEQUENCE: 7
```

```
Met Met Tyr Pro Tyr Asp Val Pro
1               5

<210> SEQ ID NO 8
<211> LENGTH: 8
<212> TYPE: PRT
<213> ORGANISM: Artificial Sequence
<220> FEATURE:
<223> OTHER INFORMATION: ALuc partial sequence

<400> SEQUENCE: 8

Met Met Asp Tyr Lys Asp Asp Asp
1               5

<210> SEQ ID NO 9
<211> LENGTH: 5
<212> TYPE: PRT
<213> ORGANISM: Artificial Sequence
<220> FEATURE:
<223> OTHER INFORMATION: ALuc partial sequence

<400> SEQUENCE: 9

Thr Glu Glu Glu Thr
1               5

<210> SEQ ID NO 10
<211> LENGTH: 4
<212> TYPE: PRT
<213> ORGANISM: Artificial Sequence
<220> FEATURE:
<223> OTHER INFORMATION: ALuc partial sequence

<400> SEQUENCE: 10

Gly Glu Ala Ile
1

<210> SEQ ID NO 11
<211> LENGTH: 4
<212> TYPE: PRT
<213> ORGANISM: Artificial Sequence
<220> FEATURE:
<223> OTHER INFORMATION: ALuc partial sequence

<400> SEQUENCE: 11

Val Gly Ala Ile
1

<210> SEQ ID NO 12
<211> LENGTH: 4
<212> TYPE: PRT
<213> ORGANISM: Artificial Sequence
<220> FEATURE:
<223> OTHER INFORMATION: ALuc partial sequence

<400> SEQUENCE: 12

Gly Val Leu Gly
1

<210> SEQ ID NO 13
<211> LENGTH: 209
<212> TYPE: PRT
<213> ORGANISM: Artificial Sequence
<220> FEATURE:
<223> OTHER INFORMATION: ALuc10

<400> SEQUENCE: 13

Met Met Glu Ile Gln Val Leu Phe Ala Leu Ile Cys Phe Ala Leu Val
```

-continued

```
1                  5                  10                 15

Gln Ala Asn Pro Thr Glu Asn Lys Asp Asp Ile Asp Ile Val Gly Val
            20                  25                  30

Glu Gly Lys Phe Gly Thr Thr Asp Leu Glu Thr Asp Leu Phe Thr Ile
            35                  40                  45

Val Glu Asp Met Asn Val Ile Ser Arg Asp Thr Asn Leu Ala Asn Ser
        50                  55                  60

Asp Ala Asp Arg Gly Lys Leu Pro Gly Lys Lys Leu Pro Leu Glu Val
65                  70                  75                  80

Leu Lys Glu Leu Glu Ala Asn Ala Gln Lys Ala Gly Cys Thr Arg Gly
                    85                  90                  95

Cys Leu Ile Cys Leu Ser His Ile Lys Cys Thr Ala Lys Met Lys Lys
                100                 105                 110

Trp Leu Pro Gly Arg Cys Glu Ser Trp Glu Gly Asp Lys Glu Thr Gly
            115                 120                 125

Gln Gly Gly Ile Gly Glu Ala Ile Val Asp Ile Pro Glu Ile Pro Gly
        130                 135                 140

Phe Lys Asp Leu Glu Pro Met Glu Gln Phe Ile Ala Gln Val Asp Leu
145                 150                 155                 160

Cys Val Asp Cys Thr Thr Gly Cys Leu Lys Gly Leu Ala Asn Val Lys
                165                 170                 175

Cys Ser Asp Leu Leu Lys Lys Trp Leu Pro Ser Arg Cys Ala Thr Phe
            180                 185                 190

Ala Ser Lys Ile Gln Ala Gln Val Asp Lys Ile Lys Gly Ala Gly Gly
        195                 200                 205

Ser
```

<210> SEQ ID NO 14
<211> LENGTH: 209
<212> TYPE: PRT
<213> ORGANISM: Artificial Sequence
<220> FEATURE:
<223> OTHER INFORMATION: ALcu15

<400> SEQUENCE: 14

```
Met Met Gly Ile Lys Val Leu Phe Ala Leu Ile Cys Phe Ala Leu Val
1                  5                  10                 15

Gln Ala Asn Pro Thr Glu Asn Lys Asp Asp Ile Asp Ile Val Gly Val
            20                  25                  30

Glu Gly Lys Phe Gly Thr Thr Asp Leu Glu Thr Asp Leu Phe Thr Ile
            35                  40                  45

Val Glu Asp Met Asn Val Ile Ser Arg Asp Thr Asp Val Asp Ala Asn
        50                  55                  60

Arg Ala Asp Arg Gly Lys Leu Pro Gly Lys Lys Leu Pro Leu Glu Val
65                  70                  75                  80

Leu Lys Glu Leu Glu Ala Asn Ala Gln Lys Ala Gly Cys Thr Arg Gly
                    85                  90                  95

Cys Leu Ile Cys Leu Ser His Ile Lys Cys Thr Ala Lys Met Lys Lys
                100                 105                 110

Trp Leu Pro Gly Arg Cys Glu Ser Trp Glu Gly Asp Lys Glu Thr Gly
            115                 120                 125

Gln Gly Gly Ile Gly Glu Ala Ile Val Asp Ile Pro Glu Ile Pro Gly
        130                 135                 140

Phe Lys Asp Leu Glu Pro Met Glu Gln Phe Ile Ala Gln Val Asp Leu
145                 150                 155                 160
```

-continued

```
Cys Val Asp Cys Thr Thr Gly Cys Leu Lys Gly Leu Ala Asn Val Lys
                165                 170                 175

Cys Ser Asp Leu Leu Lys Lys Trp Leu Pro Ser Arg Cys Ala Thr Phe
            180                 185                 190

Ala Ser Lys Ile Gln Ala Gln Val Asp Lys Ile Lys Gly Ala Gly Gly
        195                 200                 205

Ser

<210> SEQ ID NO 15
<211> LENGTH: 212
<212> TYPE: PRT
<213> ORGANISM: Artificial Sequence
<220> FEATURE:
<223> OTHER INFORMATION: ALuc16

<400> SEQUENCE: 15

Met Met Gly Ile Lys Val Leu Phe Ala Leu Ile Cys Phe Ala Leu Val
1               5                   10                  15

Gln Ala Asn Pro Thr Glu Asn Lys Asp Asp Ile Asp Ile Val Gly Val
            20                  25                  30

Glu Gly Lys Phe Gly Thr Thr Asp Leu Glu Thr Asp Leu Phe Thr Ile
        35                  40                  45

Val Glu Asp Met Asn Val Ile Ser Arg Asp Thr Asp Val Asp Ala Asn
        50                  55                  60

Arg Ala Asp Arg Gly Arg Arg Gly Lys Leu Pro Gly Lys Lys Leu Pro
65                  70                  75                  80

Leu Glu Val Leu Lys Glu Leu Glu Ala Asn Ala Gln Lys Ala Gly Cys
                85                  90                  95

Thr Arg Gly Cys Leu Ile Cys Leu Ser His Ile Lys Cys Thr Ala Lys
            100                 105                 110

Met Lys Lys Trp Leu Pro Gly Arg Cys Glu Ser Trp Glu Gly Asp Lys
            115                 120                 125

Glu Thr Gly Gln Gly Gly Ile Gly Glu Ala Ile Val Asp Ile Pro Glu
        130                 135                 140

Ile Pro Gly Phe Lys Asp Leu Glu Pro Met Glu Gln Phe Ile Ala Gln
145                 150                 155                 160

Val Asp Leu Cys Val Asp Cys Thr Thr Gly Cys Leu Lys Gly Leu Ala
                165                 170                 175

Asn Val Lys Cys Ser Asp Leu Leu Lys Lys Trp Leu Pro Ser Arg Cys
            180                 185                 190

Ala Thr Phe Ala Ser Lys Ile Gln Ala Gln Val Asp Lys Ile Lys Gly
        195                 200                 205

Ala Gly Gly Ser
    210

<210> SEQ ID NO 16
<211> LENGTH: 212
<212> TYPE: PRT
<213> ORGANISM: Artificial Sequence
<220> FEATURE:
<223> OTHER INFORMATION: ALuc17

<400> SEQUENCE: 16

Met Met Gly Ile Lys Val Leu Phe Ala Leu Ile Cys Phe Ala Leu Val
1               5                   10                  15

Gln Ala Asn Pro Thr Glu Asn Lys Asp Asp Ile Asp Ile Val Gly Val
            20                  25                  30
```

```
Glu Gly Lys Phe Gly Thr Thr Asp Leu Glu Thr Asp Leu Phe Thr Ile
        35              40              45

Val Glu Asp Met Asn Val Ile Ser Arg Asp Thr Asp Val Asp Ala Asn
    50              55              60

Arg Ala Asp Arg Gly Arg Arg Gly Lys Met Pro Gly Lys Lys Leu Pro
65              70              75              80

Lys Ala Val Leu Ile Glu Leu Glu Ala Asn Ala Gln Lys Ala Gly Cys
                85              90              95

His Arg Gly Cys Leu Ile Cys Leu Ser His Ile Lys Cys Thr Ala Lys
            100             105             110

Met Lys Glu Trp Leu Pro Gly Arg Cys Glu Ser Trp Gly Gly Asp Lys
        115             120             125

Glu Thr Gly Gln Ala Gly Ile Val Gly Ala Ile Val Asp Ile Pro Glu
        130             135             140

Ile Pro Gly Phe Lys Asp Leu Glu Pro Met Glu Gln Phe Ile Ala Gln
145             150             155             160

Val Asp Leu Cys Val Asp Cys Thr Thr Gly Cys Leu Lys Gly Leu Ala
            165             170             175

Asn Val Lys Cys Ser Asp Leu Leu Lys Lys Trp Leu Pro Ser Arg Cys
            180             185             190

Ala Thr Phe Ala Ser Lys Ile Gln Ala Gln Val Asp Lys Ile Lys Gly
        195             200             205

Ala Gly Gly Ser
        210

<210> SEQ ID NO 17
<211> LENGTH: 215
<212> TYPE: PRT
<213> ORGANISM: Artificial Sequence
<220> FEATURE:
<223> OTHER INFORMATION: ALuc18

<400> SEQUENCE: 17

Met Met Gly Ile Lys Val Leu Phe Ala Leu Ile Cys Phe Ala Leu Val
1               5               10              15

Gln Ala Asn Pro Thr Glu Asn Lys Asp Asp Ile Asp Ile Val Gly Val
            20              25              30

Glu Gly Lys Phe Gly Thr Thr Asp Leu Glu Thr Asp Leu Phe Thr Ile
        35              40              45

Val Glu Asp Met Asn Val Ile Ser Arg Asp Thr Asp Val Asp Ala Asn
    50              55              60

Arg Ala Asp Arg Gly Arg Arg Gly His Gly Gly Leu Pro Gly Lys Lys
65              70              75              80

Met Pro Leu Glu Val Leu Leu Glu Leu Glu Ala Asn Ala Gln Arg Ala
        85              90              95

Gly Cys Thr Arg Gly Cys Leu Ile Cys Leu Ser Lys Ile Lys Cys Thr
            100             105             110

Ala Lys Met Lys Lys Trp Leu Pro Gly Arg Cys Glu Ser Trp Ala Gly
        115             120             125

Asp Lys Glu Thr Gly Gln Gly Gly Ile Thr Glu Glu Glu Thr Val Asp
        130             135             140

Ile Pro Glu Ile Pro Gly Phe Lys Asp Leu Glu Pro Met Glu Gln Phe
145             150             155             160

Ile Ala Gln Val Asp Leu Cys Val Asp Cys Thr Thr Gly Cys Leu Lys
            165             170             175
```

-continued

```
Gly Leu Ala Asn Val Lys Cys Ser Asp Leu Leu Lys Lys Trp Leu Pro
            180                 185                 190

Ser Arg Cys Ala Thr Phe Ala Ser Lys Ile Gln Ala Gln Val Asp Lys
        195                 200                 205

Ile Lys Gly Ala Gly Gly Ser
    210                 215
```

<210> SEQ ID NO 18
<211> LENGTH: 217
<212> TYPE: PRT
<213> ORGANISM: Artificial Sequence
<220> FEATURE:
<223> OTHER INFORMATION: ALuc19

<400> SEQUENCE: 18

```
Met Met Gly Ile Lys Val Leu Phe Ala Leu Ile Cys Phe Ala Leu Val
1               5                   10                  15

Gln Ala Asn Pro Thr Glu Asn Lys Asp Asp Ile Asp Ile Val Gly Val
            20                  25                  30

Glu Gly Lys Phe Gly Thr Thr Asp Leu Glu Thr Asp Leu Phe Thr Ile
        35                  40                  45

Val Glu Asp Met Asn Val Ile Ser Arg Asp Thr Asp Val Asp Ala Asn
    50                  55                  60

Arg Ala Asp Arg Gly Arg Arg Gly Arg Lys Leu Pro Gly Lys Lys Leu
65                  70                  75                  80

Pro Lys Glu Val Leu Lys Ile Leu Glu Ala Asn Ala Gln Arg Ala Gly
            85                  90                  95

Cys His Arg Gly Cys Leu Ile Cys Leu Ser His Ile Lys Cys Thr Ala
            100                 105                 110

Lys Met Lys Gln Trp Leu Pro Gly Arg Cys Glu Ser Trp Glu Gly Asp
            115                 120                 125

Lys Glu Thr Gly Gln Gly Gly Ile Gly Gly Pro Ile Val Asp Ile Gly
        130                 135                 140

Val Leu Gly Pro Glu Ile Pro Gly Phe Lys Asp Leu Glu Pro Met Glu
145                 150                 155                 160

Gln Phe Ile Ala Gln Val Asp Leu Cys Val Asp Cys Thr Thr Gly Cys
            165                 170                 175

Leu Lys Gly Leu Ala Asn Val Lys Cys Ser Asp Leu Leu Lys Lys Trp
            180                 185                 190

Leu Pro Ser Arg Cys Ala Thr Phe Ala Ser Lys Ile Gln Ala Gln Val
            195                 200                 205

Asp Lys Ile Lys Gly Ala Gly Gly Ser
    210                 215
```

<210> SEQ ID NO 19
<211> LENGTH: 212
<212> TYPE: PRT
<213> ORGANISM: Artificial Sequence
<220> FEATURE:
<223> OTHER INFORMATION: ALuc21

<400> SEQUENCE: 19

```
Met Met Gly Ile Lys Val Leu Phe Ala Leu Ile Cys Phe Ala Leu Val
1               5                   10                  15

Gln Ala Asn Ala Thr Ile Asn Glu Glu Asp Ile Asp Leu Val Ala Ile
            20                  25                  30

Gly Gly Ser Phe Ala Thr Thr Asp Leu Glu Thr Asp Leu Phe Thr Ile
```

-continued

```
               35                    40                   45
Val Glu Asp Met Asn Val Ile Ser Arg Asp Thr Asp Val Asp Ala Asn
    50                   55                   60

Arg Ala Asp Arg Gly Arg Arg Gly Lys Leu Pro Gly Lys Lys Leu Pro
65                   70                   75                   80

Leu Glu Val Leu Lys Glu Leu Glu Ala Asn Ala Gln Lys Ala Gly Cys
                85                   90                   95

Thr Arg Gly Cys Leu Ile Cys Leu Ser His Ile Lys Cys Thr Ala Lys
               100                  105                  110

Met Lys Lys Trp Leu Pro Gly Arg Cys Glu Ser Trp Glu Gly Asp Lys
               115                  120                  125

Glu Thr Gly Gln Gly Gly Ile Gly Glu Ala Ile Val Asp Ile Pro Glu
    130                  135                  140

Ile Pro Gly Phe Lys Asp Leu Glu Pro Met Glu Gln Phe Ile Ala Gln
145                  150                  155                  160

Val Asp Leu Cys Val Asp Cys Thr Thr Gly Cys Leu Lys Gly Leu Ala
               165                  170                  175

Asn Val Lys Cys Ser Asp Leu Leu Lys Lys Trp Leu Pro Ser Arg Cys
               180                  185                  190

Ala Thr Phe Ala Ser Lys Ile Gln Ala Gln Val Asp Lys Ile Lys Gly
               195                  200                  205

Ala Gly Gly Ser
    210

<210> SEQ ID NO 20
<211> LENGTH: 212
<212> TYPE: PRT
<213> ORGANISM: Artificial Sequence
<220> FEATURE:
<223> OTHER INFORMATION: ALuc22

<400> SEQUENCE: 20

Met Met Gly Val Lys Leu Ile Phe Ala Val Leu Cys Val Ala Val Ala
1               5                    10                   15

Gln Ala Asn Ala Thr Ile Asn Glu Asn Phe Glu Asp Ile Asp Leu Val
               20                   25                   30

Ala Ile Gly Gly Ser Phe Ala Asp Leu Glu Thr Asp Leu Phe Thr Ile
           35                    40                   45

Val Glu Asp Met Asn Val Ile Ser Arg Asp Thr Asp Val Asp Ala Asn
    50                   55                   60

Arg Gly Gly Arg Gly Arg Arg Gly Lys Leu Pro Gly Lys Lys Leu Pro
65                   70                   75                   80

Leu Glu Val Leu Lys Glu Leu Glu Ala Asn Ala Gln Lys Ala Gly Cys
                85                   90                   95

Thr Arg Gly Cys Leu Ile Cys Leu Ser His Ile Lys Cys Thr Ala Lys
               100                  105                  110

Met Lys Lys Trp Leu Pro Gly Arg Cys Glu Ser Trp Glu Gly Asp Lys
               115                  120                  125

Glu Thr Gly Gln Gly Gly Ile Gly Glu Ala Ile Val Asp Ile Pro Glu
    130                  135                  140

Ile Pro Gly Phe Lys Asp Leu Glu Pro Met Glu Gln Phe Ile Ala Gln
145                  150                  155                  160

Val Asp Leu Cys Val Asp Cys Thr Thr Gly Cys Leu Lys Gly Leu Ala
               165                  170                  175

Asn Val Lys Cys Ser Asp Leu Leu Lys Lys Trp Leu Pro Ser Arg Cys
```

-continued

```
                  180                 185                 190

Ala Thr Phe Ala Ser Lys Ile Gln Ala Gln Val Asp Lys Ile Lys Gly
        195                 200                 205

Ala Gly Gly Ser
    210

<210> SEQ ID NO 21
<211> LENGTH: 212
<212> TYPE: PRT
<213> ORGANISM: Artificial Sequence
<220> FEATURE:
<223> OTHER INFORMATION: ALuc23

<400> SEQUENCE: 21

Met Met Gly Ile Lys Val Leu Phe Ala Leu Ile Cys Phe Ala Leu Val
1               5                   10                  15

Gln Ala Asn Pro Thr Glu Asn Lys Asp Asp Ile Asp Ile Val Gly Val
            20                  25                  30

Glu Gly Lys Phe Gly Thr Thr Asp Leu Glu Thr Asp Leu Phe Thr Ile
        35                  40                  45

Val Glu Asp Met Asn Val Ile Ser Arg Asp Thr Asp Val Asp Ala Asn
    50                  55                  60

Arg Ala Asp Arg Gly Arg Arg Gly Lys Leu Pro Gly Lys Lys Leu Pro
65                  70                  75                  80

Leu Glu Val Leu Lys Glu Leu Glu Ala Asn Ala Gln Lys Ala Gly Cys
                85                  90                  95

Thr Arg Gly Cys Leu Ile Cys Leu Ser His Ile Lys Cys Thr Ala Lys
            100                 105                 110

Met Lys Lys Trp Leu Pro Gly Arg Cys Glu Ser Trp Glu Gly Asp Lys
        115                 120                 125

Glu Thr Gly Gln Gly Gly Ile Gly Glu Ala Ile Val Asp Ile Pro Glu
    130                 135                 140

Ile Pro Gly Phe Lys Glu Leu Ala Pro Met Glu Gln Phe Ile Ala Gln
145                 150                 155                 160

Val Asp Leu Cys Ala Asp Cys Thr Thr Gly Cys Leu Lys Gly Leu Ala
                165                 170                 175

Asn Val Lys Cys Ser Ala Leu Leu Lys Lys Trp Leu Pro Ser Arg Cys
            180                 185                 190

Ala Gly Phe Ala Asp Lys Ile Gln Ala Gln Val Asp Thr Ile Lys Gly
        195                 200                 205

Ala Gly Gly Ser
    210

<210> SEQ ID NO 22
<211> LENGTH: 212
<212> TYPE: PRT
<213> ORGANISM: Artificial Sequence
<220> FEATURE:
<223> OTHER INFORMATION: ALuc24

<400> SEQUENCE: 22

Met Met Gly Ile Lys Val Leu Phe Ala Leu Ile Cys Phe Ala Leu Val
1               5                   10                  15

Gln Ala Asn Pro Thr Glu Asn Lys Asp Asp Ile Asp Ile Val Gly Val
            20                  25                  30

Glu Gly Lys Phe Gly Thr Thr Asp Leu Glu Thr Asp Leu Phe Thr Ile
        35                  40                  45
```

-continued

```
Val Glu Asp Met Asn Val Ile Ser Arg Asp Thr Asp Val Asp Ala Asn
    50                  55                  60

Arg Ala Asp Arg Gly Arg Arg Gly Lys Leu Pro Gly Lys Lys Leu Pro
65                  70                  75                  80

Leu Glu Val Leu Lys Glu Leu Glu Ala Asn Ala Gln Lys Ala Gly Cys
                85                  90                  95

Thr Arg Gly Cys Leu Ile Cys Leu Ser His Ile Lys Cys Thr Ala Lys
                100                 105                 110

Met Lys Lys Trp Leu Pro Gly Arg Cys Glu Ser Trp Glu Gly Asp Lys
                115                 120                 125

Glu Thr Gly Gln Gly Gly Ile Gly Glu Ala Ile Val Asp Ile Pro Glu
        130                 135                 140

Ile Pro Gly Phe Lys Asn Met Ala Pro Met Glu Gln Phe Ile Ala Gln
145                 150                 155                 160

Val Asp Leu Cys Ala Asp Cys Thr Thr Gly Cys Leu Lys Gly Leu Ala
                165                 170                 175

Asn Val Lys Cys Ser Asn Leu Leu Lys Lys Trp Leu Pro Ser Arg Cys
                180                 185                 190

Lys Gly Phe Ala Asn Lys Ile Gln Ala Glu Val Asp Thr Ile Lys Gly
            195                 200                 205

Leu Gly Gly Ser
    210

<210> SEQ ID NO 23
<211> LENGTH: 212
<212> TYPE: PRT
<213> ORGANISM: Artificial Sequence
<220> FEATURE:
<223> OTHER INFORMATION: ALuc25

<400> SEQUENCE: 23

Met Met Gly Val Lys Leu Ile Phe Ala Val Leu Cys Val Ala Val Ala
1               5                   10                  15

Gln Ala Asn Ala Thr Ile Asn Glu Asn Phe Glu Asp Ile Asp Leu Val
                20                  25                  30

Ala Ile Gly Gly Ser Phe Ala Asp Leu Glu Thr Asp Leu Phe Thr Ile
            35                  40                  45

Val Glu Asp Met Asn Val Ile Ser Arg Asp Thr Asp Val Asp Ala Asn
    50                  55                  60

Arg Gly Gly Arg Gly Arg Gly Lys Leu Pro Gly Lys Lys Leu Pro
65                  70                  75                  80

Leu Glu Val Leu Lys Glu Leu Glu Ala Asn Ala Gln Lys Ala Gly Cys
                85                  90                  95

Thr Arg Gly Cys Leu Ile Cys Leu Ser His Ile Lys Cys Thr Ala Lys
                100                 105                 110

Met Lys Lys Trp Leu Pro Gly Arg Cys Glu Ser Trp Glu Gly Asp Lys
                115                 120                 125

Glu Thr Gly Gln Gly Gly Ile Gly Glu Ala Ile Val Asp Ile Pro Glu
        130                 135                 140

Ile Pro Gly Phe Lys Glu Leu Ala Pro Met Glu Gln Phe Ile Ala Gln
145                 150                 155                 160

Val Asp Leu Cys Ala Asp Cys Thr Thr Gly Cys Leu Lys Gly Leu Ala
                165                 170                 175

Asn Val Lys Cys Ser Ala Leu Leu Lys Lys Trp Leu Pro Ser Arg Cys
                180                 185                 190
```

-continued

```
Ala Gly Phe Ala Asp Lys Ile Gln Ala Gln Val Asp Thr Ile Lys Gly
        195                 200                 205

Ala Gly Gly Ser
    210

<210> SEQ ID NO 24
<211> LENGTH: 212
<212> TYPE: PRT
<213> ORGANISM: Artificial Sequence
<220> FEATURE:
<223> OTHER INFORMATION: ALuc26

<400> SEQUENCE: 24

Met Met Gly Val Lys Leu Ile Phe Ala Val Leu Cys Val Ala Val Ala
1               5                   10                  15

Gln Ala Asn Ala Thr Ile Asn Glu Asn Phe Glu Asp Ile Asp Leu Val
            20                  25                  30

Ala Ile Gly Gly Ser Phe Ala Asp Leu Glu Thr Asp Leu Phe Thr Ile
        35                  40                  45

Val Glu Asp Met Asn Val Ile Ser Arg Asp Thr Asp Val Asp Ala Asn
    50                  55                  60

Arg Gly Gly Arg Gly Arg Arg Gly Lys Leu Pro Gly Lys Lys Leu Pro
65                  70                  75                  80

Leu Glu Val Leu Lys Glu Leu Glu Ala Asn Ala Gln Lys Ala Gly Cys
            85                  90                  95

Thr Arg Gly Cys Leu Ile Cys Leu Ser His Ile Lys Cys Thr Ala Lys
            100                 105                 110

Met Lys Lys Trp Leu Pro Gly Arg Cys Glu Ser Trp Glu Gly Asp Lys
            115                 120                 125

Glu Thr Gly Gln Gly Gly Ile Gly Glu Ala Ile Val Asp Ile Pro Glu
        130                 135                 140

Ile Pro Gly Phe Lys Asn Leu Ala Pro Met Glu Gln Phe Ile Ala Gln
145                 150                 155                 160

Val Asp Leu Cys Ala Asp Cys Thr Thr Gly Cys Leu Lys Gly Leu Ala
                165                 170                 175

Asn Val Lys Cys Ser Asn Leu Leu Lys Lys Trp Leu Pro Ser Arg Cys
            180                 185                 190

Ala Gly Phe Ala Asn Lys Ile Gln Ala Gln Val Asp Thr Ile Lys Gly
        195                 200                 205

Leu Gly Gly Ser
    210

<210> SEQ ID NO 25
<211> LENGTH: 212
<212> TYPE: PRT
<213> ORGANISM: Artificial Sequence
<220> FEATURE:
<223> OTHER INFORMATION: ALuc27

<400> SEQUENCE: 25

Met Met Gly Val Lys Leu Ile Phe Ala Val Leu Cys Val Ala Val Ala
1               5                   10                  15

Gln Ala Asn Ala Thr Ile Asn Glu Asn Phe Glu Asp Ile Asp Leu Val
            20                  25                  30

Ala Ile Gly Gly Ser Phe Ala Asp Leu Glu Thr Asp Leu Phe Thr Ile
        35                  40                  45

Val Glu Asp Met Asn Val Ile Ser Arg Asp Thr Asp Val Asp Ala Asn
    50                  55                  60
```

-continued

```
Arg Gly Gly Arg Gly Arg Arg Gly Lys Leu Pro Gly Lys Lys Leu Pro
65              70              75              80

Leu Glu Val Leu Lys Glu Leu Glu Ala Asn Ala Gln Lys Ala Gly Cys
                85              90              95

Thr Arg Gly Cys Leu Ile Cys Leu Ser His Ile Lys Cys Thr Ala Lys
            100             105             110

Met Lys Lys Trp Leu Pro Gly Arg Cys Glu Ser Trp Glu Gly Asp Lys
            115             120             125

Glu Thr Gly Gln Gly Gly Ile Gly Glu Ala Ile Val Asp Ile Pro Glu
        130             135             140

Ile Pro Gly Phe Lys Phe Leu Ala Pro Met Glu Gln Phe Ile Ala Gln
145             150             155             160

Val Asp Leu Cys Ala Asp Cys Thr Thr Gly Cys Leu Lys Gly Leu Ala
            165             170             175

Asn Val Phe Cys Ser Phe Leu Leu Lys Lys Trp Leu Pro Ser Arg Cys
            180             185             190

Ala Gly Phe Ala Phe Lys Ile Gln Ala Gln Val Asp Thr Ile Lys Gly
            195             200             205

Leu Gly Gly Ser
        210

<210> SEQ ID NO 26
<211> LENGTH: 212
<212> TYPE: PRT
<213> ORGANISM: Artificial Sequence
<220> FEATURE:
<223> OTHER INFORMATION: ALuc28

<400> SEQUENCE: 26

Met Met Gly Val Lys Leu Ile Phe Ala Val Leu Cys Val Ala Val Ala
1               5               10              15

Gln Ala Asn Ala Thr Ile Asn Glu Asn Phe Glu Asp Ile Asp Leu Val
            20              25              30

Ala Ile Gly Gly Ser Phe Ala Asp Leu Glu Thr Asp Leu Phe Thr Ile
            35              40              45

Val Glu Asp Met Asn Val Ile Ser Arg Asp Thr Asp Val Asp Ala Asn
        50              55              60

Arg Gly Gly Arg Gly Arg Arg Gly Lys Leu Pro Gly Lys Lys Leu Pro
65              70              75              80

Leu Glu Val Leu Lys Glu Leu Glu Ala Asn Ala Gln Lys Ala Gly Cys
                85              90              95

Thr Arg Gly Cys Leu Ile Cys Leu Ser His Ile Lys Cys Thr Ala Lys
            100             105             110

Met Lys Lys Trp Leu Pro Gly Arg Cys Glu Ser Trp Glu Gly Asp Lys
            115             120             125

Glu Thr Gly Gln Gly Gly Ile Gly Glu Ala Ile Val Asp Ile Pro Glu
        130             135             140

Ile Pro Gly Phe Lys Tyr Leu Ala Pro Met Glu Gln Phe Ile Ala Gln
145             150             155             160

Val Asp Leu Cys Ala Asp Cys Thr Thr Gly Cys Leu Lys Gly Leu Ala
            165             170             175

Asn Val Tyr Cys Ser Tyr Leu Leu Lys Lys Trp Leu Pro Ser Arg Cys
            180             185             190

Ala Gly Phe Ala Tyr Lys Ile Gln Ala Gln Val Asp Thr Ile Lys Gly
            195             200             205
```

-continued

```
Leu Gly Gly Ser
    210

<210> SEQ ID NO 27
<211> LENGTH: 212
<212> TYPE: PRT
<213> ORGANISM: Artificial Sequence
<220> FEATURE:
<223> OTHER INFORMATION: ALuc29

<400> SEQUENCE: 27

Met Met Gly Val Lys Leu Ile Phe Ala Val Leu Cys Val Ala Val Ala
1               5                   10                  15

Gln Ala Asn Ala Thr Ile Asn Glu Asn Phe Glu Asp Ile Asp Leu Val
                20                  25                  30

Ala Ile Gly Gly Ser Phe Ala Asp Leu Glu Thr Asp Leu Phe Thr Ile
            35                  40                  45

Val Glu Asp Met Asn Val Ile Ser Arg Asp Thr Asp Val Asp Ala Asn
        50                  55                  60

Arg Gly Gly Arg Gly Arg Arg Gly Lys Leu Pro Gly Lys Lys Leu Pro
65                  70                  75                  80

Leu Glu Val Leu Lys Glu Leu Glu Ala Asn Ala Gln Lys Ala Gly Cys
                85                  90                  95

Thr Arg Gly Cys Leu Ile Cys Leu Ser His Ile Lys Cys Thr Ala Lys
            100                 105                 110

Met Lys Lys Trp Leu Pro Gly Arg Cys Glu Ser Trp Glu Gly Asp Lys
            115                 120                 125

Glu Thr Gly Gln Gly Gly Ile Gly Glu Ala Ile Val Asp Ile Pro Glu
        130                 135                 140

Ile Pro Gly Phe Lys Trp Leu Ala Pro Met Glu Gln Phe Ile Ala Gln
145                 150                 155                 160

Val Asp Leu Cys Ala Asp Cys Thr Thr Gly Cys Leu Lys Gly Leu Ala
            165                 170                 175

Asn Val Trp Cys Ser Trp Leu Leu Lys Lys Trp Leu Pro Ser Arg Cys
            180                 185                 190

Ala Gly Phe Ala Trp Lys Ile Gln Ala Gln Val Asp Thr Ile Lys Gly
            195                 200                 205

Leu Gly Gly Ser
    210

<210> SEQ ID NO 28
<211> LENGTH: 212
<212> TYPE: PRT
<213> ORGANISM: Artificial Sequence
<220> FEATURE:
<223> OTHER INFORMATION: ALuc30

<400> SEQUENCE: 28

Met Met Gly Ile Lys Val Leu Phe Ala Leu Ile Cys Phe Ala Leu Val
1               5                   10                  15

Gln Ala Asn His His His His His His His Asp Ile Val Gly Val
                20                  25                  30

Glu Gly Lys Phe Gly Thr Thr Asp Leu Glu Thr Asp Leu Phe Thr Ile
            35                  40                  45

Val Glu Asp Met Asn Val Ile Ser Arg Asp Thr Asp Val Asp Ala Asn
        50                  55                  60

Arg Ala Asp Arg Gly Arg Arg Gly Lys Leu Pro Gly Lys Lys Leu Pro
```

```
65                  70                  75                  80

Leu Glu Val Leu Lys Glu Leu Glu Ala Asn Ala Gln Lys Ala Gly Cys
                85                  90                  95

Thr Arg Gly Cys Leu Ile Cys Leu Ser His Ile Lys Cys Thr Ala Lys
                100                 105                 110

Met Lys Lys Trp Leu Pro Gly Arg Cys Glu Ser Trp Glu Gly Asp Lys
                115                 120                 125

Glu Thr Gly Gln Gly Gly Ile Gly Glu Ala Ile Val Asp Ile Pro Glu
                130                 135                 140

Ile Pro Gly Phe Lys Glu Leu Ala Pro Met Glu Gln Phe Ile Ala Gln
145                 150                 155                 160

Val Asp Leu Cys Ala Asp Cys Thr Thr Gly Cys Leu Lys Gly Leu Ala
                165                 170                 175

Asn Val Lys Cys Ser Ala Leu Leu Lys Lys Trp Leu Pro Ser Arg Cys
                180                 185                 190

Ala Gly Phe Ala Asp Lys Ile Gln Ala Gln Val Asp Thr Ile Lys Gly
                195                 200                 205

Ala Gly Gly Ser
        210

<210> SEQ ID NO 29
<211> LENGTH: 212
<212> TYPE: PRT
<213> ORGANISM: Artificial Sequence
<220> FEATURE:
<223> OTHER INFORMATION: ALuc31

<400> SEQUENCE: 29

Met Met Gly Ile Lys Val Leu Phe Ala Leu Ile Cys Phe Ala Leu Val
1               5                   10                  15

Gln Ala Asn His His His His His His His Asp Ile Val Gly Val
                20                  25                  30

Glu Gly Lys Phe Gly Thr Thr Asp Leu Glu Thr Asp Leu Phe Thr Ile
                35                  40                  45

Val Glu Asp Met Asn Val Ile Ser Arg Asp Thr Asp Val Asp Ala Asn
        50                  55                  60

Arg Ala Asp Arg Gly Arg Arg Gly Glu Leu Pro Gly Lys Lys Leu Pro
65                  70                  75                  80

Leu Glu Val Leu Lys Glu Leu Glu Ala Asn Ala Gln Lys Ala Gly Cys
                85                  90                  95

Thr Arg Gly Cys Leu Ile Cys Leu Ser His Ile Lys Cys Thr Ala Lys
                100                 105                 110

Met Lys Lys Trp Leu Pro Gly Arg Cys Glu Ser Trp Glu Gly Asp Lys
                115                 120                 125

Glu Thr Gly Gln Gly Gly Ile Gly Glu Ala Ile Val Asp Ile Pro Glu
                130                 135                 140

Ile Pro Gly Phe Lys Glu Leu Ala Pro Met Glu Gln Phe Ile Ala Gln
145                 150                 155                 160

Val Asp Leu Cys Ala Asp Cys Thr Thr Gly Cys Leu Lys Gly Leu Ala
                165                 170                 175

Asn Val Lys Cys Ser Ala Leu Leu Lys Lys Trp Leu Pro Ser Arg Cys
                180                 185                 190

Ala Gly Phe Ala Asp Lys Ile Gln Ala Gln Val Asp Thr Ile Lys Gly
                195                 200                 205

Ala Gly Gly Ser
```

-continued

210

<210> SEQ ID NO 30
<211> LENGTH: 212
<212> TYPE: PRT
<213> ORGANISM: Artificial Sequence
<220> FEATURE:
<223> OTHER INFORMATION: ALuc32

<400> SEQUENCE: 30

```
Met Met Gly Ile Lys Val Leu Phe Ala Leu Ile Cys Phe Ala Leu Val
1               5                   10                  15

Gln Ala Asn Glu Gln Lys Leu Ile Ser Glu Glu Asp Leu Val Gly Val
            20                  25                  30

Glu Gly Lys Phe Gly Thr Thr Asp Leu Glu Thr Asp Leu Phe Thr Ile
        35                  40                  45

Val Glu Asp Met Asn Val Ile Ser Arg Asp Thr Asp Val Asp Ala Asn
    50                  55                  60

Arg Ala Asp Arg Gly Arg Arg Gly Lys Leu Pro Gly Lys Lys Leu Pro
65                  70                  75                  80

Leu Glu Val Leu Lys Glu Leu Glu Ala Asn Ala Gln Lys Ala Gly Cys
                85                  90                  95

Thr Arg Gly Cys Leu Ile Cys Leu Ser His Ile Lys Cys Thr Ala Lys
            100                 105                 110

Met Lys Lys Trp Leu Pro Gly Arg Cys Glu Ser Trp Glu Gly Asp Lys
            115                 120                 125

Glu Thr Gly Gln Gly Gly Ile Gly Glu Ala Ile Val Asp Ile Pro Glu
        130                 135                 140

Ile Pro Gly Phe Lys Glu Leu Ala Pro Met Glu Gln Phe Ile Ala Gln
145                 150                 155                 160

Val Asp Leu Cys Ala Asp Cys Thr Thr Gly Cys Leu Lys Gly Leu Ala
                165                 170                 175

Asn Val Lys Cys Ser Ala Leu Leu Lys Lys Trp Leu Pro Ser Arg Cys
            180                 185                 190

Ala Gly Phe Ala Asp Lys Ile Gln Ala Gln Val Asp Thr Ile Lys Gly
            195                 200                 205

Ala Gly Gly Ser
        210
```

<210> SEQ ID NO 31
<211> LENGTH: 212
<212> TYPE: PRT
<213> ORGANISM: Artificial Sequence
<220> FEATURE:
<223> OTHER INFORMATION: ALuc33

<400> SEQUENCE: 31

```
Met Met Gly Ile Lys Val Leu Phe Ala Leu Ile Cys Phe Ala Leu Val
1               5                   10                  15

Gln Ala Asn Met Met Tyr Pro Tyr Asp Val Pro Asp Tyr Ala Gly Val
            20                  25                  30

Glu Gly Lys Phe Gly Thr Thr Asp Leu Glu Thr Asp Leu Phe Thr Ile
        35                  40                  45

Val Glu Asp Met Asn Val Ile Ser Arg Asp Thr Asp Val Asp Ala Asn
    50                  55                  60

Arg Ala Asp Arg Gly Arg Arg Gly Lys Leu Pro Gly Lys Lys Leu Pro
65                  70                  75                  80
```

-continued

```
Leu Glu Val Leu Lys Glu Leu Glu Ala Asn Ala Gln Lys Ala Gly Cys
            85                  90                  95

Thr Arg Gly Cys Leu Ile Cys Leu Ser His Ile Lys Cys Thr Ala Lys
            100                 105                 110

Met Lys Lys Trp Leu Pro Gly Arg Cys Glu Ser Trp Glu Gly Asp Lys
            115                 120                 125

Glu Thr Gly Gln Gly Gly Ile Gly Glu Ala Ile Val Asp Ile Pro Glu
        130                 135                 140

Ile Pro Gly Phe Lys Glu Leu Ala Pro Met Glu Gln Phe Ile Ala Gln
145                 150                 155                 160

Val Asp Leu Cys Ala Asp Cys Thr Thr Gly Cys Leu Lys Gly Leu Ala
                165                 170                 175

Asn Val Lys Cys Ser Ala Leu Leu Lys Lys Trp Leu Pro Ser Arg Cys
                180                 185                 190

Ala Gly Phe Ala Asp Lys Ile Gln Ala Gln Val Asp Thr Ile Lys Gly
            195                 200                 205

Ala Gly Gly Ser
        210
```

```
<210> SEQ ID NO 32
<211> LENGTH: 212
<212> TYPE: PRT
<213> ORGANISM: Artificial Sequence
<220> FEATURE:
<223> OTHER INFORMATION: ALuc34

<400> SEQUENCE: 32
```

```
Met Met Gly Ile Lys Val Leu Phe Ala Leu Ile Cys Phe Ala Leu Val
1               5                   10                  15

Gln Ala Asn Met Met Asp Tyr Lys Asp Asp Asp Lys Val Gly Val
            20                  25                  30

Glu Gly Lys Phe Gly Thr Thr Asp Leu Glu Thr Asp Leu Phe Thr Ile
            35                  40                  45

Val Glu Asp Met Asn Val Ile Ser Arg Asp Thr Asp Val Asp Ala Asn
        50                  55                  60

Arg Ala Asp Arg Gly Arg Arg Gly Lys Leu Pro Gly Lys Lys Leu Pro
65                  70                  75                  80

Leu Glu Val Leu Lys Glu Leu Glu Ala Asn Ala Gln Lys Ala Gly Cys
                85                  90                  95

Thr Arg Gly Cys Leu Ile Cys Leu Ser His Ile Lys Cys Thr Ala Lys
            100                 105                 110

Met Lys Lys Trp Leu Pro Gly Arg Cys Glu Ser Trp Glu Gly Asp Lys
            115                 120                 125

Glu Thr Gly Gln Gly Gly Ile Gly Glu Ala Ile Val Asp Ile Pro Glu
        130                 135                 140

Ile Pro Gly Phe Lys Glu Leu Ala Pro Met Glu Gln Phe Ile Ala Gln
145                 150                 155                 160

Val Asp Leu Cys Ala Asp Cys Thr Thr Gly Cys Leu Lys Gly Leu Ala
                165                 170                 175

Asn Val Lys Cys Ser Ala Leu Leu Lys Lys Trp Leu Pro Ser Arg Cys
                180                 185                 190

Ala Gly Phe Ala Asp Lys Ile Gln Ala Gln Val Asp Thr Ile Lys Gly
            195                 200                 205

Ala Gly Gly Ser
        210
```

```
<210> SEQ ID NO 33
<211> LENGTH: 194
<212> TYPE: PRT
<213> ORGANISM: Artificial Sequence
<220> FEATURE:
<223> OTHER INFORMATION: ALuc41

<400> SEQUENCE: 33

Met Met Gly Ile Lys Val Leu Phe Ala Leu Val Cys Leu Ala Leu Val
1               5                   10                  15

Gln Ala Lys Pro Thr Glu Asp Glu Glu Asp Asp Ile Val Asp Val
            20                  25                  30

Val Gly Asn Phe Trp Ala Ile Gly Val Asp Asn Asp Arg Asp Phe Thr
            35                  40                  45

Ile Ser Ala Asp Arg Gly Lys Leu Pro Gly Lys Lys Leu Pro Lys Glu
        50                  55                  60

Val Leu Ile Glu Ile Glu Ala Asn Ala Lys Lys Ala Gly Cys Thr Arg
65                  70                  75                  80

Gly Cys Leu Ile Cys Leu Ser Lys Ile Lys Cys Thr Ala Lys Met Lys
                85                  90                  95

Lys Trp Leu Pro Gly Arg Cys His Ser Tyr Glu Gly Asp Lys Asp Thr
            100                 105                 110

Gly Gln Gly Gly Ile Gly Glu Pro Ile Val Asp Ala Pro Glu Ile Pro
            115                 120                 125

Gly Phe Lys Asp Leu Thr Pro Met Glu Gln Phe Ile Ala Gln Val Asp
        130                 135                 140

Leu Cys Ala Asp Cys Thr Thr Gly Cys Leu Lys Gly Leu Ala Asn Val
145                 150                 155                 160

Lys Cys Ser Ala Leu Leu Lys Lys Trp Leu Pro Asp Arg Cys Ala Ser
                165                 170                 175

Phe Ala Asp Lys Ile Gln Lys Glu Val Asp Thr Ile Lys Gly Leu Ala
                180                 185                 190

Gly Ser

<210> SEQ ID NO 34
<211> LENGTH: 213
<212> TYPE: PRT
<213> ORGANISM: Artificial Sequence
<220> FEATURE:
<223> OTHER INFORMATION: ALuc42

<400> SEQUENCE: 34

Met Met Gly Ile Lys Val Leu Phe Ala Leu Val Cys Leu Ala Leu Val
1               5                   10                  15

Gln Ala Asn His His His His His His His Asp Ile Val Asp Val
            20                  25                  30

Val Gly Asn Phe Trp Ala Ile Gly Val Asp Asn Asp Arg Asp Phe Thr
            35                  40                  45

Ile Ser Glu Asp Met Asn Val Ile Ser Arg Asp Thr Asp Val Asp Ala
        50                  55                  60

Asn Arg Ala Asp Arg Ala Asp Arg Gly Lys Leu Pro Gly Lys Lys Leu
65                  70                  75                  80

Pro Lys Glu Val Leu Ile Glu Ile Glu Ala Asn Ala Lys Lys Ala Gly
                85                  90                  95

Cys Thr Arg Gly Cys Leu Ile Cys Leu Ser Lys Ile Lys Cys Thr Ala
            100                 105                 110
```

-continued

```
Lys Met Lys Lys Trp Leu Pro Gly Arg Cys His Ser Tyr Glu Gly Asp
        115                 120                 125

Lys Asp Thr Gly Gln Gly Gly Ile Gly Glu Pro Ile Val Asp Ala Pro
    130                 135                 140

Glu Ile Pro Gly Phe Lys Asp Leu Thr Pro Met Glu Gln Phe Ile Ala
145                 150                 155                 160

Gln Val Asp Leu Cys Ala Asp Cys Thr Thr Gly Cys Leu Lys Gly Leu
                165                 170                 175

Ala Asn Val Lys Cys Ser Ala Leu Leu Lys Lys Trp Leu Pro Asp Arg
                180                 185                 190

Cys Ala Ser Phe Ala Asp Lys Ile Gln Lys Glu Val Asp Thr Ile Lys
            195                 200                 205

Gly Leu Ala Gly Ser
        210
```

```
<210> SEQ ID NO 35
<211> LENGTH: 194
<212> TYPE: PRT
<213> ORGANISM: Artificial Sequence
<220> FEATURE:
<223> OTHER INFORMATION: ALuc43

<400> SEQUENCE: 35

Met Met Gly Ile Lys Val Leu Phe Ala Leu Val Cys Leu Ala Leu Val
1               5                   10                  15

Gln Ala Lys Pro Thr Glu Asp Glu Asp Asp Ile Val Asp Val
                20                  25                  30

Val Gly Asn Phe Trp Ala Ile Gly Val Asp Asn Asp Arg Asp Phe Thr
            35                  40                  45

Ile Ser Ala Asp Arg Gly Lys Leu Pro Gly Lys Lys Leu Pro Lys Glu
    50                  55                  60

Val Leu Ile Glu Ile Glu Ala Asn Ala Lys Lys Ala Gly Cys Thr Arg
65                  70                  75                  80

Gly Cys Leu Ile Cys Leu Ser Lys Ile Lys Cys Thr Ala Lys Met Lys
                85                  90                  95

Lys Trp Leu Pro Gly Arg Cys His Ser Tyr Glu Gly Asp Lys Asp Thr
            100                 105                 110

Gly Gln Gly Gly Ile Gly Glu Pro Ile Val Asp Ala Pro Glu Ile Pro
        115                 120                 125

Gly Phe Lys Asp Leu Thr Pro Met Glu Gln Phe Ile Ala Gln Val Asp
    130                 135                 140

Leu Cys Ala Asp Cys Thr Thr Gly Cys Leu Lys Gly Leu Ala Asn Val
145                 150                 155                 160

Lys Cys Ser Ala Leu Leu Lys Lys Trp Leu Pro Asp Arg Cys Ala Ser
                165                 170                 175

Phe Ala Asp Lys Ile Gln Thr Glu Val Asp Thr Ile Lys Gly Leu Ala
                180                 185                 190

Gly Ser
```

```
<210> SEQ ID NO 36
<211> LENGTH: 194
<212> TYPE: PRT
<213> ORGANISM: Artificial Sequence
<220> FEATURE:
<223> OTHER INFORMATION: ALuc44

<400> SEQUENCE: 36
```

-continued

```
Met Met Gly Ile Lys Val Leu Phe Ala Leu Val Cys Leu Ala Leu Val
1               5                   10                  15

Gln Ala Lys Pro Thr Glu Asp Glu Asp Glu Asp Asp Ile Val Asp Val
            20                  25                  30

Val Gly Asn Phe Trp Ala Ile Gly Val Asp Asn Asp Arg Asp Phe Thr
            35                  40                  45

Ile Ser Ala Asp Arg Gly Lys Leu Pro Gly Lys Lys Leu Pro Lys Glu
        50                  55                  60

Val Leu Ile Glu Ile Glu Ala Asn Ala Lys Lys Ala Gly Cys Thr Arg
65                  70                  75                  80

Gly Cys Leu Ile Cys Leu Ser Lys Ile Lys Cys Thr Ala Lys Met Lys
                85                  90                  95

Lys Trp Leu Pro Gly Arg Cys His Ser Tyr Glu Gly Asp Lys Asp Thr
            100                 105                 110

Gly Gln Gly Gly Ile Gly Glu Pro Ile Val Asp Ala Pro Glu Ile Pro
            115                 120                 125

Gly Phe Lys Asp Leu Thr Pro Met Glu Gln Phe Ile Ala Gln Val Asp
        130                 135                 140

Leu Cys Ala Asp Cys Thr Thr Gly Cys Leu Lys Gly Leu Ala Asn Val
145                 150                 155                 160

Lys Cys Ser Ala Leu Leu Lys Lys Trp Leu Pro Asp Arg Cys Ala Ser
            165                 170                 175

Phe Ala Asp Lys Ile Gln Lys Glu Gln Asp Thr Ile Lys Gly Leu Ala
            180                 185                 190

Gly Ser
```

<210> SEQ ID NO 37
<211> LENGTH: 194
<212> TYPE: PRT
<213> ORGANISM: Artificial Sequence
<220> FEATURE:
<223> OTHER INFORMATION: ALuc45

<400> SEQUENCE: 37

```
Met Met Gly Ile Lys Val Leu Phe Ala Leu Val Cys Leu Ala Leu Val
1               5                   10                  15

Gln Ala Lys Pro Thr Glu Asp Glu Asp Glu Asp Asp Ile Val Asp Val
            20                  25                  30

Val Gly Asn Phe Trp Ala Ile Gly Val Asp Asn Asp Arg Asp Phe Thr
            35                  40                  45

Ile Ser Ala Asp Arg Gly Lys Leu Pro Gly Lys Lys Leu Pro Lys Glu
        50                  55                  60

Val Leu Ile Glu Ile Glu Ala Asn Ala Lys Lys Ala Gly Cys Thr Arg
65                  70                  75                  80

Gly Cys Leu Ile Cys Leu Ser Lys Ile Lys Cys Thr Ala Lys Met Lys
                85                  90                  95

Lys Trp Leu Pro Gly Arg Cys His Ser Tyr Glu Gly Asp Lys Asp Thr
            100                 105                 110

Gly Gln Gly Gly Ile Gly Glu Pro Ile Val Asp Ala Pro Glu Ile Pro
            115                 120                 125

Gly Phe Lys Asp Leu Thr Pro Met Glu Gln Phe Ile Ala Gln Val Asp
        130                 135                 140

Leu Cys Ala Asp Cys Thr Thr Gly Cys Leu Lys Gly Leu Ala Asn Val
145                 150                 155                 160

Lys Cys Ser Ala Leu Leu Lys Lys Trp Leu Pro Asp Arg Cys Ala Ser
```

-continued

```
                165                 170                 175
Phe Ala Asp Lys Ile Gln Lys Glu Val Asp Asn Ile Lys Gly Leu Ala
            180                 185                 190

Gly Ser

<210> SEQ ID NO 38
<211> LENGTH: 194
<212> TYPE: PRT
<213> ORGANISM: Artificial Sequence
<220> FEATURE:
<223> OTHER INFORMATION: ALuc46

<400> SEQUENCE: 38

Met Met Gly Ile Lys Val Leu Phe Ala Leu Val Cys Leu Ala Leu Val
1               5                   10                  15

Gln Ala Lys Pro Thr Glu Asp Glu Asp Glu Asp Asp Ile Val Asp Val
            20                  25                  30

Val Gly Asn Phe Trp Ala Ile Gly Val Asp Asn Asp Arg Asp Phe Thr
            35                  40                  45

Ile Ser Ala Asp Arg Gly Lys Leu Pro Gly Lys Lys Leu Pro Lys Glu
        50                  55                  60

Val Leu Ile Glu Ile Glu Ala Asn Ala Lys Lys Ala Gly Cys Thr Arg
65                  70                  75                  80

Gly Cys Leu Ile Cys Leu Ser Lys Ile Lys Cys Thr Ala Lys Met Lys
                85                  90                  95

Lys Trp Leu Pro Gly Arg Cys His Ser Tyr Glu Gly Asp Lys Asp Thr
            100                 105                 110

Gly Gln Gly Gly Ile Gly Glu Pro Ile Val Asp Ala Pro Glu Ile Pro
        115                 120                 125

Gly Phe Lys Asp Leu Thr Pro Met Glu Gln Phe Ile Ala Gln Val Asp
        130                 135                 140

Leu Cys Ala Asp Cys Thr Thr Gly Cys Leu Lys Gly Leu Ala Asn Val
145                 150                 155                 160

Lys Cys Ser Ala Leu Leu Lys Lys Trp Leu Pro Asp Arg Cys Ala Ser
                165                 170                 175

Phe Ala Asp Lys Ile Gln Ser Glu Val Ala Thr Ile Lys Gly Leu Ala
            180                 185                 190

Gly Ser

<210> SEQ ID NO 39
<211> LENGTH: 194
<212> TYPE: PRT
<213> ORGANISM: Artificial Sequence
<220> FEATURE:
<223> OTHER INFORMATION: ALuc47

<400> SEQUENCE: 39

Met Met Gly Ile Lys Val Leu Phe Ala Leu Val Cys Leu Ala Leu Val
1               5                   10                  15

Gln Ala Lys Pro Thr Glu Asp Glu Asp Glu Asp Asp Ile Val Asp Val
            20                  25                  30

Val Gly Asn Phe Trp Ala Ile Gly Val Asp Asn Asp Arg Asp Phe Thr
            35                  40                  45

Ile Ser Ala Asp Arg Gly Lys Leu Pro Gly Lys Lys Leu Pro Lys Glu
        50                  55                  60

Val Leu Ile Glu Ile Glu Ala Asn Ala Lys Lys Ala Gly Cys Thr Arg
65                  70                  75                  80
```

-continued

```
Gly Cys Leu Ile Cys Leu Ser Lys Ile Lys Cys Thr Ala Lys Met Lys
                85                  90                  95

Lys Trp Leu Pro Gly Arg Cys His Ser Tyr Glu Gly Asp Lys Asp Thr
               100                 105                 110

Gly Gln Gly Gly Ile Gly Glu Pro Ile Val Asp Ala Pro Glu Ile Pro
           115                 120                 125

Gly Phe Lys Asp Leu Thr Pro Met Glu Gln Phe Ile Ala Gln Val Asp
       130                 135                 140

Leu Cys Ala Asp Cys Thr Thr Gly Cys Leu Lys Gly Leu Ala Asn Val
145                 150                 155                 160

Lys Cys Ser Ala Leu Leu Lys Lys Trp Leu Pro Asp Arg Cys Ala Ser
               165                 170                 175

Phe Ala Asp Lys Ile Gln Lys Glu Val Gly Thr Ile Lys Gly Leu Leu
           180                 185                 190

Gly Ser
```

```
<210> SEQ ID NO 40
<211> LENGTH: 215
<212> TYPE: PRT
<213> ORGANISM: Artificial Sequence
<220> FEATURE:
<223> OTHER INFORMATION: ALuc48

<400> SEQUENCE: 40
```

```
Met Met Gly Ile Lys Val Leu Phe Ala Leu Ile Cys Phe Ala Leu Val
1               5                   10                  15

Gln Ala Asn Pro Thr Glu Asn Lys Asp Asp Ile Asp Ile Val Gly Val
               20                  25                  30

Glu Gly Lys Phe Gly Thr Thr Asp Leu Glu Thr Asp Leu Phe Thr Ile
           35                  40                  45

Val Glu Asp Met Asn Val Ile Ser Arg Asp Thr Asp Val Asp Ala Asn
       50                  55                  60

Arg Ala Asp Arg Gly Arg Arg Gly His Gly Gly Leu Pro Gly Lys Lys
65                  70                  75                  80

Met Pro Leu Glu Val Leu Leu Glu Leu Glu Ala Asn Ala Gln Arg Ala
               85                  90                  95

Gly Cys Thr Arg Gly Cys Leu Ile Cys Leu Ser Lys Ile Lys Cys Thr
               100                 105                 110

Ala Lys Met Lys Lys Trp Leu Pro Gly Arg Cys Glu Ser Trp Ala Gly
           115                 120                 125

Asp Lys Glu Thr Gly Gln Gly Gly Ile Thr Glu Glu Glu Thr Val Asp
       130                 135                 140

Ile Pro Glu Ile Pro Gly Phe Lys Asp Leu Glu Pro Met Glu Gln Phe
145                 150                 155                 160

Ile Ala Gln Val Asp Leu Cys Val Asp Cys Thr Thr Gly Cys Leu Lys
               165                 170                 175

Gly Leu Ala Asn Val Lys Cys Ser Asp Leu Leu Lys Lys Trp Leu Pro
               180                 185                 190

Ser Arg Cys Ala Thr Phe Ala Ser Lys Ile Gln Ala Gln Val Asp Lys
           195                 200                 205

Ile Lys Gly Ala Gly Gly Ser
       210                 215
```

```
<210> SEQ ID NO 41
<211> LENGTH: 194
```

```
<212> TYPE: PRT
<213> ORGANISM: Artificial Sequence
<220> FEATURE:
<223> OTHER INFORMATION: ALuc49

<400> SEQUENCE: 41

Met Met Gly Ile Lys Val Leu Phe Ala Leu Val Cys Leu Ala Leu Val
1               5                   10                  15

Gln Ala Lys Pro Thr Glu Asp Glu Asp Glu Asp Asp Ile Val Asp Val
                20                  25                  30

Val Gly Asn Phe Trp Ala Ile Gly Val Asp Asn Asp Arg Asp Phe Thr
            35                  40                  45

Ile Ser Ala Asp Arg Gly Lys Leu Pro Gly Lys Lys Leu Pro Lys Glu
        50                  55                  60

Val Leu Ile Glu Ile Glu Ala Asn Ala Lys Lys Ala Gly Cys Thr Arg
65                  70                  75                  80

Gly Cys Leu Ile Cys Leu Ser Lys Ile Lys Cys Thr Ala Lys Met Lys
                85                  90                  95

Lys Trp Leu Pro Gly Arg Cys His Ser Tyr Glu Gly Asp Lys Asp Thr
            100                 105                 110

Gly Gln Gly Gly Ile Gly Glu Pro Ile Val Asp Ala Pro Glu Ile Pro
        115                 120                 125

Gly Phe Lys Asp Leu Thr Pro Met Glu Gln Phe Ile Ala Gln Val Asp
        130                 135                 140

Leu Cys Ala Asp Cys Thr Thr Gly Cys Leu Lys Gly Leu Ala Asn Val
145                 150                 155                 160

Lys Cys Ser Ala Leu Leu Lys Lys Trp Leu Pro Asp Arg Cys Ala Ser
                165                 170                 175

Phe Ala Asp Lys Ile Gln Lys Glu Val Asp Tyr Ile Lys Gly Leu Ala
            180                 185                 190

Gly Ser

<210> SEQ ID NO 42
<211> LENGTH: 194
<212> TYPE: PRT
<213> ORGANISM: Artificial Sequence
<220> FEATURE:
<223> OTHER INFORMATION: ALuc50

<400> SEQUENCE: 42

Met Met Gly Ile Lys Val Leu Phe Ala Leu Val Cys Leu Ala Leu Val
1               5                   10                  15

Gln Ala Lys Pro Thr Glu Asp Glu Asp Glu Asp Asp Ile Val Asp Val
                20                  25                  30

Val Gly Asn Phe Trp Ala Ile Gly Val Asp Asn Asp Arg Asp Phe Thr
            35                  40                  45

Ile Ser Ala Asp Arg Gly Lys Leu Pro Gly Lys Lys Leu Pro Lys Glu
        50                  55                  60

Val Leu Ile Glu Ile Glu Ala Asn Ala Lys Lys Ala Gly Cys Thr Arg
65                  70                  75                  80

Gly Cys Leu Ile Cys Leu Ser Lys Ile Lys Cys Thr Ala Lys Met Lys
                85                  90                  95

Lys Trp Leu Pro Gly Arg Cys His Ser Tyr Glu Gly Asp Lys Asp Thr
            100                 105                 110

Gly Gln Gly Gly Ile Gly Glu Pro Ile Val Asp Ala Pro Glu Ile Pro
        115                 120                 125
```

-continued

```
Gly Phe Lys Asp Leu Thr Pro Met Glu Gln Phe Ile Ala Gln Val Asp
    130                 135                 140

Leu Cys Ala Asp Cys Thr Thr Gly Cys Leu Lys Gly Leu Ala Asn Val
145                 150                 155                 160

Lys Cys Ser Ala Leu Leu Lys Lys Trp Leu Pro Asp Arg Cys Ala Ser
                165                 170                 175

Phe Ala Asp Lys Ile Gln Lys Glu Val Asp Phe Ile Lys Gly Leu Ala
                180                 185                 190

Gly Ser
```

<210> SEQ ID NO 43
<211> LENGTH: 194
<212> TYPE: PRT
<213> ORGANISM: Artificial Sequence
<220> FEATURE:
<223> OTHER INFORMATION: ALuc51

<400> SEQUENCE: 43

```
Met Met Gly Ile Lys Val Leu Phe Ala Leu Val Cys Leu Ala Leu Val
1               5                   10                  15

Gln Ala Lys Pro Thr Glu Asp Glu Asp Asp Ile Val Asp Val
                20                  25                  30

Val Gly Asn Phe Trp Ala Ile Gly Val Asp Asn Asp Arg Asp Phe Thr
            35                  40                  45

Ile Ser Ala Asp Arg Gly Lys Leu Pro Gly Lys Lys Leu Pro Lys Glu
        50                  55                  60

Val Leu Ile Glu Ile Glu Ala Asn Ala Lys Lys Ala Gly Cys Thr Arg
65                  70                  75                  80

Gly Cys Leu Ile Cys Leu Ser Lys Ile Lys Cys Thr Ala Lys Met Lys
                85                  90                  95

Lys Trp Leu Pro Gly Arg Cys His Ser Tyr Glu Gly Asp Lys Asp Thr
                100                 105                 110

Gly Gln Gly Gly Ile Gly Glu Pro Ile Val Asp Ala Pro Glu Ile Pro
            115                 120                 125

Gly Phe Lys Asp Leu Thr Pro Met Glu Gln Phe Ile Ala Gln Val Asp
    130                 135                 140

Leu Cys Ala Asp Cys Thr Thr Gly Cys Leu Lys Gly Leu Ala Asn Val
145                 150                 155                 160

Lys Cys Ser Ala Leu Leu Lys Lys Trp Leu Pro Asp Arg Cys Ala Ser
                165                 170                 175

Phe Ala Asp Lys Ile Gln Lys Glu Val Asp Trp Ile Lys Gly Leu Ala
                180                 185                 190

Gly Ser
```

<210> SEQ ID NO 44
<211> LENGTH: 212
<212> TYPE: PRT
<213> ORGANISM: Artificial Sequence
<220> FEATURE:
<223> OTHER INFORMATION: ALuc52

<400> SEQUENCE: 44

```
Met Met Gly Ile Lys Val Leu Phe Ala Leu Ile Cys Phe Ala Leu Val
1               5                   10                  15

Gln Ala Asn His His His His His His His Asp Ile Val Gly Val
                20                  25                  30

Glu Gly Lys Phe Gly Thr Thr Asp Leu Glu Thr Asp Leu Phe Thr Ile
```

-continued

```
                35                40                45
Val Glu Asp Met Asn Val Ile Ser Arg Asp Thr Asp Val Asp Ala Asn
    50                55                60

Arg Ala Asp Arg Gly Arg Arg Gly Lys Leu Pro Gly Lys Lys Leu Pro
65                70                75                80

Leu Glu Val Leu Lys Glu Leu Glu Ala Asn Ala Gln Lys Ala Gly Cys
            85                90                95

Thr Arg Gly Cys Leu Ile Cys Leu Ser His Asp Trp Cys Thr Ala Lys
            100               105               110

Met Lys Lys Trp Leu Pro Gly Arg Cys Glu Ser Trp Glu Gly Asp Lys
            115               120               125

Glu Thr Gly Gln Gly Gly Ile Gly Glu Ala Val Val Asp Ile Leu Glu
    130               135               140

Ile Pro Gly Phe Lys Glu Leu Ala Pro Met Glu Gln Phe Ile Ala Gln
145               150               155               160

Val Asp Leu Cys Ala Asp Cys Thr Thr Gly Cys Leu Lys Gly Leu Ala
            165               170               175

Asn Val Lys Cys Ser Ala Leu Leu Lys Lys Trp Leu Pro Ser Arg Cys
            180               185               190

Ala Gly Phe Ala Asp Lys Ile Gln Ala Gln Val Asp Thr Ile Lys Gly
            195               200               205

Ala Gly Gly Ser
    210

<210> SEQ ID NO 45
<211> LENGTH: 212
<212> TYPE: PRT
<213> ORGANISM: Artificial Sequence
<220> FEATURE:
<223> OTHER INFORMATION: ALuc53

<400> SEQUENCE: 45

Met Met Gly Ile Lys Val Leu Phe Ala Leu Ile Cys Phe Ala Leu Val
1               5                 10                15

Gln Ala Asn His His His His His His His Asp Ile Val Gly Val
            20                25                30

Glu Gly Lys Phe Gly Asn Thr Asp Leu Glu Thr Asp Leu Phe Thr Ile
            35                40                45

Val Glu Asp Met Asn Val Ile Ser Arg Asp Thr Asp Val Asp Ala Asn
    50                55                60

Arg Ala Asp Arg Gly Arg Arg Gly Lys Leu Pro Gly Lys Lys Leu Pro
65                70                75                80

Leu Glu Val Leu Lys Glu Leu Glu Ala Asn Ala Gln Lys Ala Gly Cys
            85                90                95

Thr Arg Gly Cys Leu Ile Cys Leu Ser His Asp Trp Cys Thr Ala Lys
            100               105               110

Met Lys Lys Trp Leu Pro Gly Arg Cys Glu Ser Trp Glu Gly Asp Lys
            115               120               125

Glu Thr Gly Gln Gly Gly Ile Gly Glu Ala Val Val Asp Ile Pro Glu
    130               135               140

Ile Pro Gly Phe Lys Glu Leu Ala Pro Met Glu Gln Phe Ile Ala Gln
145               150               155               160

Val Asp Leu Cys Ala Asp Cys Thr Thr Gly Cys Leu Lys Gly Leu Ala
            165               170               175

Asn Val Lys Cys Ser Ala Leu Leu Lys Lys Trp Leu Pro Ser Arg Cys
```

-continued

```
                180                 185                 190
Ala Gly Phe Ala Asp Lys Ile Gln Ala Gln Val Asp Thr Ile Lys Gly
        195                 200                 205

Ala Gly Gly Ser
    210

<210> SEQ ID NO 46
<211> LENGTH: 212
<212> TYPE: PRT
<213> ORGANISM: Artificial Sequence
<220> FEATURE:
<223> OTHER INFORMATION: ALuc55

<400> SEQUENCE: 46

Met Met Gly Ile Lys Val Leu Phe Ala Leu Ile Cys Phe Ala Leu Val
1               5                   10                  15

Gln Ala Asn His His His His His His His Asp Ile Val Gly Val
            20                  25                  30

Glu Gly Lys Phe Gly Thr Thr Asp Leu Glu Thr Asp Leu Phe Thr Ile
        35                  40                  45

Val Glu Asp Met Asn Val Ile Ser Arg Asp Thr Asp Val Asp Ala Asn
    50                  55                  60

Arg Ala Asp Arg Gly Arg Arg Gly Lys Leu Pro Gly Lys Lys Leu Pro
65                  70                  75                  80

Leu Glu Val Leu Lys Glu Leu Glu Ala Asn Ala Gln Lys Ala Gly Cys
                85                  90                  95

Thr Arg Gly Cys Leu Ile Cys Leu Ser His Ile Lys Cys Thr Ala Lys
                100                 105                 110

Met Lys Lys Trp Leu Pro Gly Arg Cys Glu Ser Trp Glu Gly Asp Glu
            115                 120                 125

Glu Thr Gly Gln Gly Gly Ile Gly Glu Ala Ile Val Asp Ile Pro Glu
    130                 135                 140

Ile Pro Gly Phe Lys Glu Leu Ala Pro Met Glu Gln Phe Ile Ala Gln
145                 150                 155                 160

Val Asp Leu Cys Ala Asp Cys Thr Thr Gly Cys Trp Lys Gly Trp Ala
                165                 170                 175

Asn Leu Lys Cys Ser Ala Leu Leu Lys Lys Trp Leu Pro Ser Arg Cys
                180                 185                 190

Ala Gly Phe Ala Asp Lys Ile Gln Ala Gln Val Asp Thr Ile Lys Gly
        195                 200                 205

Ala Gly Gly Ser
    210

<210> SEQ ID NO 47
<211> LENGTH: 212
<212> TYPE: PRT
<213> ORGANISM: Artificial Sequence
<220> FEATURE:
<223> OTHER INFORMATION: ALuc56

<400> SEQUENCE: 47

Met Met Gly Ile Lys Val Leu Phe Ala Leu Ile Cys Phe Ala Leu Val
1               5                   10                  15

Gln Ala Asn His His His His His His His Asp Ile Val Gly Val
            20                  25                  30

Glu Gly Lys Phe Gly Thr Thr Asp Leu Glu Thr Asp Leu Phe Thr Ile
        35                  40                  45
```

-continued

Val Glu Asp Met Asn Val Ile Ser Arg Asp Thr Asp Val Asp Ala Asn
    50                  55                  60

Arg Ala Asp Arg Gly Arg Arg Gly Lys Leu Pro Gly Lys Lys Leu Pro
65                  70                  75                  80

Leu Glu Val Leu Lys Glu Leu Glu Ala Asn Ala Gln Lys Ala Gly Cys
                85                  90                  95

Thr Arg Gly Cys Leu Ile Cys Leu Ser His Ile Lys Cys Thr Ala Lys
                100                 105                 110

Met Lys Lys Trp Leu Pro Gly Arg Cys Gly Ser Trp Glu Gly Asp Lys
                115                 120                 125

Glu Thr Gly Gln Gly Gly Ile Gly Glu Ala Ile Val Asp Ile Pro Glu
    130                 135                 140

Ile Pro Gly Phe Lys Glu Leu Ala Pro Met Glu Gln Phe Ile Ala Gln
145                 150                 155                 160

Val Asp Leu Cys Ala Asp Cys Thr Thr Gly Cys Trp Lys Gly Trp Ala
                165                 170                 175

Asn Leu Lys Cys Ser Leu Leu Leu Leu Lys Trp Leu Pro Ser Arg Cys
                180                 185                 190

Ala Gly Phe Ala Asp Lys Ile Gln Ala Gln Val Asp Thr Ile Lys Gly
                195                 200                 205

Ala Gly Gly Ser
    210

<210> SEQ ID NO 48
<211> LENGTH: 212
<212> TYPE: PRT
<213> ORGANISM: Artificial Sequence
<220> FEATURE:
<223> OTHER INFORMATION: ALuc57

<400> SEQUENCE: 48

Met Met Gly Ile Lys Val Leu Phe Ala Leu Ile Cys Phe Ala Leu Val
1               5                   10                  15

Gln Ala Asn Tyr His His His His His His His Asp Ile Val Gly Val
                20                  25                  30

Glu Gly Lys Phe Gly Thr Thr Asp Leu Glu Thr Asp Leu Phe Thr Ile
            35                  40                  45

Val Glu Asp Met Asn Val Ile Ser Arg Asp Thr Asp Val Asp Ala Asn
    50                  55                  60

Arg Ala Asp Arg Gly Arg Arg Gly Lys Leu Pro Gly Lys Lys Leu Pro
65                  70                  75                  80

Leu Glu Val Leu Lys Glu Leu Glu Ala Asn Ala Gln Lys Ala Gly Cys
                85                  90                  95

Thr Arg Gly Cys Leu Ile Cys Leu Ser His Ile Lys Cys Thr Ala Lys
                100                 105                 110

Val Lys Lys Trp Leu Pro Gly Arg Cys Glu Ser Trp Glu Gly Asp Lys
                115                 120                 125

Glu Thr Gly Gln Gly Gly Ile Gly Glu Ala Ile Val Asp Ile Pro Glu
    130                 135                 140

Ile Pro Gly Phe Lys Gly Leu Ala Pro Met Glu Gln Phe Ile Ala Gln
145                 150                 155                 160

Val Asp Leu Cys Ala Asp Cys Thr Thr Gly Cys Trp Lys Gly Trp Ala
                165                 170                 175

Asn Leu Lys Cys Ser Ala Leu Leu Lys Lys Trp Leu Pro Ser Arg Cys
                180                 185                 190

Ala Gly Phe Ala Asp Lys Ile Gln Ala Gln Val Asp Thr Ile Lys Gly
        195                 200                 205

Ala Gly Gly Ser
    210

<210> SEQ ID NO 49
<211> LENGTH: 69
<212> TYPE: PRT
<213> ORGANISM: Artificial Sequence
<220> FEATURE:
<223> OTHER INFORMATION: ALuc common partial sequence

<400> SEQUENCE: 49

Met Met Gly Ile Lys Val Leu Phe Ala Leu Ile Cys Phe Ala Leu Val
1               5                   10                  15

Gln Ala Asn Pro Thr Glu Asn Lys Asp Asp Ile Asp Ile Val Gly Val
            20                  25                  30

Glu Gly Lys Phe Gly Thr Thr Asp Leu Glu Thr Asp Leu Phe Thr Ile
        35                  40                  45

Val Glu Asp Met Asn Val Ile Ser Arg Asp Thr Asp Val Asp Ala Asn
    50                  55                  60

Arg Ala Asp Arg Gly
65

<210> SEQ ID NO 50
<211> LENGTH: 149
<212> TYPE: PRT
<213> ORGANISM: Artificial Sequence
<220> FEATURE:
<223> OTHER INFORMATION: ALuc common partial sequence

<400> SEQUENCE: 50

Met Met Gly Val Lys Leu Ile Phe Ala Val Leu Cys Val Ala Val Ala
1               5                   10                  15

Gln Ala Asn Ala Thr Ile Asn Glu Asn Phe Glu Asp Ile Asp Leu Val
            20                  25                  30

Ala Ile Gly Gly Ser Phe Ala Asp Leu Glu Thr Asp Leu Phe Thr Ile
        35                  40                  45

Val Glu Asp Met Asn Val Ile Ser Arg Asp Thr Asp Val Asp Ala Asn
    50                  55                  60

Arg Gly Gly Arg Gly Arg Arg Gly Lys Leu Pro Gly Lys Lys Leu Pro
65                  70                  75                  80

Leu Glu Val Leu Lys Glu Leu Glu Ala Asn Ala Gln Lys Ala Gly Cys
            85                  90                  95

Thr Arg Gly Cys Leu Ile Cys Leu Ser His Ile Lys Cys Thr Ala Lys
            100                 105                 110

Met Lys Lys Trp Leu Pro Gly Arg Cys Glu Ser Trp Glu Gly Asp Lys
            115                 120                 125

Glu Thr Gly Gln Gly Gly Ile Gly Glu Ala Ile Val Asp Ile Pro Glu
    130                 135                 140

Ile Pro Gly Phe Lys
145

<210> SEQ ID NO 51
<211> LENGTH: 122
<212> TYPE: PRT
<213> ORGANISM: Artificial Sequence
<220> FEATURE:
<223> OTHER INFORMATION: picALuc30

```
<400> SEQUENCE: 51

Lys Leu Pro Gly Lys Lys Leu Pro Leu Glu Val Leu Lys Glu Leu Glu
1               5                   10                  15

Ala Asn Ala Gln Lys Ala Gly Cys Thr Arg Gly Cys Leu Ile Cys Leu
                20                  25                  30

Ser His Ile Lys Cys Thr Ala Lys Met Lys Lys Trp Leu Pro Gly Arg
            35                  40                  45

Cys Glu Ser Trp Glu Gly Asp Lys Glu Thr Gly Gln Gly Gly Ile Gly
        50                  55                  60

Glu Ala Ile Val Asp Ile Pro Glu Ile Pro Gly Phe Lys Glu Leu Ala
65                  70                  75                  80

Pro Met Glu Gln Phe Ile Ala Gln Val Asp Leu Cys Ala Asp Cys Thr
                85                  90                  95

Thr Gly Cys Leu Lys Gly Leu Ala Asn Val Lys Cys Ser Ala Leu Leu
            100                 105                 110

Lys Lys Trp Leu Pro Ser Arg Cys Ala Gly
            115                 120

<210> SEQ ID NO 52
<211> LENGTH: 122
<212> TYPE: PRT
<213> ORGANISM: Artificial Sequence
<220> FEATURE:
<223> OTHER INFORMATION: picALuc16

<400> SEQUENCE: 52

Lys Leu Pro Gly Lys Lys Leu Pro Leu Glu Val Leu Lys Glu Leu Glu
1               5                   10                  15

Ala Asn Ala Gln Lys Ala Gly Cys Thr Arg Gly Cys Leu Ile Cys Leu
                20                  25                  30

Ser His Ile Lys Cys Thr Ala Lys Met Lys Lys Trp Leu Pro Gly Arg
            35                  40                  45

Cys Glu Ser Trp Glu Gly Asp Lys Glu Thr Gly Gln Gly Gly Ile Gly
        50                  55                  60

Glu Ala Ile Val Asp Ile Pro Glu Ile Pro Gly Phe Lys Asp Leu Glu
65                  70                  75                  80

Pro Met Glu Gln Phe Ile Ala Gln Val Asp Leu Cys Val Asp Cys Thr
                85                  90                  95

Thr Gly Cys Leu Lys Gly Leu Ala Asn Val Lys Cys Ser Asp Leu Leu
            100                 105                 110

Lys Lys Trp Leu Pro Ser Arg Cys Ala Thr
            115                 120

<210> SEQ ID NO 53
<211> LENGTH: 125
<212> TYPE: PRT
<213> ORGANISM: Artificial Sequence
<220> FEATURE:
<223> OTHER INFORMATION: picALuc48

<400> SEQUENCE: 53

His Gly Gly Leu Pro Gly Lys Lys Met Pro Leu Glu Val Leu Leu Glu
1               5                   10                  15

Leu Glu Ala Asn Ala Gln Arg Ala Gly Cys Thr Arg Gly Cys Leu Ile
                20                  25                  30

Cys Leu Ser Lys Ile Lys Cys Thr Ala Lys Met Lys Lys Trp Leu Pro
            35                  40                  45
```

```
Gly Arg Cys Glu Ser Trp Ala Gly Asp Lys Glu Thr Gly Gln Gly Gly
    50                  55                  60

Ile Thr Glu Glu Glu Thr Val Asp Ile Pro Glu Ile Pro Gly Phe Lys
65                  70                  75                  80

Asp Leu Glu Pro Met Glu Gln Phe Ile Ala Gln Val Asp Leu Cys Val
                85                  90                  95

Asp Cys Thr Thr Gly Cys Leu Lys Gly Leu Ala Asn Val Lys Cys Ser
                100                 105                 110

Asp Leu Leu Lys Lys Trp Leu Pro Ser Arg Cys Ala Thr
            115                 120                 125
```

<210> SEQ ID NO 54
<211> LENGTH: 140
<212> TYPE: PRT
<213> ORGANISM: Artificial Sequence
<220> FEATURE:
<223> OTHER INFORMATION: ALuc30_del_loop2N1

<400> SEQUENCE: 54

```
Arg Gly Arg Arg Gly Lys Leu Pro Gly Lys Lys Leu Pro Leu Glu Val
1                   5                   10                  15

Leu Lys Glu Leu Glu Ala Asn Ala Gln Lys Ala Gly Cys Thr Arg Gly
                20                  25                  30

Cys Leu Ile Cys Leu Ser His Ile Lys Cys Thr Ala Lys Met Lys Lys
            35                  40                  45

Trp Leu Pro Gly Arg Cys Glu Ser Trp Glu Gly Asp Lys Glu Thr Gly
    50                  55                  60

Gln Gly Gly Ile Gly Glu Ala Ile Val Gly Ser Phe Lys Glu Leu Ala
65                  70                  75                  80

Pro Met Glu Gln Phe Ile Ala Gln Val Asp Leu Cys Ala Asp Cys Thr
                85                  90                  95

Thr Gly Cys Leu Lys Gly Leu Ala Asn Val Lys Cys Ser Ala Leu Leu
                100                 105                 110

Lys Lys Trp Leu Pro Ser Arg Cys Ala Gly Phe Ala Asp Lys Ile Gln
            115                 120                 125

Ala Gln Val Asp Thr Ile Lys Gly Ala Gly Gly Ser
    130                 135                 140
```

<210> SEQ ID NO 55
<211> LENGTH: 140
<212> TYPE: PRT
<213> ORGANISM: Artificial Sequence
<220> FEATURE:
<223> OTHER INFORMATION: ALuc16_del_loop2N1

<400> SEQUENCE: 55

```
Arg Gly Arg Arg Gly Lys Leu Pro Gly Lys Lys Leu Pro Leu Glu Val
1                   5                   10                  15

Leu Lys Glu Leu Glu Ala Asn Ala Gln Lys Ala Gly Cys Thr Arg Gly
                20                  25                  30

Cys Leu Ile Cys Leu Ser His Ile Lys Cys Thr Ala Lys Met Lys Lys
            35                  40                  45

Trp Leu Pro Gly Arg Cys Glu Ser Trp Glu Gly Asp Lys Glu Thr Gly
    50                  55                  60

Gln Gly Gly Ile Gly Glu Ala Ile Val Gly Ser Phe Lys Asp Leu Glu
65                  70                  75                  80

Pro Met Glu Gln Phe Ile Ala Gln Val Asp Leu Cys Val Asp Cys Thr
                85                  90                  95
```

```
Thr Gly Cys Leu Lys Gly Leu Ala Asn Val Lys Cys Ser Asp Leu Leu
            100                 105                 110

Lys Lys Trp Leu Pro Ser Arg Cys Ala Thr Phe Ala Ser Lys Ile Gln
        115                 120                 125

Ala Gln Val Asp Lys Ile Lys Gly Ala Gly Gly Ser
    130                 135                 140

<210> SEQ ID NO 56
<211> LENGTH: 143
<212> TYPE: PRT
<213> ORGANISM: Artificial Sequence
<220> FEATURE:
<223> OTHER INFORMATION: ALuc48_del_loop2N1

<400> SEQUENCE: 56

Arg Gly Arg Arg Gly His Gly Gly Leu Pro Gly Lys Lys Met Pro Leu
1               5                   10                  15

Glu Val Leu Leu Glu Leu Glu Ala Asn Ala Gln Arg Ala Gly Cys Thr
            20                  25                  30

Arg Gly Cys Leu Ile Cys Leu Ser Lys Ile Lys Cys Thr Ala Lys Met
        35                  40                  45

Lys Lys Trp Leu Pro Gly Arg Cys Glu Ser Trp Ala Gly Asp Lys Glu
    50                  55                  60

Thr Gly Gln Gly Gly Ile Thr Glu Glu Glu Thr Val Gly Ser Phe Lys
65                  70                  75                  80

Asp Leu Glu Pro Met Glu Gln Phe Ile Ala Gln Val Asp Leu Cys Val
                85                  90                  95

Asp Cys Thr Thr Gly Cys Leu Lys Gly Leu Ala Asn Val Lys Cys Ser
            100                 105                 110

Asp Leu Leu Lys Lys Trp Leu Pro Ser Arg Cys Ala Thr Phe Ala Ser
        115                 120                 125

Lys Ile Gln Ala Gln Val Asp Lys Ile Lys Gly Ala Gly Gly Ser
    130                 135                 140

<210> SEQ ID NO 57
<211> LENGTH: 123
<212> TYPE: PRT
<213> ORGANISM: Artificial Sequence
<220> FEATURE:
<223> OTHER INFORMATION: Met_picALuc30

<400> SEQUENCE: 57

Met Lys Leu Pro Gly Lys Lys Leu Pro Leu Glu Val Leu Lys Glu Leu
1               5                   10                  15

Glu Ala Asn Ala Gln Lys Ala Gly Cys Thr Arg Gly Cys Leu Ile Cys
            20                  25                  30

Leu Ser His Ile Lys Cys Thr Ala Lys Met Lys Lys Trp Leu Pro Gly
        35                  40                  45

Arg Cys Glu Ser Trp Glu Gly Asp Lys Glu Thr Gly Gln Gly Gly Ile
    50                  55                  60

Gly Glu Ala Ile Val Asp Ile Pro Glu Ile Pro Gly Phe Lys Glu Leu
65                  70                  75                  80

Ala Pro Met Glu Gln Phe Ile Ala Gln Val Asp Leu Cys Ala Asp Cys
                85                  90                  95

Thr Thr Gly Cys Leu Lys Gly Leu Ala Asn Val Lys Cys Ser Ala Leu
            100                 105                 110

Leu Lys Lys Trp Leu Pro Ser Arg Cys Ala Gly
```

-continued

```
          115                   120

<210> SEQ ID NO 58
<211> LENGTH: 123
<212> TYPE: PRT
<213> ORGANISM: Artificial Sequence
<220> FEATURE:
<223> OTHER INFORMATION: Met_picALuc16

<400> SEQUENCE: 58

Met Lys Leu Pro Gly Lys Lys Leu Pro Leu Glu Val Leu Lys Glu Leu
1               5                   10                  15

Glu Ala Asn Ala Gln Lys Ala Gly Cys Thr Arg Gly Cys Leu Ile Cys
            20                  25                  30

Leu Ser His Ile Lys Cys Thr Ala Lys Met Lys Lys Trp Leu Pro Gly
        35                  40                  45

Arg Cys Glu Ser Trp Glu Gly Asp Lys Glu Thr Gly Gln Gly Gly Ile
    50                  55                  60

Gly Glu Ala Ile Val Asp Ile Pro Glu Ile Pro Gly Phe Lys Asp Leu
65                  70                  75                  80

Glu Pro Met Glu Gln Phe Ile Ala Gln Val Asp Leu Cys Val Asp Cys
                85                  90                  95

Thr Thr Gly Cys Leu Lys Gly Leu Ala Asn Val Lys Cys Ser Asp Leu
            100                 105                 110

Leu Lys Lys Trp Leu Pro Ser Arg Cys Ala Thr
            115                 120

<210> SEQ ID NO 59
<211> LENGTH: 126
<212> TYPE: PRT
<213> ORGANISM: Artificial Sequence
<220> FEATURE:
<223> OTHER INFORMATION: Met_picALuc48

<400> SEQUENCE: 59

Met His Gly Gly Leu Pro Gly Lys Lys Met Pro Leu Glu Val Leu Leu
1               5                   10                  15

Glu Leu Glu Ala Asn Ala Gln Arg Ala Gly Cys Thr Arg Gly Cys Leu
            20                  25                  30

Ile Cys Leu Ser Lys Ile Lys Cys Thr Ala Lys Met Lys Lys Trp Leu
        35                  40                  45

Pro Gly Arg Cys Glu Ser Trp Ala Gly Asp Lys Glu Thr Gly Gln Gly
    50                  55                  60

Gly Ile Thr Glu Glu Glu Thr Val Asp Ile Pro Glu Ile Pro Gly Phe
65                  70                  75                  80

Lys Asp Leu Glu Pro Met Glu Gln Phe Ile Ala Gln Val Asp Leu Cys
                85                  90                  95

Val Asp Cys Thr Thr Gly Cys Leu Lys Gly Leu Ala Asn Val Lys Cys
            100                 105                 110

Ser Asp Leu Leu Lys Lys Trp Leu Pro Ser Arg Cys Ala Thr
            115                 120                 125

<210> SEQ ID NO 60
<211> LENGTH: 141
<212> TYPE: PRT
<213> ORGANISM: Artificial Sequence
<220> FEATURE:
<223> OTHER INFORMATION: Met_ALuc30_del_loop2N1

<400> SEQUENCE: 60
```

-continued

```
Met Arg Gly Arg Arg Gly Lys Leu Pro Gly Lys Lys Leu Pro Leu Glu
1               5                   10                  15

Val Leu Lys Glu Leu Glu Ala Asn Ala Gln Lys Ala Gly Cys Thr Arg
            20                  25                  30

Gly Cys Leu Ile Cys Leu Ser His Ile Lys Cys Thr Ala Lys Met Lys
        35                  40                  45

Lys Trp Leu Pro Gly Arg Cys Glu Ser Trp Glu Gly Asp Lys Glu Thr
    50                  55                  60

Gly Gln Gly Gly Ile Gly Glu Ala Ile Val Gly Ser Phe Lys Glu Leu
65                  70                  75                  80

Ala Pro Met Glu Gln Phe Ile Ala Gln Val Asp Leu Cys Ala Asp Cys
                85                  90                  95

Thr Thr Gly Cys Leu Lys Gly Leu Ala Asn Val Lys Cys Ser Ala Leu
            100                 105                 110

Leu Lys Lys Trp Leu Pro Ser Arg Cys Ala Gly Phe Ala Asp Lys Ile
        115                 120                 125

Gln Ala Gln Val Asp Thr Ile Lys Gly Ala Gly Gly Ser
    130                 135                 140
```

<210> SEQ ID NO 61
<211> LENGTH: 141
<212> TYPE: PRT
<213> ORGANISM: Artificial Sequence
<220> FEATURE:
<223> OTHER INFORMATION: Met_ALuc16_del_loop2N1

<400> SEQUENCE: 61

```
Met Arg Gly Arg Arg Gly Lys Leu Pro Gly Lys Lys Leu Pro Leu Glu
1               5                   10                  15

Val Leu Lys Glu Leu Glu Ala Asn Ala Gln Lys Ala Gly Cys Thr Arg
            20                  25                  30

Gly Cys Leu Ile Cys Leu Ser His Ile Lys Cys Thr Ala Lys Met Lys
        35                  40                  45

Lys Trp Leu Pro Gly Arg Cys Glu Ser Trp Glu Gly Asp Lys Glu Thr
    50                  55                  60

Gly Gln Gly Gly Ile Gly Glu Ala Ile Val Gly Ser Phe Lys Asp Leu
65                  70                  75                  80

Glu Pro Met Glu Gln Phe Ile Ala Gln Val Asp Leu Cys Val Asp Cys
                85                  90                  95

Thr Thr Gly Cys Leu Lys Gly Leu Ala Asn Val Lys Cys Ser Asp Leu
            100                 105                 110

Leu Lys Lys Trp Leu Pro Ser Arg Cys Ala Thr Phe Ala Ser Lys Ile
        115                 120                 125

Gln Ala Gln Val Asp Lys Ile Lys Gly Ala Gly Gly Ser
    130                 135                 140
```

<210> SEQ ID NO 62
<211> LENGTH: 144
<212> TYPE: PRT
<213> ORGANISM: Artificial Sequence
<220> FEATURE:
<223> OTHER INFORMATION: Met_ALuc48_del_loop2N1

<400> SEQUENCE: 62

```
Met Arg Gly Arg Arg Gly His Gly Gly Leu Pro Gly Lys Lys Met Pro
1               5                   10                  15

Leu Glu Val Leu Leu Glu Leu Glu Ala Asn Ala Gln Arg Ala Gly Cys
```

-continued

```
                20              25              30

Thr Arg Gly Cys Leu Ile Cys Leu Ser Lys Ile Lys Cys Thr Ala Lys
        35              40              45

Met Lys Lys Trp Leu Pro Gly Arg Cys Glu Ser Trp Ala Gly Asp Lys
    50              55              60

Glu Thr Gly Gln Gly Gly Ile Thr Glu Glu Glu Thr Val Gly Ser Phe
65              70              75              80

Lys Asp Leu Glu Pro Met Glu Gln Phe Ile Ala Gln Val Asp Leu Cys
            85              90              95

Val Asp Cys Thr Thr Gly Cys Leu Lys Gly Leu Ala Asn Val Lys Cys
            100             105             110

Ser Asp Leu Leu Lys Lys Trp Leu Pro Ser Arg Cys Ala Thr Phe Ala
        115             120             125

Ser Lys Ile Gln Ala Gln Val Asp Lys Ile Lys Gly Ala Gly Gly Ser
    130             135             140
```

<210> SEQ ID NO 63
<211> LENGTH: 11
<212> TYPE: PRT
<213> ORGANISM: Artificial Sequence
<220> FEATURE:
<223> OTHER INFORMATION: Membrane localization signal

<400> SEQUENCE: 63

```
Met Leu Cys Cys Met Arg Arg Thr Lys Gln Val
1               5               10
```

<210> SEQ ID NO 64
<211> LENGTH: 10
<212> TYPE: PRT
<213> ORGANISM: Artificial Sequence
<220> FEATURE:
<223> OTHER INFORMATION: Cytoplasmic localization signal

<400> SEQUENCE: 64

```
Gly Arg Lys Lys Arg Arg Gln Arg Arg Arg
1               5               10
```

<210> SEQ ID NO 65
<211> LENGTH: 4
<212> TYPE: PRT
<213> ORGANISM: Artificial Sequence
<220> FEATURE:
<223> OTHER INFORMATION: Endoplasmic reticulum (ER) localization signal

<400> SEQUENCE: 65

```
Lys Asp Glu Leu
1
```

<210> SEQ ID NO 66
<211> LENGTH: 8
<212> TYPE: PRT
<213> ORGANISM: Artificial Sequence
<220> FEATURE:
<223> OTHER INFORMATION: Nuclear localization signal (NLS)

<400> SEQUENCE: 66

```
Asp Pro Lys Lys Lys Arg Lys Val
1               5
```

<210> SEQ ID NO 67
<211> LENGTH: 6
<212> TYPE: PRT

```
<213> ORGANISM: Artificial Sequence
<220> FEATURE:
<223> OTHER INFORMATION: His-Tag

<400> SEQUENCE: 67

His His His His His His
1               5

<210> SEQ ID NO 68
<211> LENGTH: 8
<212> TYPE: PRT
<213> ORGANISM: Artificial Sequence
<220> FEATURE:
<223> OTHER INFORMATION: FLAG-tag

<400> SEQUENCE: 68

Asp Tyr Lys Asp Asp Asp Asp Lys
1               5

<210> SEQ ID NO 69
<211> LENGTH: 10
<212> TYPE: PRT
<213> ORGANISM: Artificial Sequence
<220> FEATURE:
<223> OTHER INFORMATION: Myc-tag

<400> SEQUENCE: 69

Glu Gln Lys Leu Ile Ser Glu Glu Asp Leu
1               5               10

<210> SEQ ID NO 70
<211> LENGTH: 9
<212> TYPE: PRT
<213> ORGANISM: Artificial Sequence
<220> FEATURE:
<223> OTHER INFORMATION: HA-tag

<400> SEQUENCE: 70

Tyr Pro Tyr Asp Val Pro Asp Tyr Ala
1               5

<210> SEQ ID NO 71
<211> LENGTH: 14
<212> TYPE: PRT
<213> ORGANISM: Artificial Sequence
<220> FEATURE:
<223> OTHER INFORMATION: V5-tag

<400> SEQUENCE: 71

Gly Lys Pro Ile Pro Asn Pro Leu Leu Gly Leu Asp Ser Thr
1               5               10

<210> SEQ ID NO 72
<211> LENGTH: 11
<212> TYPE: PRT
<213> ORGANISM: Artificial Sequence
<220> FEATURE:
<223> OTHER INFORMATION: T7-tag

<400> SEQUENCE: 72

Met Ala Ser Met Thr Gly Gly Gln Gln Met Gly
1               5               10

<210> SEQ ID NO 73
<211> LENGTH: 171
<212> TYPE: PRT
<213> ORGANISM: oplophorus gracilirostris
```

-continued

<400> SEQUENCE: 73

Ala Val Phe Thr Leu Glu Asp Phe Val Gly Asp Trp Arg Gln Thr Ala
1               5                   10                  15

Gly Tyr Asn Leu Asp Gln Val Leu Glu Gln Gly Gly Val Ser Ser Leu
                20                  25                  30

Phe Gln Asn Leu Gly Val Ser Val Thr Pro Ile Gln Arg Ile Val Leu
            35                  40                  45

Ser Gly Glu Asn Gly Leu Lys Ile Asp Ile His Val Ile Ile Pro Tyr
        50                  55                  60

Glu Gly Leu Ser Gly Asp Gln Met Gly Gln Ile Glu Lys Ile Phe Lys
65                  70                  75                  80

Val Val Tyr Pro Val Asp Asp His His Phe Lys Val Ile Leu His Tyr
                85                  90                  95

Gly Thr Leu Val Ile Asp Gly Val Thr Pro Asn Met Ile Asp Tyr Phe
            100                 105                 110

Gly Arg Pro Tyr Glu Gly Ile Ala Val Phe Asp Gly Lys Lys Ile Thr
            115                 120                 125

Val Thr Gly Thr Leu Trp Asn Gly Asn Lys Ile Ile Asp Glu Arg Leu
        130                 135                 140

Ile Asn Pro Asp Gly Ser Leu Leu Phe Arg Val Thr Ile Asn Gly Val
145                 150                 155                 160

Thr Gly Trp Arg Leu Cys Glu Arg Ile Leu Ala
                165                 170

<210> SEQ ID NO 74
<211> LENGTH: 148
<212> TYPE: PRT
<213> ORGANISM: Metrisia longa

<400> SEQUENCE: 74

Met Glu Ala Glu Ala Glu Arg Gly Lys Leu Pro Gly Lys Lys Leu Pro
1               5                   10                  15

Leu Glu Val Leu Ile Glu Leu Glu Ala Asn Ala Arg Lys Ala Gly Cys
                20                  25                  30

Thr Arg Gly Cys Leu Ile Cys Leu Ser Lys Ile Lys Cys Thr Ala Lys
            35                  40                  45

Met Lys Lys Tyr Ile Pro Gly Arg Cys Ala Asp Tyr Gly Gly Asp Lys
        50                  55                  60

Lys Thr Gly Gln Ala Gly Ile Val Gly Ala Ile Val Asp Ile Pro Glu
65                  70                  75                  80

Ile Ser Gly Phe Lys Glu Met Glu Pro Met Glu Gln Phe Ile Ala Gln
                85                  90                  95

Val Asp Arg Cys Ala Asp Cys Thr Thr Gly Cys Leu Lys Gly Leu Ala
            100                 105                 110

Asn Val Lys Cys Ser Asp Leu Leu Lys Lys Trp Leu Pro Gly Arg Cys
            115                 120                 125

Ala Thr Phe Ala Asp Lys Ile Gln Ser Glu Val Asp Asn Ile Lys Gly
        130                 135                 140

Leu Ala Gly Asp
145

<210> SEQ ID NO 75
<211> LENGTH: 185
<212> TYPE: PRT
<213> ORGANISM: Gaussia princeps

<400> SEQUENCE: 75

```
Met Gly Val Lys Val Leu Phe Ala Leu Ile Cys Ile Ala Val Ala Glu
1               5                   10                  15

Ala Lys Pro Thr Glu Asn Asn Glu Asp Phe Asn Ile Val Ala Val Ala
            20                  25                  30

Ser Asn Phe Ala Thr Thr Asp Leu Asp Ala Asp Arg Gly Lys Leu Pro
        35                  40                  45

Gly Lys Lys Leu Pro Leu Glu Val Leu Lys Glu Met Glu Ala Asn Ala
    50                  55                  60

Arg Lys Ala Gly Cys Thr Arg Gly Cys Leu Ile Cys Leu Ser His Ile
65                  70                  75                  80

Lys Cys Thr Pro Lys Met Lys Lys Phe Ile Pro Gly Arg Cys His Thr
                85                  90                  95

Tyr Glu Gly Asp Lys Glu Ser Ala Gln Gly Gly Ile Gly Glu Ala Ile
            100                 105                 110

Val Asp Ile Pro Glu Ile Pro Gly Phe Lys Asp Leu Glu Pro Met Glu
            115                 120                 125

Gln Phe Ile Ala Gln Val Asp Leu Cys Val Asp Cys Thr Thr Gly Cys
    130                 135                 140

Leu Lys Gly Leu Ala Asn Val Gln Cys Ser Asp Leu Leu Lys Lys Trp
145                 150                 155                 160

Leu Pro Gln Arg Cys Ala Thr Phe Ala Ser Lys Ile Gln Gly Gln Val
                165                 170                 175

Asp Lys Ile Lys Gly Ala Gly Gly Asp
            180                 185
```

<210> SEQ ID NO 76
<211> LENGTH: 74
<212> TYPE: PRT
<213> ORGANISM: Artificial Sequence
<220> FEATURE:
<223> OTHER INFORMATION: part of picALuc30

<400> SEQUENCE: 76

```
Gly Lys Lys Leu Pro Leu Glu Val Leu Lys Glu Leu Glu Ala Asn Ala
1               5                   10                  15

Gln Lys Ala Gly Cys Thr Arg Gly Cys Leu Ile Cys Leu Ser His Ile
            20                  25                  30

Lys Cys Thr Ala Lys Met Lys Lys Trp Leu Pro Gly Arg Cys Glu Ser
        35                  40                  45

Trp Glu Gly Asp Lys Glu Thr Gly Gln Gly Gly Ile Gly Glu Ala Ile
    50                  55                  60

Val Asp Ile Pro Glu Ile Pro Gly Phe Lys
65                  70
```

<210> SEQ ID NO 77
<211> LENGTH: 19
<212> TYPE: PRT
<213> ORGANISM: Artificial Sequence
<220> FEATURE:
<223> OTHER INFORMATION: part of picALuc30

<400> SEQUENCE: 77

```
Gly Lys Lys Leu Pro Leu Glu Val Leu Lys Glu Leu Glu Ala Asn Ala
1               5                   10                  15

Gln Lys Ala
```

-continued

```
<210> SEQ ID NO 78
<211> LENGTH: 55
<212> TYPE: PRT
<213> ORGANISM: Artificial Sequence
<220> FEATURE:
<223> OTHER INFORMATION: part of picALuc30

<400> SEQUENCE: 78

Gly Lys Lys Leu Pro Leu Glu Val Leu Lys Glu Leu Glu Ala Asn Ala
1               5                   10                  15

Gln Lys Ala Gly Cys Thr Arg Gly Cys Leu Ile Cys Leu Ser His Ile
            20                  25                  30

Lys Cys Thr Ala Lys Met Lys Lys Trp Leu Pro Gly Arg Cys Glu Ser
        35                  40                  45

Trp Glu Gly Asp Lys Glu Thr
    50                  55

<210> SEQ ID NO 79
<211> LENGTH: 61
<212> TYPE: PRT
<213> ORGANISM: Artificial Sequence
<220> FEATURE:
<223> OTHER INFORMATION: part of picALuc30

<400> SEQUENCE: 79

Gly Lys Lys Leu Pro Leu Glu Val Leu Lys Glu Leu Glu Ala Asn Ala
1               5                   10                  15

Gln Lys Ala Gly Cys Thr Arg Gly Cys Leu Ile Cys Leu Ser His Ile
            20                  25                  30

Lys Cys Thr Ala Lys Met Lys Lys Trp Leu Pro Gly Arg Cys Glu Ser
        35                  40                  45

Trp Glu Gly Asp Lys Glu Thr Gly Gln Gly Gly Ile Gly
    50                  55                  60

<210> SEQ ID NO 80
<211> LENGTH: 69
<212> TYPE: PRT
<213> ORGANISM: Artificial Sequence
<220> FEATURE:
<223> OTHER INFORMATION: part of picALuc30

<400> SEQUENCE: 80

Gly Lys Lys Leu Pro Leu Glu Val Leu Lys Glu Leu Glu Ala Asn Ala
1               5                   10                  15

Gln Lys Ala Gly Cys Thr Arg Gly Cys Leu Ile Cys Leu Ser His Ile
            20                  25                  30

Lys Cys Thr Ala Lys Met Lys Lys Trp Leu Pro Gly Arg Cys Glu Ser
        35                  40                  45

Trp Glu Gly Asp Lys Glu Thr Gly Gln Gly Gly Ile Gly Glu Ala Ile
    50                  55                  60

Val Asp Ile Pro Glu
65

<210> SEQ ID NO 81
<211> LENGTH: 98
<212> TYPE: PRT
<213> ORGANISM: Artificial Sequence
<220> FEATURE:
<223> OTHER INFORMATION: part of picALuc30

<400> SEQUENCE: 81
```

-continued

```
Gly Cys Thr Arg Gly Cys Leu Ile Cys Leu Ser His Ile Lys Cys Thr
1               5                   10                  15

Ala Lys Met Lys Lys Trp Leu Pro Gly Arg Cys Glu Ser Trp Glu Gly
            20                  25                  30

Asp Lys Glu Thr Gly Gln Gly Gly Ile Gly Glu Ala Ile Val Asp Ile
        35                  40                  45

Pro Glu Ile Pro Gly Phe Lys Glu Leu Ala Pro Met Glu Gln Phe Ile
    50                  55                  60

Ala Gln Val Asp Leu Cys Ala Asp Cys Thr Thr Gly Cys Leu Lys Gly
65                  70                  75                  80

Leu Ala Asn Val Lys Cys Ser Ala Leu Leu Lys Lys Trp Leu Pro Ser
                85                  90                  95

Arg Cys
```

```
<210> SEQ ID NO 82
<211> LENGTH: 43
<212> TYPE: PRT
<213> ORGANISM: Artificial Sequence
<220> FEATURE:
<223> OTHER INFORMATION: part of picALuc30

<400> SEQUENCE: 82
```

```
Glu Leu Ala Pro Met Glu Gln Phe Ile Ala Gln Val Asp Leu Cys Ala
1               5                   10                  15

Asp Cys Thr Thr Gly Cys Leu Lys Gly Leu Ala Asn Val Lys Cys Ser
            20                  25                  30

Ala Leu Leu Lys Lys Trp Leu Pro Ser Arg Cys
        35                  40
```

```
<210> SEQ ID NO 83
<211> LENGTH: 56
<212> TYPE: PRT
<213> ORGANISM: Artificial Sequence
<220> FEATURE:
<223> OTHER INFORMATION: part of picALuc30

<400> SEQUENCE: 83
```

```
Glu Ala Ile Val Asp Ile Pro Glu Ile Pro Gly Phe Lys Glu Leu Ala
1               5                   10                  15

Pro Met Glu Gln Phe Ile Ala Gln Val Asp Leu Cys Ala Asp Cys Thr
            20                  25                  30

Thr Gly Cys Leu Lys Gly Leu Ala Asn Val Lys Cys Ser Ala Leu Leu
        35                  40                  45

Lys Lys Trp Leu Pro Ser Arg Cys
    50                  55
```

```
<210> SEQ ID NO 84
<211> LENGTH: 48
<212> TYPE: PRT
<213> ORGANISM: Artificial Sequence
<220> FEATURE:
<223> OTHER INFORMATION: part of picALuc30

<400> SEQUENCE: 84
```

```
Ile Pro Gly Phe Lys Glu Leu Ala Pro Met Glu Gln Phe Ile Ala Gln
1               5                   10                  15

Val Asp Leu Cys Ala Asp Cys Thr Thr Gly Cys Leu Lys Gly Leu Ala
            20                  25                  30

Asn Val Lys Cys Ser Ala Leu Leu Lys Lys Trp Leu Pro Ser Arg Cys
        35                  40                  45
```

```
<210> SEQ ID NO 85
<211> LENGTH: 17
<212> TYPE: PRT
<213> ORGANISM: Artificial Sequence
<220> FEATURE:
<223> OTHER INFORMATION: part of picALuc30

<400> SEQUENCE: 85

Ala Asn Val Lys Cys Ser Ala Leu Leu Lys Lys Trp Leu Pro Ser Arg
1               5                   10                  15

Cys

<210> SEQ ID NO 86
<211> LENGTH: 23
<212> TYPE: PRT
<213> ORGANISM: Artificial Sequence
<220> FEATURE:
<223> OTHER INFORMATION: linker

<400> SEQUENCE: 86

Gly Gly Gly Gly Ser Gly Gly Gly Ser Gly Gly Gly Ser Gly
1               5                   10                  15

Gly Gly Gly Ser Ser Gly Arg
            20

<210> SEQ ID NO 87
<211> LENGTH: 4
<212> TYPE: PRT
<213> ORGANISM: Artificial Sequence
<220> FEATURE:
<223> OTHER INFORMATION: linker

<400> SEQUENCE: 87

Gly Gly Gly Gly
1

<210> SEQ ID NO 88
<211> LENGTH: 107
<212> TYPE: PRT
<213> ORGANISM: Artificial Sequence
<220> FEATURE:
<223> OTHER INFORMATION: FKBP

<400> SEQUENCE: 88

Met Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Phe Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Glu
            100                 105

<210> SEQ ID NO 89
<211> LENGTH: 91
```

-continued

```
<212> TYPE: PRT
<213> ORGANISM: Artificial Sequence
<220> FEATURE:
<223> OTHER INFORMATION: FRB

<400> SEQUENCE: 89

Met Glu Met Trp His Glu Gly Leu Glu Glu Ala Ser Arg Leu Tyr Phe
1               5                   10                  15

Gly Glu Arg Asn Val Lys Gly Met Phe Glu Val Leu Glu Pro Leu His
            20                  25                  30

Ala Met Met Glu Arg Gly Pro Gln Thr Leu Lys Glu Thr Ser Phe Asn
        35                  40                  45

Gln Ala Tyr Gly Arg Asp Leu Met Glu Ala Gln Glu Trp Cys Arg Lys
    50                  55                  60

Tyr Met Lys Ser Gly Asn Val Lys Asp Leu Thr Gln Ala Trp Asp Leu
65                  70                  75                  80

Tyr Tyr His Val Phe Arg Arg Ile Ser Lys Gln
                85                  90

<210> SEQ ID NO 90
<211> LENGTH: 4
<212> TYPE: PRT
<213> ORGANISM: Artificial Sequence
<220> FEATURE:
<223> OTHER INFORMATION: Synthetic construct

<400> SEQUENCE: 90

Asp Glu Val Asp
1

<210> SEQ ID NO 91
<211> LENGTH: 4
<212> TYPE: PRT
<213> ORGANISM: Artificial Sequence
<220> FEATURE:
<223> OTHER INFORMATION: Synthetic construct

<400> SEQUENCE: 91

Ile Glu Thr Asp
1
```

REAGENT KIT CONTAINING POLYPEPTIDE FOR USE IN DETECTION OF INTERMOLECULAR INTERACTIONS

BACKGROUND OF THE INVENTION

Field of the Invention

The present invention relates to a reagent kit containing a polypeptide for use in detection of intermolecular interactions.

Description of the Background Art

In the basic biology field, diagnostic techniques, and testing techniques, luciferases are used as a reporter protein for detecting a target protein. As a reporter protein, luciferases as well as fluorescent proteins, fluorescent dyes, quantum dot, peroxidase, and the like are widely used. Fluorescent proteins, fluorescent dyes, and quantum dot have high fluorescence intensity but require excitation light, so they have drawbacks including the following: (1) they are phototoxic to cells; (2) the excitation light spectrum overlaps the fluorescence spectrum and therefore the signal-background ratio tends to be low, rendering them unsuitable for small amount detection; and (3) the detector needs to be equipped with a built-in excitation light irradiator and a built-in spectral filter. Luciferase does not require excitation light, and therefore it has none of the above-described drawbacks. Moreover, generally, detection with luciferase is more suitable for small amount detection than colorimetric methods which employ peroxidase and the like.

Luciferases that have been reported so far include wild-type firefly-derived luciferase (FLuc), NanoLuc® (luciferase), TurboLuc™ (luciferase), luciferase derived from copepod (*Gaussia princeps*) (GLuc), luciferase derived from sea pansy (*Renilla reniformis*), and luciferase derived from copepod (*Metridia longa*) (MLuc). Japanese Patent Laying-Open No. 2014-100137 and International Patent Laying-Open No. WO 2017/057752 disclose an artificial luciferase (Aluc) engineered by selecting frequent amino acids from the amino acid sequence of a copepod-derived luciferase.

A luciferase can be divided for use as a probe for detecting intermolecular interactions. For example, in protein-fragment complementation assay (PCA), divided luciferase portions can be attached to molecules that are to be detected its interactions, and, by means of the resulting luminescence signal, intermolecular interactions can be detected. Japanese Patent Laying-Open No. 2014-100137, International Patent Laying-Open No. WO 2017/057752, and Remy and Michnick, Nat Methods. 2006 December; 3 (12): 977-9 disclose a probe for use to detect intermolecular interactions.

SUMMARY OF THE INVENTION

Technical Problem

When intermolecular interaction analysis is attempted, and if the probe is large, the fusion protein composed of the probe and the target protein may not be expressed in a normal fashion in a cell or steric hindrance may occur to inhibit normal functioning of the target protein.

A small probe is useful for intermolecular interaction analysis. An object of the present invention is to provide a probe with a small molecular weight usable for detecting intermolecular interactions.

Solution to Problem

The present invention relates to a reagent kit comprising:
a first polypeptide including a part in any one of amino acid sequences (A) to (C); and
a second polypeptide including a part in any one of amino acid sequences (A) to (C), which are consistent of different sequences from a sequence of the first polypeptide, and exhibiting luciferase activity when in close proximity to the first polypeptide;
(A) an amino acid sequence in SEQ ID NO: 1 with deletion of an amino acid sequence from position 1 to 69 and an amino acid sequence from position 204 to 221,
(B) an amino acid sequence in SEQ ID NO: 1 with deletion of an amino acid sequence from position 1 to 69 and deletion or substitution of at least one of amino acid residues at positions 146 to 156,
(C) the amino acid sequence (A) or (B) with further deletion of at least one of amino acid residues at positions 70 to 74.
The present invention also relates to
a first polypeptide including a part in any one of amino acid sequences (A) to (C), wherein the first polypeptide:
exhibits luciferase activity when in close proximity to a second polypeptide including a part in any one of amino acid sequences (A) to (C); and
has a sequence different from the second polypeptide:
(A) an amino acid sequence in SEQ ID NO: 1 with deletion of an amino acid sequence from position 1 to 69 and an amino acid sequence from position 204 to 221,
(B) an amino acid sequence in SEQ ID NO: 1 with deletion of an amino acid sequence from position 1 to 69 and deletion or substitution of at least one of amino acid residues at positions 146 to 156,
(C) the amino acid sequence (A) or (B) with further deletion of at least one of amino acid residues at positions 70 to 74.

Advantageous Effects of Invention

The present invention makes it possible to detect intermolecular interactions by using a novel probe with a small molecular weight.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 1 shows an example of luminescence emitted when a first polypeptide and a second polypeptide are in close proximity to each other.

FIG. 2 is a schematic view illustrating an example of detection of intermolecular interactions with the use of a first polypeptide and a second polypeptide.

FIG. 5 shows amino acid sequence identity between picALuc30 (SEQ ID NO:51) and picALuc16 (SEQ ID NO:52).

FIG. 6 shows amino acid sequence identity between picALuc30 (SEQ ID NO:51) and picALuc48 (SEQ ID NO:53).

FIG. 7 shows amino acid sequence identity between picALuc48 (SEQ ID NO:53) and picALuc16 (SEQ ID NO:52).

FIG. 11 is a graph showing the emission values obtained when coelenterazine (0.5 μM) was used as a substrate in Experiment 5.

FIG. 12 is a graph showing the emission values obtained when coelenterazine (5 μM) was used as a substrate in Experiment 5.

FIG. 13 is a graph showing the emission values obtained when coelenterazine h (5 μM) was used as a substrate in Experiment 5.

FIG. 14 is a graph showing the emission values obtained when coelenterazine h (25 μM) was used as a substrate in Experiment 5.

FIG. 15 is a graph showing the emission values obtained when furimazine was used as a substrate in Experiment 5.

FIG. 16 is a graph showing the emission values obtained when furimazine was used as a substrate in Experiment 5.

FIG. 21 shows emission spectra obtained when coelenterazine h was used as a substrate in Experiment 8.

FIG. 22 is a graph of the post-heat-treatment emission value of secretion-expressed picALuc in Experiment 9.

Figure 24:
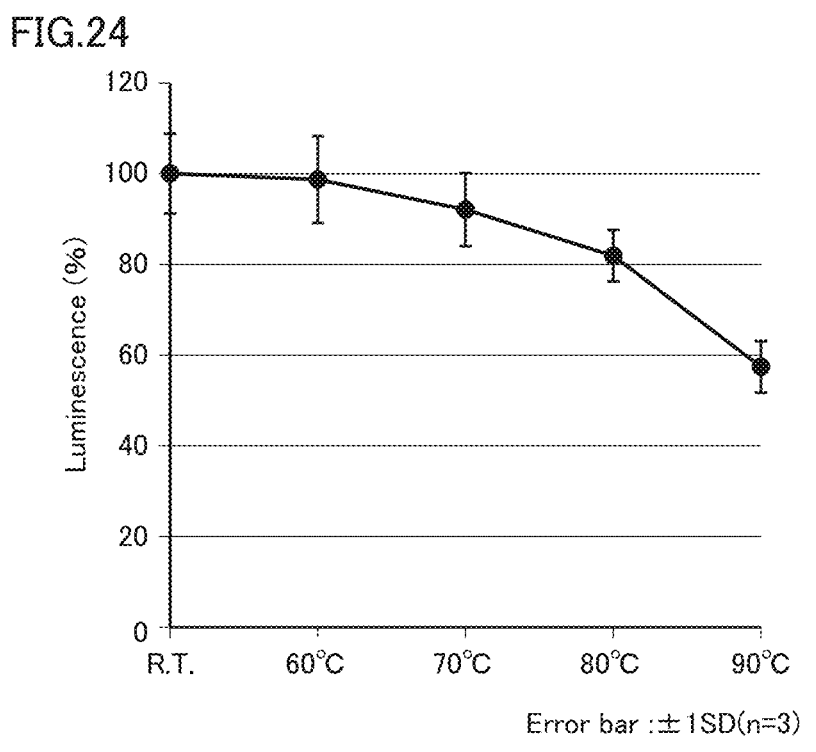

FIG. 24 is a graph of the post-heat-treatment emission value of picALuc that was expressed in Escherichia coli in Experiment 10.

FIG. 26 is a graph showing the emission values of divided picALuc and combinations thereof in Experiment 11-2.

FIG. 34 is a graph showing results of detecting interactions between two molecules with the use of divided picA-Luc in Experiment 12.

Figure 35:
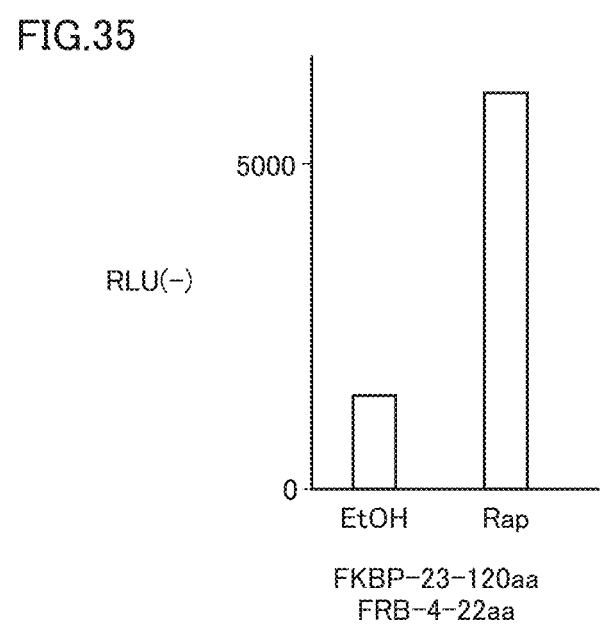

FIG. 35 is a graph showing results of detecting interactions between two molecules with the use of divided picA-Luc in Experiment 12.

Figure 37:
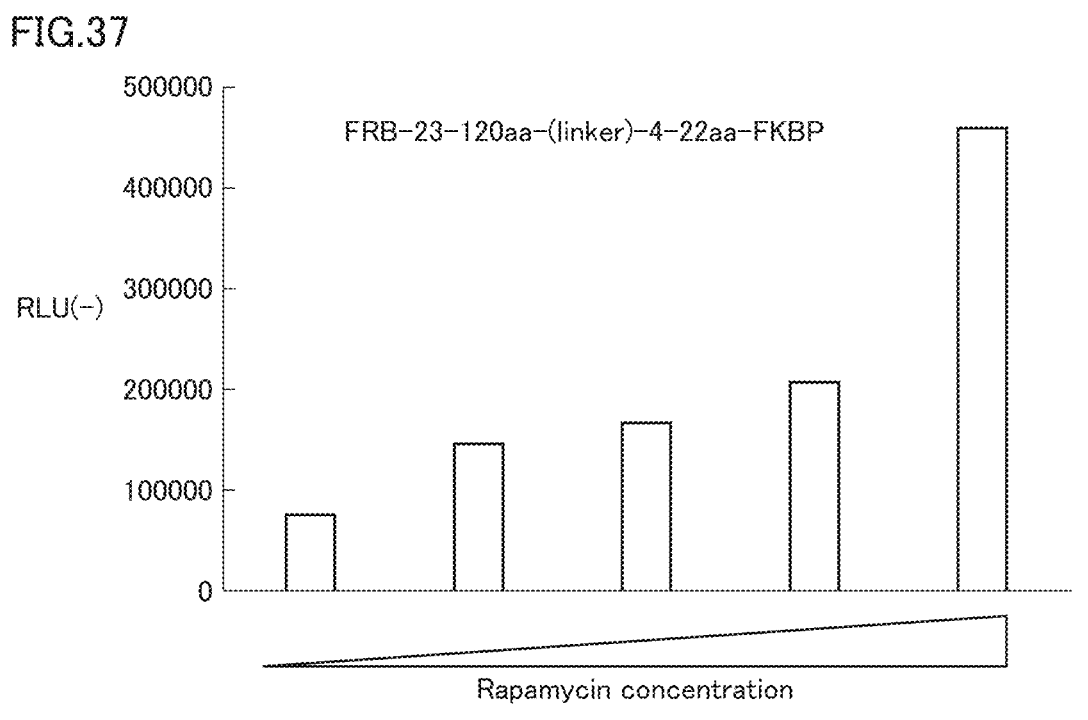

FIG. 37 is a graph showing results of detecting intermolecular interactions with the use of a circular permutated variant including divided picALuc in Experiment 13.

DESCRIPTION OF THE PREFERRED EMBODIMENTS

<Luciferase A>

Figure 3:
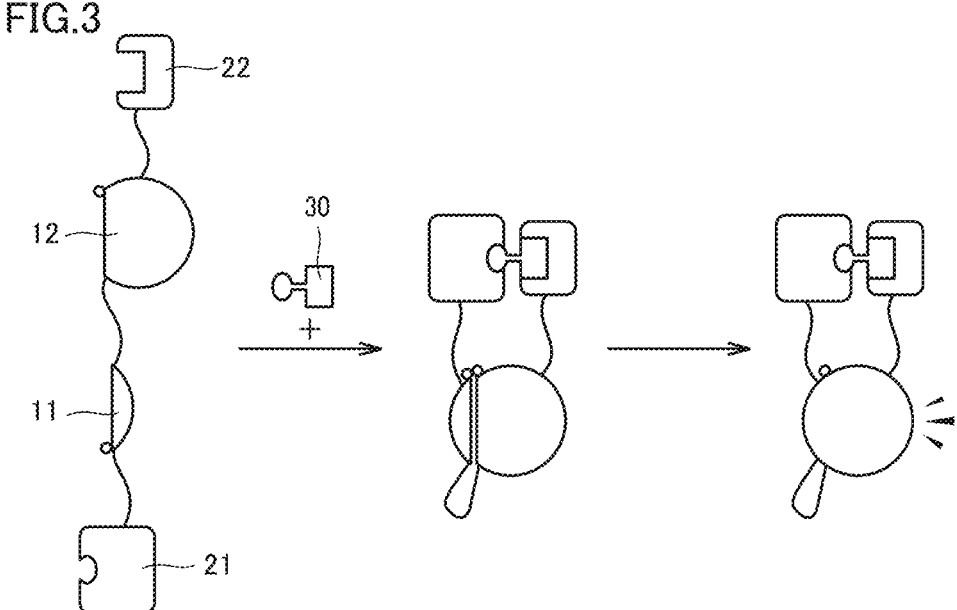
FIG. 3 is a schematic view illustrating an example of detection of intermolecular interactions with the use of a first polypeptide and a second polypeptide.

A reagent kit according to the present invention comprises a first polypeptide and a second polypeptide. Each of the first polypeptide and the second polypeptide is a part in a luciferase A having luciferase activity.

Luciferase refers to an enzyme that oxidizes luciferin and emits light during the oxidation. Luciferase activity herein refers to the activity of enzymatic reaction between a luciferase and a substrate, and it is measured by detecting light (emission spectrum) emitted when the substrate returns to the ground state after it was excited to the excited state due to the enzymatic reaction with the luciferase. The light emitted during the transition to the ground state can be detected with the use of a known luminometer (such as "GloMax" series manufactured by Promega™, Madison, WI, for example) or a known spectrophotometer (such as "Infinite 200 PRO" manufactured by TECAN, for example). By measuring the intensity every minute at a particular wavelength, the time course and the stability of emission can be detected. A shift to a longer wavelength can be detected by performing measurement across the entire wavelength range.

The optimum pH and the optimum temperature for the luciferase activity may be the same as those for known luciferases (such as a copepod-derived luciferase or an artificial luciferase, for example). Preferably, the luciferase activity is the same as the activity of a copepod-derived luciferase. The optimum pH for the luciferase activity is from 5.0 to 8.0, preferably 7.0, and the optimum temperature is from 4° C. to 30° C., preferably 25° C.

The luciferin is not particularly limited, and may be selected as appropriate for the particular luciferase. The luciferin may be a known substrate such as coelenterazine-based one, firefly-luciferin-based one, Cypridina-luciferin-based one, and/or furimazine, and it is preferably a coelenterazine-based substrate. Examples of the coelenterazine-based substrate include natural coelenterazine, coelenterazine ip, coelenterazine i, coelenterazine hcp, coelenterazine 400A, coelenterazine cp, coelenterazine f, coelenterazine h, and coelenterazine n, preferably include coelenterazine or coelenterazine h.

An aspect of the luciferase A includes:

(A) an amino acid sequence in SEQ ID NO: 1 with deletion of an amino acid sequence from position 1 to 69 and an amino acid sequence from position 204 to 221.

An aspect of the luciferase A includes:

(A1) an amino acid sequence from position 75 to 203 of the amino acid sequence in SEQ ID NO: 1, and the number of amino acid residues may be 140 or less. The luciferase A may consist of an amino acid sequence from position 75 to 203 of the amino acid sequence in SEQ ID NO: 1.

(A2) The luciferase A includes an amino acid sequence from position 75 to 203 of the amino acid sequence in SEQ ID NO: 1, and the molecular weight may be 20 kDa or less.

An aspect of the luciferase A includes:

(B) an amino acid sequence in SEQ ID NO: 1 with deletion of an amino acid sequence from position 1 to 69 and deletion or substitution of at least one of amino acid residues at positions 146 to 156.

An aspect of the luciferase A may be:

(B1) an amino acid sequence that includes an amino acid sequence from position 70 to 221 of the amino acid sequence in SEQ ID NO: 1 with deletion or substitution of at least one of amino acid residues at positions 146 to 156. The luciferase A may consist of an amino acid sequence from position 70 to 221 of the amino acid sequence in SEQ ID NO: 1 with deletion or substitution of at least one of amino acid residues at positions 146 to 156.

The luciferase A may further comprise:

(C) in the above-described amino acid sequence (A) or (B), deletion of at least one of amino acid residues at positions 70 to 74, or deletion of the entire amino acid sequence from position 70 to 74, of the amino acid sequence in SEQ ID NO: 1.

The luciferase A preferably includes deletion of 2 or more, 3 or more, 4 or more, 5 or more, 6 or more, or 7 or more of amino acid residues at positions 146 to 156 of the amino acid sequence in SEQ ID NO: 1. Into the deleted site, a linker sequence of one to several bases may be inserted. The luciferase A may have 6 or less, 5 or less, 4 or less, 3 or less, 2 or less, 1 or less, or 0 amino acid residues between positions 146 and 156 (inclusive) of the amino acid sequence in SEQ ID NO: 1.

The molecular weight of the luciferase A is preferably 20 kDa or less, more preferably 18 kDa or less, further preferably 15 kDa or less, further preferably 14 kDa or less, particularly preferably 13 kDa or less. The molecular weight of the luciferase A is 10 kDa or more, for example.

The number of amino acid residues of the luciferase A is, for example, 160 or less, preferably 155 or less, 150 or less, 146 or less, 143 or less, 140 or less, 136 or less, 133 or less, 130 or less, 126 or less, 123 or less, 122 or less, 121 or less, 120 or less, 119 or less, 118 or less, or 117 or less. The number of amino acid residues of the luciferase A is 100 or more, for example.

Among the amino acids represented by Xaa in SEQ ID NO: 1, amino acid residues at positions 3, 20-29, 31, 32, 35, 37, 64-66, 69, 76-77, 85-86, 89-90, 129, 140-144, 148-151, 159, 161, 188, 191, 202, and 206 are not particularly limited. Among these, amino acid residues at positions 22-23, 39-40, 76-77, 140, and 148-151 are optionally deleted. Preferably, amino acid residue at position 3 is E or G; amino acid residues at positions 20-29 form a PTENKDDI sequence (2 residues deleted, SEQ ID NO: 2), an ATINEEDI sequence (2 residues deleted, SEQ ID NO: 3), an ATINENFEDI sequence (SEQ ID NO: 4), an HHHHHHHH sequence (2 residues deleted, SEQ ID NO: 5), an EKLISEE sequence (2 residues deleted, SEQ ID NO: 6), an MMYPYDVP sequence (2 residues deleted, SEQ ID NO: 7), or an MMDYKDDD sequence (2 residues deleted, SEQ ID NO: 8); amino acid residue at position 31 is I, L, Y, or K; amino acid residue at position 32 is V or A; amino acid residue at position 35 is E or G; amino acid residue at position 37 is K or S; amino acid residues at positions 64-66 form an ANS sequence or a DAN sequence; amino acid residue at position 69 is D or G; amino acid residues at positions 76-77 form a GG sequence or are K (1 residue deleted) or optionally deleted; amino acid residues at positions 85-86 form an LE, KA, or KE sequence; amino acid residues at positions 89-90 form a KE sequence, an IE sequence, an LE sequence, or a KI sequence; amino acid residue at position 129 is E, G, or A; amino acid residues at positions 140-144 form a TEEET sequence (SEQ ID NO: 9), a GEAI sequence (1 residue deleted, SEQ ID NO: 10), or a VGAI sequence (1 residue deleted, SEQ ID NO: 11); amino acid residues at positions 148-151 form a GVLG sequence (SEQ ID NO: 12) or are I (3 residues deleted) or optionally deleted as a whole; amino acid residue at position 159 is D, E, N, F, Y, or W; amino acid residue at position 161 is E, A, or L; amino acid residue at position 188 is K, F, Y, or W; amino acid residue at position 191 is D, A, N, F, Y, or W; amino acid residue at position 202 is A or K; and amino acid residue at position 206 is S, D, N, F, Y, or W.

Amino acid residues at positions 13, 16, 174, and 218 of SEQ ID NO: 1 are hydrophobic amino acids (such as V, F, A, L, I, and G, for example), and preferably, amino acid residue at position 13 is V or F, amino acid residue at position 16 is V or A, amino acid residue at position 174 is V or A, and amino acid residue at position 218 is A or L.

Amino acid residues at positions 5, 67, 75, 101, 119, and 214 of SEQ ID NO: 1 are hydrophilic amino acids (such as Q, K, D, R, H, E, and T, for example), and preferably, amino acid residue at position 5 is Q or K, amino acid residue at position 67 is D or R, amino acid residue at position 75 is K, H, R, or E, amino acid residue at position 101 is T or H, amino acid residue at position 119 is K, E, or Q, and amino acid residue at position 211 is K or T.

Amino acid residues at positions 4, 6, 7, 10, 11, 15, 33, 34, 39-41, 63, 68, 74, 78, 83, 137, 160, and 203 of SEQ ID NO: 1 are aliphatic amino acids. Amino acid residues at positions 39, 40, and 70 are optionally deleted. Amino acid residues at positions 4, 6, 7, 10, 11, 15, 34, 63, 78, 83, and 160 are preferably high-molecular-weight aliphatic amino acids (such as I, V, L, and M, for example), and some of them (but not many of them) may be low-molecular-weight aliphatic amino acid(s). More preferably, amino acid residue at position 4 is I or V; amino acid residue at position 6 is V or L; amino acid residue at position 7 is L or I; amino acid residue at position 10 is L or V; amino acid residue at position 11 is I or L; amino acid residue at position 15 is L or V; amino acid residue at position 34 is I or V; amino acid residue at position 63 is L or V; amino acid residue at position 78 is L or M; amino acid residue at position 83 is L or M; and amino acid residue at position 160 is L or M. Amino acid residues at positions 33, 39-41, 68, 74, 137, and 203 are preferably low-molecular-weight aliphatic amino acids (such as A, G, and T, for example), and some of them (but not many of them) may be high-molecular-weight aliphatic amino acid(s). More preferably, amino acid residue at position 33 is G, L, or A; amino acid residue at position 39 is G or A or optionally deleted or optionally S or F; amino acid residue at position 40 is T or optionally deleted; amino acid residue at position 41 is T or A; amino acid residue at position 68 is A or G; amino acid residue at position 74 is G or optionally deleted; amino acid residue at position 137 is G or A; and amino acid residue at position 203 is T or G.

Amino acid residues at positions 72, 73, 97, and 110 of SEQ ID NO: 1 are positively-charged amino acids (basic amino acids, such as K, R, and H). Amino acid residues at positions 72 and 73 are optionally deleted. Preferably, amino acid residues at positions 72 and 73 are R or optionally deleted, amino acid residue at position 97 is K or R, and amino acid residue at position 110 is H or K.

Amino acid residues at positions 62 and 211 of SEQ ID NO: 1 are negatively-charged amino acids (acidic amino acids, such as N, D, Q, and E), and preferably, amino acid residue at position 62 is N or D and amino acid residue at position 211 is Q or E.

Specific examples of the luciferase having the amino acid sequence in SEQ ID NO: 1 include ALuc10 (SEQ ID NO: 13), ALuc15 (SEQ ID NO: 14), ALuc16 (SEQ ID NO: 15), ALuc17 (SEQ ID NO: 16), ALuc18 (SEQ ID NO: 17), ALuc19 (SEQ ID NO: 18), ALuc21 (SEQ ID NO: 19), ALuc22 (SEQ ID NO: 20), ALuc23 (SEQ ID NO: 21), ALuc24 (SEQ ID NO: 22), ALuc25 (SEQ ID NO: 23), ALuc26 (SEQ ID NO: 24), ALuc27 (SEQ ID NO: 25), ALuc28 (SEQ ID NO: 26), ALuc29 (SEQ ID NO: 27), ALuc30 (SEQ ID NO: 28), ALuc31 (SEQ ID NO: 29), ALuc32 (SEQ ID NO: 30), ALuc33 (SEQ ID NO: 31), ALuc34 (SEQ ID NO: 32), ALuc41 (SEQ ID NO: 33), Aluc42 (SEQ ID NO: 34), ALuc43 (SEQ ID NO: 35), Aluc44 (SEQ ID NO: 36), ALuc45 (SEQ ID NO: 37), Aluc46 (SEQ ID NO: 38), ALuc47 (SEQ ID NO: 39), ALuc48 (SEQ ID NO: 40), ALuc49 (SEQ ID NO: 41), Aluc50 (SEQ ID NO: 42), ALuc51 (SEQ ID NO: 43), Aluc52 (SEQ ID NO: 44), ALuc53 (SEQ ID NO: 45), ALuc55 (SEQ ID NO: 46), Aluc56 (SEQ ID NO: 47), and ALuc57 (SEQ ID NO: 48). The luciferase having the amino acid sequence in SEQ ID NO: 1 may comprise deletion of some of or all of the amino acid residues at positions 1 to 19 (secretion signal), 20 to 31 (such as an antigen recognition site), and 217 to 221 (GS linker sequence).

A region from position 1 to position 71 of the amino acid sequence in SEQ ID NO: 1 may be an amino acid sequence in SEQ ID NO: 49. Typical examples of luciferase having this sequence include ALuc15, ALuc16, ALuc17, ALuc18, and ALuc24.

A region from position 1 to position 157 of the amino acid sequence in SEQ ID NO: 1 may be an amino acid sequence in SEQ ID NO: 50. Typical examples of luciferase having this sequence include ALuc22, ALuc25, ALuc26, ALuc27, ALuc28, and ALuc29.

By using the luciferase A, it is possible to decrease the size of luciferase. With the luciferase being small, when a fusion protein composed of the luciferase and a target protein or an antibody or the like is expressed within a cell, the expression of the fusion protein should properly occur and the target protein can be less likely to malfunction. With the luciferase being small, the emission value is less likely to be affected by low-molecular compounds, and therefore the luciferase can be suitably used as a reporter protein for drug or ligand screening. Also, in the case of intermolecular interaction analysis by bioluminescence resonance energy transfer (BRET), use of a small luciferase can give stronger detection signals. A small luciferase may be used for secretory luciferase. Secretory luciferase does not require cytolysis for emission value measurement, enabling measurement of time course of gene expression. A small luciferase is easily expressed within a cell, enabling expression and purification in a large quantity. A small luciferase can be expressed by various expression systems. Further, a small luciferase has excellent structural stability.

The luciferase A preferably has a high emission value. The emission peak value of the luciferase A is preferably the same as, or higher than, that of known luciferases such as NanoLuc® and ALuc. A luciferase with a high emission value enables highly sensitive emission detection and makes it possible to lower the concentration limit for detection.

The luciferase A preferably has a high thermal stability; for example, at least 80% of the activity is preserved after heat treatment at a temperature of 50° C. for 10 minutes, and preferably at least 80% of the activity is preserved after heat treatment at a temperature of 60° C. for 10 minutes. A luciferase with a high thermal stability is less likely to become inactivated due to a temperature increase during transportation, and is highly practical at the site of diagnosis, examination, and the like.

The enzyme activity of the luciferase A preferably exhibits an emission spectrum with a wide tail on the longer wavelength side, and its emission spectrum is shifted to the longer wavelength side as compared to, for example, a conventional copepod-derived luciferase. Because a longer wavelength transmits through a living body very well, a luciferase exhibiting an emission spectrum with a wide tail on the longer wavelength side is suitable for live imaging. When coelenterazine is used as a substrate, the luciferase A shows an emission wavelength peak preferably from 470 nm to 490 nm, more preferably at about 482 nm. When coelenterazine h is used as a substrate, the luciferase A shows an emission wavelength peak preferably from 470 nm to 490 nm, more preferably at about 488 nm.

The C terminus of ALuc has been considered as essential for binding to a substrate. An aspect of the luciferase A does not have the C terminus of ALuc but has luciferase activity. Therefore, it seems that the substrate-binding site of a polypeptide without the C terminus of ALuc has a structure different from that of ALuc.

The luciferase A may have an antibody recognition site in the middle or at the end of it. Examples of the antibody recognition site include, but not limited to, His-tag (HHHHHH) (SEQ ID NO: 67), FLAG-tag (DYKDDDDK) (SEQ ID NO: 68), Myc-tag (EQKLISEEDL) (SEQ ID NO: 69), and HA-tag (YPYDVPDYA) (SEQ ID NO: 70).

The luciferase A may have a functional peptide attached to its N terminus or C terminus. When a membrane localization signal (MLS) is attached to the N terminus or the C terminus, for example, the luciferase can be localized in the cell membrane. Herein, even when it is not clearly specified, when two or more peptides including a signal peptide are bonded to each other, a known linker may be used as appropriate to adjust the length, the reading frame, and the like. Having the luciferase localized in the cell membrane has some advantages: substrate and oxygen can be smoothly supplied from outside; and a luciferase-based luminescent probe (such as a luminescent capsule, for example), when used, can quickly respond to external signal.

The luciferase A preferably includes (a) an amino acid sequence in any one of SEQ ID NOs: 51 to 56, and may consist of an amino acid sequence in any one of SEQ ID NOs: 51 to 56. The amino acid sequence in SEQ ID NO: 51 is the amino acid sequence of artificial luciferase ALuc30 with deletion of the N terminus and the C terminus (picALuc30). The amino acid sequence in SEQ ID NO: 54 is the amino acid sequence of ALuc30 with deletion of the N terminal sequence and an intermediate sequence (ALuc30Δloop2N1). Similarly, the amino acid sequences in SEQ ID NOs: 52 and 53 are the amino acid sequences of artificial luciferases ALuc16 and ALuc48, respectively, with deletion of the N terminus and the C terminus, and the amino acid sequences in SEQ ID NOs: 55 and 56 are the amino acid sequences of ALuc16 and ALuc48, respectively, with deletion of the N terminal sequence and an intermediate sequence.

The luciferase A preferably includes (b) an amino acid sequence having at least 85% homology with an amino acid sequence in any one of SEQ ID NOs: 51 to 56, and may consist of an amino acid sequence having at least 85% homology with an amino acid sequence in any one of SEQ ID NOs: 51 to 56. The luciferase A preferably has at least 90%, at least 95%, at least 96%, at least 97%, at least 98%, at least 99%, or at least 99.5% homology with an amino acid sequence in any one of SEQ ID NOs: 51 to 56.

The luciferase A preferably includes (c) an amino acid sequence in any one of SEQ ID NOs: 51 to 56 with deletion, substitution, insertion, or addition of one or several amino acid residues, and may be an amino acid sequence in any one of SEQ ID NOs: 51 to 56 with deletion, substitution, insertion, or addition of one or several amino acid residues. "Several" herein may be from 2 to 20, from 2 to 10, from 2 to 5, or from 2 to 3, for example.

The luciferase A may include an amino acid corresponding to a start codon (methionine in most cases) before amino acid residue at position 1. Amino acid sequences in SEQ ID NOs: 51 to 56 with methionine added to position 1 are shown as SEQ ID NOs: 57 to 62.

An aspect of the luciferase A may include the following (a1) to (c1), or may consist of the following (a1) to (c1):

(a1) an amino acid sequence in any one of SEQ ID NOs: 57 to 62;

(b1) an amino acid sequence having at least 85% homology with an amino acid sequence in any one of SEQ ID NOs: 57 to 62; or (c1) an amino acid sequence in any one of SEQ ID NOs: 57 to 62 with deletion, substitution, insertion, or addition of one or several amino acid residues.

The luciferase A preferably has at least 90%, at least 95%, at least 96%, at least 97%, at least 98%, at least 99%, or at least 99.5% homology with an amino acid sequence in any one of SEQ ID NOs: 57 to 62.

<Polypeptide>

Figure 1:
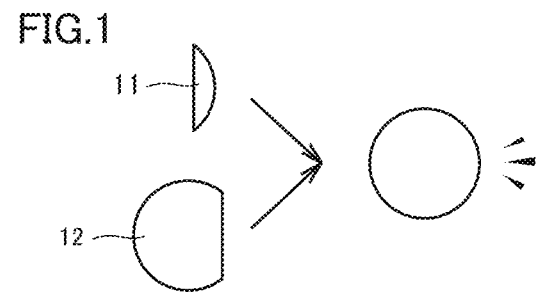

Each of the first polypeptide and the second polypeptide is a part in the luciferase A. Each of the first polypeptide and the second polypeptide includes a part in any one of the above-described amino acid sequences (A) to (C), for example, and preferably, it includes a part in any one of the above-described amino acid sequences (a) to (c). Usually, the first polypeptide alone or the second polypeptide alone does not have luciferase activity. As shown in FIG. 1, a first polypeptide 11 exhibits luciferase activity when in close proximity to a second polypeptide 12. More specifically, the first polypeptide can emit luminescence in the presence of the second polypeptide and a substrate. To make the first polypeptide and the second polypeptide come into contact with or come close to each other, a solution containing the first polypeptide can be mixed with a solution containing the second polypeptide, for example.

With respect to the expression "does not have luciferase activity" herein, a given sample is judged to not have luciferase activity when, in a method of Experiment 11-1 described below, for example, the emission value thereof is the same as that of a sample from position 4 to 120. With respect to the expression "has luciferase activity", a given sample is judged to have luciferase activity when, in a method of Experiment 11-1 described below, for example, the emission value thereof is sufficiently higher (for example, twice or more, three times or more) than that of another sample that was judged not to have emission activity.

Each of the first polypeptide and the second polypeptide is a part in an already small luciferase A, and, accordingly, it is small. By using a small polypeptide as a probe, its fusion protein with the target protein is likely to be expressed in a normal fashion. Moreover, a small polypeptide is less likely to inhibit the function of the target protein. A small polypeptide is less likely to inhibit interactions between the target protein and other molecules. Preferably, the luciferase activity exhibited when the first polypeptide and the second polypeptide come into contact with or come close to each other has the same characteristics as the activity of the luciferase A. Each of these polypeptides may have a functional peptide or an antibody recognition site attached thereto, as in the case of the luciferase A.

Usually, an amino acid sequence constituting the first polypeptide is a different sequence from an amino acid sequence constituting the second polypeptide. The amino acid sequence constituting the first polypeptide may or may not partially overlap with the amino acid sequence constituting the second polypeptide. When not overlapping with each other, the amino acid sequence constituting the first polypeptide and the amino acid sequence constituting the second polypeptide may be connected to one another within the amino acid sequence constituting the luciferase A (the amino acid sequence in SEQ ID NO: 1), or may have deletion of one or several amino acid residues. An example combination of the first polypeptide and the second polypeptide is a combination of the N-terminal-side polypeptide and the C-terminal-side polypeptide of the luciferase A when it is divided into these two portions.

At least one of the first polypeptide and the second polypeptide may have, in amino acid sequence(s) in SEQ ID NO: 1 or SEQ ID NOs: 51 to 53, an amino acid sequence corresponding to one selected from amino acid sequences from position 4 to 20, from position 4 to 21, from position 4 to 22, from position 4 to 23, from position 4 to 24, from position 4 to 33, from position 4 to 34, from position 4 to 35, from position 4 to 36, from position 4 to 37, from position 4 to 45, from position 4 to 46, from position 4 to 47, from position 4 to 48, from position 4 to 49, from position 4 to 56, from position 4 to 57, from position 4 to 58, from position 4 to 59, from position 4 to 60, from position 4 to 62, from position 4 to 63, from position 4 to 64, from position 4 to 65, from position 4 to 66, from position 4 to 67, from position 4 to 70, from position 4 to 71, from position 4 to 72, from position 4 to 73, from position 4 to 74, from position 4 to 75, from position 4 to 76, from position 4 to 77, from position 4 to 78, from position 4 to 79, from position 4 to 80, from position 4 to 84, from position 4 to 88, from position 4 to 89, from position 4 to 90, from position 4 to 91, from position 4 to 92, from position 4 to 93, from position 4 to 101, from position 4 to 102, from position 4 to 103, from position 4 to 104, and position 4 to 105 of the amino acid sequence in SEQ ID NO: 51, or may consist of that amino acid sequence. At least one of the first polypeptide and the second polypeptide may have, in addition to the above sequence, one or more of amino acid residues corresponding to positions 1 to 3 of the amino acid sequence in SEQ ID NO: 51, at the N terminus.

At least one of the first polypeptide and the second polypeptide may have, in amino acid sequence(s) in SEQ ID NO: 1 or SEQ ID NOs: 51 to 53, an amino acid sequence corresponding to one selected from amino acid sequences from position 21 to 120, from position 22 to 120, from position 23 to 120, from position 24 to 120, from position 25 to 120, from position 34 to 120, from position 35 to 120, from position 36 to 120, from position 37 to 120, from position 38 to 120, from position 46 to 120, from position 47 to 120, from position 48 to 120, from position 49 to 120, from position 50 to 120, from position 57 to 120, from position 58 to 120, from position 59 to 120, from position 60 to 120, from position 61 to 120, from position 63 to 120, from position 64 to 120, from position 65 to 120, from position 66 to 120, from position 67 to 120, from position 68 to 120, from position 69 to 120, from position 70 to 120, from position 71 to 120, from position 72 to 120, from position 73 to 120, from position 74 to 120, from position 75 to 120, from position 76 to 120, from position 77 to 120, from position 78 to 120, from position 79 to 120, from position 80 to 120, from position 81 to 120, from position 85 to 120, from position 89 to 120, from position 90 to 120, from position 91 to 120, from position 92 to 120, from position 93 to 120, from position 94 to 120, from position 102 to 120, from position 103 to 120, from position 104 to 120, from position 105 to 120, and from position 106 to 120 of the amino acid sequence in SEQ ID NO: 51, or may consist of that amino acid sequence. At least one of the first polypeptide and the second polypeptide may have, in addition to the above sequence, one or more of amino acid residues corresponding to positions 121 and 122 of the amino acid sequence in SEQ ID NO: 51, at the C terminus.

Preferably, at least one of the first polypeptide and the second polypeptide has:

(1) any one of amino acid sequences from position 4 to 77 (SEQ ID NO: 76), from position 4 to 22 (SEQ ID NO: 77), from position 4 to 58 (SEQ ID NO: 78), from position 4 to 64 (SEQ ID NO: 79), from position 4 to 72 (SEQ ID NO: 80), from position 23 to 120 (SEQ ID NO: 81), from position 78 to 120 (SEQ ID NO: 82), from position 65 to 120 (SEQ ID NO: 83), from position 73 to 120 (SEQ ID NO: 84), and from position 104 to 120 (SEQ ID NO: 85) of the amino acid sequence in SEQ ID NO: 51;

(2) an amino acid sequence having at least 85% homology with an amino acid sequence in any one of SEQ ID NO: 76 to SEQ ID NO: 85; or (3) an amino acid sequence in any one of SEQ ID NO: 76 to SEQ ID NO: 85 with deletion, substitution, insertion, or addition of one or several amino acid residues.

Preferably, at least one of the first polypeptide and the second polypeptide has at least 90%, at least 95%, at least 96%, at least 97%, at least 98%, at least 99%, or at least 99.5% homology with an amino acid sequence in any one of SEQ ID NOs: 76 to 85.

When the first polypeptide has an amino acid sequence in SEQ ID NO: 76 or SEQ ID NO: 77, the second polypeptide may have an amino acid sequence in SEQ ID NO: 81 or SEQ ID NO: 82. The combination of the first polypeptide and the second polypeptide may be interchangeable. A preferable combination of the first polypeptide and the second polypeptide is a combination of SEQ ID NO: 77 and SEQ ID NO: 81, or a combination of SEQ ID NO: 76 and SEQ ID NO: 81. Other preferable combinations of the first polypeptide and the second polypeptide are a combination of SEQ ID NO: 78 and SEQ ID NO: 81, a combination of SEQ ID NO: 79 and SEQ ID NO: 83 or SEQ ID NO: 84, and a combination of SEQ ID NO: 80 and SEQ ID NO: 81, SEQ ID NO: 84, or SEQ ID NO: 85.

Figure 2:
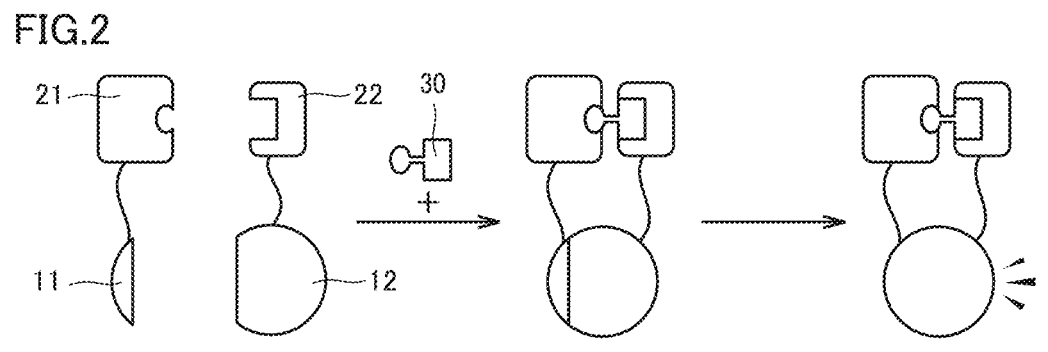

As shown in FIG. 2, first polypeptide 11 may be connected to other molecules such as a first target protein 21. In a fusion protein including polypeptide 11 and first target protein 21, first polypeptide 11 and first target protein 21 may be connected to each other via a linker sequence. The first target protein may be a detection target to be detected its interactions with other target molecules such as a second target protein 22. First target protein 21 and second target protein 22 together may form a dimer, and the dimer may be formed only when a small molecule 30 is present. Second target protein 22 is connected to second polypeptide 12. Second target protein 22 and second polypeptide 12 may be connected to each other via a linker sequence. When first target protein 21 and second target protein 22 interact with each other, first polypeptide 11 and second polypeptide 12 come close to or come into contact with each other, and, in the presence of a substrate, luminescence is detected.

First polypeptide 11 and second polypeptide 12 may not necessarily be connected to each other. First polypeptide 11 and second polypeptide 12 may be connected to each other, and, for example, may be connected to each other via a linker sequence. As shown in FIG. 3, first target protein 21, first polypeptide 11, second polypeptide 12, and second target protein 22 may be all connected together. Such a fusion protein is also called a circular permutated variant. In a fusion protein including first target protein 21, first polypeptide 11, second polypeptide 12, and second target protein 22, each connection may be formed via a linker sequence. When first target protein 21 and second target protein 22 interact with each other, first polypeptide 11 and second polypeptide 12 come close to or come into contact with each other, and, in the presence of a substrate, luminescence is detected. As compared to when first target protein 21 and second target protein 22 exist as two separate components, a circular permutated variant allows for easy detection of interactions between first target protein 21 and second target protein 22.

<Nucleic Acid Coding for Polypeptide>

A nucleic acid according to an embodiment of the present invention codes for the above-described polypeptide or fusion protein. From the nucleic acid, the above-described polypeptide or fusion protein can be produced. The nucleic acid is preferably DNA or RNA. The nucleic acid coding for the polypeptide may include a start codon on the 5' end side of the base sequence corresponding to the above-described polypeptide, and may include a stop codon at the 3' end of the base sequence. The nucleic acid may include an intron sequence.

The nucleic acid according to an embodiment includes a nucleic acid that includes a base sequence in which a codon coding for an amino acid in a coding region is replaced by another codon coding for the same amino acid. From the viewpoint of enhancing expression of the polypeptide, the nucleic acid according to an embodiment may be a nucleic acid that includes a base sequence in which codon usage has been changed so as to be suitable for the host living thing or for the type of the transformed cell.

The nucleic acid according to the present embodiment can be obtained by chemical synthesis, PCR, or the like.

<Vector>

A vector according to an embodiment of the present invention includes the above-described nucleic acid. The vector is a nucleic acid molecule capable of amplifying and/or retaining DNA, and examples thereof include expression vectors and cloning vectors. In an example, the above-described nucleic acid, which is inserted in an expression vector, is introduced into a host cell and/or the like, and expresses the above-described polypeptide or fusion protein. The expression vector may have a promoter sequence and a terminator sequence aimed at expressing a gene incorporated therein. The vector according to the present embodiment can be obtained by inserting the above-described nucleic acid into a suitable vector.

The vector may be, for example, a vector derived from a bacterial plasmid, a vector derived from a yeast plasmid, a viral vector, a cosmid vector, a phagemid vector, an artificial chromosome vector, and/or the like. Examples of the vector include pBR322, pUC plasmid vector, and pET-based plasmid vector. More specifically, when *Escherichia coli* is used as the host cell, pUC19, pUC18, pUC119, pBluescriptII, and/or pET32 may be used, for example. When a mammalian cell is used as the host cell, pRc/RSV, pRc/CMV, retroviral vector, adenoviral vector, adeno-associated virus vector, and/or the like may be used, for example.

A nucleic acid coding for the second polypeptide or for a fusion protein including the second polypeptide and the second target protein may be contained in the same vector as, or in a different vector from, the vector containing a nucleic acid coding for the first polypeptide.

<Transformed Cell>

A transformed cell according to an embodiment of the present invention is a cell that has the above-described nucleic acid introduced therein. The nucleic acid, when it is being introduced into the cell, may be contained in a vector. The transformed cell is capable of expressing the first polypeptide or a fusion protein including the same. Preferably, the same transformed cell further expresses the second polypeptide or a fusion protein including the second polypeptide and the second target protein. These may be secreted into the supernatant. Examples of the method for introducing the nucleic acid into the cell include chemical techniques such as calcium phosphate method, DEAE-dextran method, and cationic liposome method; biological techniques such as adenoviral vector, vaccinia virus vector, retroviral vector, and HVJ liposome; and physical techniques such as electroporation, DNA direct injection, and gene gun. A suitable introduction method may be selected depending on the cell used for introduction.

The cell into which the nucleic acid is introduced may be either a eukaryotic cell or a prokaryotic cell, and examples include bacterial cells, fungal cells, plant cells, animal cells, and insect cells. The cell may be a yeast cell, an *Escherichia coli* cell, or a mammalian cell, and the mammal includes human, cow, horse, sheep, monkey and ape, pig, mouse, rat, hamster, guinea pig, rabbit, and dog.

<Protein Interaction Analysis Method>

A protein interaction analysis method according to an embodiment of the present invention uses the above-described reagent kit. This method makes it possible to detect interactions between two proteins by way of luminescence. The interactions between two proteins may be mediated by a small molecule (a ligand). This method makes it possible to detect the presence of the small molecule by way of luminescence. The polypeptide used in this method has a small molecular weight, and therefore its fusion protein with the target protein is likely to be expressed in a normal fashion. Moreover, the polypeptide used in this method is less likely to inhibit the function of the target protein.

An example of the protein interaction analysis method includes mixing the above-described first polypeptide or a fusion protein including the first polypeptide and the above-described second polypeptide or a fusion protein including the second polypeptide, in the presence of luciferin. The protein interaction analysis method may further include:

preparing a plasmid capable of expressing a fusion protein described above; expressing the first polypeptide or a fusion protein including the first polypeptide in a cell; expressing the second polypeptide or a fusion protein including the second polypeptide in a cell; collecting the first polypeptide or a fusion protein including the first polypeptide from the cell or the culture supernatant; collecting the second polypeptide or a fusion protein including the second polypeptide from the cell or the culture supernatant; detecting luminescence; and/or the like.

<Reporter Analysis>

The above-described polypeptide may also be used as a probe to carry out various reporter analyses. The first polypeptide, in combination with the second polypeptide, may replace a luminescence substance or a fluorescent substance in a reporter analysis method that uses a conventional luciferase or a variety of fluorescent proteins.

The reporter analysis method herein refers to an analytic method that involves using the first polypeptide or the second polypeptide as a reporter protein and observing a factor such as whether or not light is emitted or the amount, timing, or location of emission, which reflects the intracellular behavior of a target protein or a target gene elicited in response to external stimulation. More specifically, the reporter analysis method may be regarded as a method for qualitatively or quantitatively measuring the location, timing, or amount of expression of a target gene, in the form of the location, timing, or amount of emission. In the reporter analysis, multiple enzymes or proteins capable of emitting light of different wavelengths may be concurrently used.

The reporter analysis may be carried out in the living body of a mammal or the like, or in a cultured cell, or in a test tube. Under in vivo conditions such as in a living body, a reporter gene consisting of a nucleic acid coding for an amino acid sequence constituting the above-described polypeptide is coupled to a target gene and incorporated into a vector, which is then introduced into a target cell. Examples of the cultured cell include mammalian cells used in typical genetic recombination, such as COS cells, CHO-K1 cells, HeLa cells, HEK293 cells, and NIH3T3 cells; bacterial cells such as those of yeast and *Escherichia coli*; and insect cells.

Next, the reporter analysis method according to the present invention will be described, where it is classified into three types ("basic", "inducible", and "activatable") according to Niu et al., Theranostics, 2, 2012, 413. and also, the application of the above-described polypeptide to each of these analytic methods is explained.

(1) Basic Method

The basic method is the simplest reporter analysis system, where a target protein to be investigated its behavior is coupled to and labelled with a probe. When the first polypeptide is used as a probe in the basic method, a fusion protein which includes the first polypeptide and the target protein or a protein capable of binding the target protein may be prepared. This method is different from other reporter analysis methods, in that the fusion protein is expressed by means of a non-regulatory promoter. The fusion protein may also be used for in vivo imaging of the target protein.

The fusion protein encompasses the following: (i) a single-piece fusion protein that is expressed from a nucleic acid coding for a fusion protein including the first polypeptide and the target protein or a protein (including a peptide) capable of recognizing the target protein; and (ii) a coupled fusion protein that is obtained by separately expressing the first polypeptide and the target protein or a protein capable of recognizing the target protein and coupling them by chemical reaction. Examples of the technique to couple the separately-expressed proteins, etc. by chemical reaction include coupling via a crosslinker, coupling via avidin-biotin binding, and coupling via chemical reaction of amino acid residues.

Examples of the fusion protein include a probe-labelled antibody that is an antibody coupled to a probe. Regarding this fusion protein, a probe sequence may be coupled to the upstream or downstream of cDNA for a single-chain variable region fragment (scFv) of the antibody to prepare a chimeric DNA, and the resulting DNA may be inserted into a suitable expression vector, which may then be introduced into a cell for expression, and thereby the fusion protein may be obtained.

(2) Inducible Method

In the inducible method, unlike in the basic method, reporter expression is regulated by a promoter. Luciferase has been used as a reporter protein in the inducible method for analyzing the timing and amount of gene expression when preparing recombinant proteins by recombinant DNA technique, and especially, it has been widely used as an indicator of changes in the timing and amount of expression elicited in response to external stimulation. Examples of an analysis system included in the inducible method include reporter gene assay, yeast two-hybrid assay, mammal two-hybrid assay, bioluminescence resonance energy transfer (BRET), protein splicing assay (PSA), protein complementation assay (PCA), and circular permutation assay. When the polypeptide according to the present invention is used as a reporter gene in these analysis methods, the measuring performance of these assays can be dramatically enhanced.

(i) Reporter Gene Assay

A reporter gene assay method is generally used as a means for analyzing the activation of transcription factor as well as the regulation of gene expression elicited in response to external stimulation. For example, it is used for detecting an endocrine disruptor (an environmental hormone) that interferes with signal transduction intermediated by a nuclear receptor. Expression of a target gene associated with signal transduction intermediated by a nuclear receptor (such as a hormone response gene, for example) is triggered by bonding of a ligand-receptor complex to a cis region that is responsible for regulating transcription of the gene (a hormone response element). A plasmid that has a reporter gene incorporated to the downstream of the cis region of a variety of hormone response genes is introduced into a cell, and the amount of a hormone molecule or an endocrine disruptor that can be a ligand is detected in the form of emission value.

Use of firefly luciferase (which has been widely used) in a reporter gene assay method has the following disadvantages: [1] due to the high molecular weight, it takes long for the expression to occur, putting heavy burdens on the host cell; and [2] due to the low emission intensity, it usually takes one to two days following stimulation for a sufficient amount of luciferase (reporter) is accumulated; these disadvantages will be resolved by selecting the above-described polypeptide as a probe.

Use of the above-described polypeptide as a probe is advantageous in that, due to the very high emission intensity of the reporter, measurement can be performed in a very short time after stimulation. This enables a significant reduction of measurement time as compared to conventional reporter proteins, and also, this offers a high over-time stability of emission to enable emission measurement in a cell line that exhibits a poor gene transfer efficiency. In addition, a shift to a longer wavelength offers a higher permeation through the cell membrane and/or the skin, leading to a decreased background and a higher precision in measurement.

More specifically, in order to apply the above-described polypeptide to reporter gene assay, the probe sequence may be coupled to a known eukaryotic expression vector that has a special promoter mounted upstream, and the resulting vector may be introduced into a eukaryotic cell, followed by, after a lapse of a certain period of time, measurement of the emission value under conditions with or without signal (stimulation). As the expression vector for reporter gene assay capable of mounting a polypeptide thereon, a known pTransLucent vector may be used, and the mounting can be easily carried out by a known method.

(ii) Two-Hybrid Method

A two-hybrid method is a technique for investigating protein-protein interactions, and the firstly-established one was a yeast two-hybrid (Y2H) system, which was established in 1989 using yeast (*Saccharomyces cerevisiae*). By taking advantage of the fact that a GAL4 protein (a transcriptional activator) DNA-binding domain (GAL4 DBD) is separable from a transcriptional activation domain, it is possible to express GAL4 DBD and a certain protein A (bait) in the form of a fusion protein to see if it interacts with protein B (prey), which is expressed at the same time in the cell and made to form a fusion protein with a transcriptional activation domain (TA). When protein A binds to protein B, it means that DBD comes close to TA to allow the DNA-binding domain (DBD) to bind to base sequence "UASG", thereby facilitating the expression of the polypeptide downstream. When the first polypeptide and the second polypeptide are combined and bioluminescence is monitored in the presence of a specific substrate, the affinity between protein A and protein B can be measured, enabling the screening for a protein or a peptide that is capable of interacting with protein A (bait). In this case, protein B (prey) may also be provided by means of expression library.

As the host cell, not only a yeast cell but also a bacterial cell such as *Escherichia coli*, a mammalian cell, and/or an insect cell may be used. In that case, not only GAL4 DBD (which is a yeast-derived transcriptional activator) but also "LexA", a repressor protein derived from *Escherichia coli*, may be used, for example. A DNA coding for them is coupled to a DNA coding for a bait protein (namely, the above certain protein A) such as a ligand-binding region of a ligand-response transcriptional regulator, and then coupled to the downstream of a promoter that is capable of functioning in the host cell. As "a transcriptional activation region of a transcriptional activator", GAL4 transcriptional activation region, B42 acidic transcriptional activation region derived from *Escherichia coli*, and/or transcriptional activation region of herpes simplex virus VP16 may be used, for example. A DNA coding for the transcriptional activation region is coupled to a DNA coding for a prey protein (namely, the above certain protein B), and then coupled to the downstream of a promoter that is capable of functioning in the host cell.

Specific examples of a vector that has a DNA coding for a DNA-binding region of transcriptional regulator GAL4 and is also usable in a budding yeast as a host cell include plasmid pGBT9 (manufactured by Clontech™, Kosatsu, Japan). Examples of a vector that has a DNA coding for GAL4 transcriptional activation region and is also usable in a budding yeast include plasmid pGAD424 (manufactured by Clontech™). Examples of a vector that has a DNA coding for GAL4 DNA-binding region and is also usable in a mammalian cell include pM (manufactured by Clontech™)

and pBIND (manufactured by Promega™), and examples of a vector that has a DNA coding for a transcriptional activation region of herpes simplex virus VP16 and is also usable in a mammalian cell include pVP16 (manufactured by Clontech™) and pACT (manufactured by Promega™). Further, examples of a vector that has a DNA coding for LexA DNA-binding region and is also usable in a mammalian cell include pLexA (manufactured by Clontech™), and examples of a vector that has a DNA coding for B42 and is also usable in a mammalian cell include pB42AD (manufactured by Clontech™).

For example, a vector that has the first polypeptide inserted to the downstream of a region such as GAL4-binding region ("UASG") may be constructed; when a mammalian host is used, commercially-available pG5Luc vector (Promega™) and/or pFR-Luc vector (Stratagene) may be used and on which the first polypeptide may be easily mounted by a known method to replace the firefly luciferase originally mounted on the vector. Replacing chloramphenicol acetyltransferase (CAT) of commercially-available pG5CAT vector (Clontech™) may also be adopted.

(3) Activatable Method

The activatable method is a reporter analysis method that exploits the ability of a combination of the first polypeptide and the second polypeptide to actively respond to ligand stimulation to emit light. Typical examples include single-molecular bioluminescent probes and luminescent capsules, and other applicable assays include protein complentation assay (PCA) and protein splicing assay (PSA).

(i) Production of Luminescent Fusion Protein (Luminescent Capsule)

By binding a membrane localization signal (MLS) to the C terminal side of the above-described polypeptide, it is possible to localize the polypeptide in or at the cell membrane. This molecular design for luciferase localization in the cell membrane allows for smooth supply of substrate and oxygen, enabling stable visualization of bioluminescence with a very high luminance. In this procedure, a gene for any polypeptide and/or protein may be inserted, as a cargo, between the nucleic acid coding for the polypeptide and the nucleic acid coding for the signal peptide. This allows for efficient delivery of the cargo protein to the cell membrane surface, and also makes the delivered location emit light. As an example, a DEVD sequence (SEQ ID NO:90) and/or an IETD sequence (SEQ ID NO:91) (each of which responds to cell death) may be attached to where the protein is coupled, as a cargo, to create a system that can actively respond to and visualize cell death using caspase-3 and/or caspase-8 activity as a signal. A luminescent fusion protein having this structure is also called "luminescent capsule". A luminescent capsule may also be used for assessing toxicity of chemical substances.

As compared to a conventional luminescent probe, the luminescent capsule has advantages of having very high luminance and stable emission properties and responding even to an analyte that does not permeate through the cell membrane. The basic structure of the luminescent capsule is "a membrane localization signal (MLS)" attached to "the C terminus of the luciferase itself". The above-described polypeptides may be tandemly linked for enhancing the emission amount of the enzyme. The luminescent capsule allows for visualization of the action of a compound that triggers a change of cell surface morphology such as cell death, as a change of cell membrane surface morphology, making the observation easier. Preferably, a polypeptide that triggers a change of cell membrane surface morphology, or its partial recognition sequence, or more specifically the full-length or partial recognition sequence of G-protein coupled receptor (GPCR), c-Src, and/or the like, may be inserted between the C terminus of the luciferase itself and MLS. By inserting a cell-death-inducing polypeptide or its recognition sequence between the C terminus of the luciferase itself and MLS as a cargo, cell death can be visualized. More specifically, by inserting, as a cargo, a peptide sequence (usually of 20 or less amino acid residues, preferably of 10 or less amino acid residues) recognized by various caspases and proteases (such as serine protease and cysteine protease) and digestive enzymes (such as trypsin and amylase), or an amino acid sequence including a DEVD sequence (SEQ ID NO:90) or an IETD sequence (SEQ ID NO:91), cell death can be visualized by means of caspase-3 activity. Further, by linking a fluorescent protein or another luciferase between the polypeptide and MLS as a cargo, the amount of emission on the cell membrane surface is increased, enabling easier observation of cell membrane morphology. Because the luminescent capsule also responds to a ligand that does not permeate through the cell membrane, it enables screening for a wide range of stimulators.

The luminescent capsule is a luminescent fusion protein in which any protein or polypeptide intended to be expressed on the cell membrane surface is inserted between the C terminal side of the above-described polypeptide and a membrane localization signal (MLS), and typically, it may be either:

(a) a luminescent fusion protein in which a fluorescent protein or a luciferase (which may be an enzyme other than the above-described polypeptide) is inserted between the C terminal side of the polypeptide and a membrane localization signal (MLS); or (b) a luminescent fusion protein in which a polypeptide that triggers a change of cell membrane morphology, or a polypeptide of 20 or less amino acid residues, preferably of 10 or less amino acid residues, that is recognized by the above polypeptide is inserted between the C terminal side of the polypeptide and a membrane localization signal (MLS). As the polypeptide that triggers a change of cell membrane morphology, a polypeptide capable of inducing cell death is preferable, and caspase and a polypeptide of 20 or less amino acid residues that includes its recognition sequence "DEVD" (SEQ ID NO:90) or "IETD" (SEQ ID NO:91) are particularly preferable.

(ii) Application to Luminescent Probe

By incorporating the above-described polypeptide into a single-molecular luminescent probe or a bimolecular luminescent probe, it is possible to observe the presence or absence of a ligand and the intensity of the ligand activity, with a high luminance. The components of the probe may be coupled in such a manner that, [1] near luciferase that is divided into two parts (N terminus fragment and C terminus fragment), [2] a ligand-binding protein capable of responding to a target ligand and [3] a recognition protein capable of recognizing bonding of the ligand to the ligand-binding protein are coupled, and thereby a high-performance luminescent probe may be provided. When, in the luminescent probe, the recognition protein recognizes the bonding of the ligand to the ligand-binding protein, the two enzyme fragments can complement each other to change the activity of the enzyme. When this occurs, the high luminance and stability of this divided enzyme allows for an improved detection limit and a highly reliable measurement.

The single-molecular luminescent probe is a known bioluminescent probe characterized in that it has all of its visualization and imaging components in a single fusion molecule. One example is a fusion protein that includes, as its essential components, two portions into which the luciferase has been divided (N terminus fragment and C terminus fragment) as well as a ligand-binding protein and a recognition protein of the ligand-binding protein. The bimolecular luminescent probe refers to a type of bioluminescent probe in which the N terminus fragment and the C terminus fragment of the luciferase are present, respectively, in a fusion protein including a ligand-binding protein and in a fusion protein including a recognition protein.

The specific technique for using the above-described polypeptide as a single-molecular luminescent probe follows a known technique. Specifically, a chimeric DNA is designed that codes for a luminescent probe (a fusion protein) in which the first polypeptide and the second polypeptide are linearly bonded to a ligand-binding protein and a peptide sequence capable of recognizing a conformational change elicited by ligand-protein bonding. Typically, the chimeric DNA is subcloned into a vector that is suitable for the cell to be used for expression, and then the vector is introduced into the cell, followed by expression in the cell; alternatively, a regulatory sequence may be coupled to the upstream of the chimeric DNA for direct introduction into the cell. As the target cell, a cell derived from a mammal such as humans is preferable, and it may be a cell present in a living body or it may be a cultured cell that retains its original cellular function. It may be yeast cells, insect cells, and/or prokaryotic cells such as *Escherichia coli*. The specific type of the vector is not particularly limited, and a vector that allows for expression in an expression host may be selected as appropriate. As the method for introduction into the cell, a known transfection method such as microinjection and/or electroporation may be used. Alternatively, a lipid-based cell introduction method (such as BioPORTER (Gene Therapy Systems) and/or Chariot™ (protein delivery reagent, Active Motif)) may also be adopted.

Because a bioluminescent probe having the above-described polypeptide is introduced in the form of a chimeric DNA into a cell and then expressed as a fusion protein in the cell, by stimulating the transformed cell with a ligand and then measuring any change in the amount of emission from the cell, it is possible to evaluate the characteristics of the ligand, the extent of activity, and the like.

In the case of forming the above-described polypeptide within a bioluminescent probe, "the ligand-binding protein" eligible to be mounted together with the polypeptide may be a protein having a ligand-binding site capable of binding the ligand. The ligand-binding protein may, upon ligand bonding, undergo conformational change, or undergo phosphorylation, or facilitate protein-protein interactions, for example. As the ligand-binding protein of this type, a nuclear receptor (NR) whose ligand is a hormone, a chemical substance, or a signaling protein, a cytokine receptor, or a variety of protein kinases is used, for example. The ligand-binding protein is selected as appropriate depending on the target ligand. The ligand intended to bind to the ligand-binding protein is not particularly limited provided that it is capable of binding to the ligand-binding protein, and it may be an extracellular ligand that is taken from outside into inside the cell, or may be an intracellular ligand that is produced inside the cell upon extracellular stimulation. The extracellular ligand may be, for example, an agonist or an antagonist to a receptor protein (such as a nuclear receptor and/or a G protein-binding receptor, for example). It may also be a signaling protein such as a cytokine, a chemokine, or insulin, capable of specifically binding to a protein involved in intracellular signal transduction, an intracellular second messenger, a lipid second messenger, a phosphorylated amino acid residue, a G protein-binding receptor ligand, and/or the like.

When an intracellular second messenger, a lipid second messenger, and/or the like is targeted as the ligand, for example, the ligand-binding protein may be a binding domain of the second messenger. The "second messenger" is intended to mean an intracellular signal transduction substance that is newly produced in the cell upon bonding of an extracellular signal transduction substance such as a hormone and/or a neurotransmitter to a receptor present on the cell membrane. Examples of the second messenger include cGMP, AMP, PIP, PIP2, PIP3, inositol triphosphate (IP3), IP4, $Ca^{2+}$, diacylglycerol, and arachidonic achid. For example, for targeting $Ca^{2+}$ as a second messenger, calmodulin (CaM) may be used as the ligand-binding protein.

(iii) Bioluminescence Resonance Energy Transfer (BRET)

The above-described polypeptide may be used in any method intended to detect ligand-protein interactions or protein-protein interactions. Energy transfer from a luminescence donor to a fluorescence receptor causes a shift in the distribution of emission spectrum. This energy transfer allows for in vitro or in vivo real-time monitoring of protein-protein interactions or ligand-protein interactions. As an example, a fusion protein of the first polypeptide connected to a target molecule (such as a target protein and/or a ligand), and a fusion protein of a protein or a ligand capable of binding to the target molecule connected to a fluorescent protein are prepared, and, when they come close to the second polypeptide, a BRET signal is detected.

(iv) Protein Complementation Assay (PCA)

The above-described polypeptide may be used in a method for detecting ligand-protein interactions or protein-protein interactions or the proximity between them, such as protein complementation assay (PCA) or enzyme fragmentation assay. PCA provides a means for detecting interactions between two biomolecules, such as between two polypeptides. For example, the first polypeptide and the second polypeptide are fused, respectively, to molecules to be investigated proximity. When the target molecules interact with each other, the two polypeptide fragments interact with each other to form a complete luciferase, and thereby emission is detected.

(v) Intracellular Imaging

The gene coding for the above-described polypeptide can be stably introduced into various cell lines. Intracellular imaging with the use of the luciferase may be carried out by a known method. As an example, the polypeptide may be stably introduced into an undifferentiated cell in an embryo, an ES cell, and/or an induced pluripotent stem (iPS) cell. Because these cells do not emit luminescence themselves, it was very difficult to investigate molecular phenomena occurring inside or tissue specificity. To overcome this difficulty, first, a molecular probe containing the polypeptide is introduced into a somatic cell to prepare an embryo, which is then differentiated into a variety of organs and tissues. Thereby, it is possible to measure specific molecular phenomena occurring in each of these organs with a high sensitivity.

The above-described polypeptide may be coupled to a suitable signal peptide, and thereby may be used for high-luminance imaging of cell organelles. For example, an "MLCCMRRTKQV sequence" (SEQ ID NO: 63) derived from GAP-43 may be added to the N terminus or the C terminus of the polypeptide to enable localization to the cell membrane. A "GRKKRRQRRR sequence" (SEQ ID NO:

64) may be added to enable localization to the cytoplasm. "KDEL" (SEQ ID NO: 65) may be added to enable localization to endoplasmic reticula (ER), and a "DPKKKRKV sequence" (SEQ ID NO: 66) may be added to enable localization to the cell nucleus. An antigen site such as HIS-tag (HHHHHH) (SEQ ID NO: 67), FLAG-tag (DYKDDDDK) (SEQ ID NO: 68), Myc-tag (EQKLISEEDL) (SEQ ID NO: 69), HA-tag (YPYDVPDYA) (SEQ ID NO: 70), V5-tag (GKPIPNPLLGLDST) (SEQ ID NO: 71), and/or T7-tag (MASMTGGQQMG) (SEQ ID NO: 72) may be attached to allow for application for immunostaining and separation/purification in cell-free systems. In this case, known techniques such as immunostaining and immunocytochemistry are applicable.

Other terms and concepts herein are specified in detail in the description of the embodiments of the invention and in Examples. Each term is basically from IUPAC-IUB Commission on Biochemical Nomenclature, or is based on the meaning of the term widely used in the field. Moreover, various techniques used for implementing the invention, except for the techniques that are specifically presented with their sources, can be easily and surely implemented by a person skilled in the art based on known documents and the like. For example, genetic engineering and molecular biology techniques may be implemented by methods described in, for example, J. Sambrook, E. F. Fritsch & T. Maniatis, "Molecular Cloning: A Laboratory Manual (2nd edition)", Cold Spring Harbor Laboratory Press, Cold Spring Harbor, New York (1989); D. M. Glover et al. ed., "DNA Cloning", 2nd ed., Vol. 1 to 4, (The Practical Approach Series), IRL Press, Oxford University Press (1995); Ausubel, F. M. et al., Current Protocols in Molecular Biology, John Wiley & Sons, New York, N.Y, 1995; Edited by The Japanese Biochemical Society, "Second Series Biochemistry Laboratory Course 1, Genetic Research Method II" (which is, in Japanese, "Zoku-Seikagaku Jikken Kouza 1, Idenshi Kenkyu-hou II"), Tokyo Kagaku Dozin (1986); Edited by The Japanese Biochemical Society, "New Biochemistry Laboratory Course 2, Nucleic Acid III (Recombinant DNA technique)" (which is, in Japanese, "Shin-Seikagaku Jikken Kouza 2, Kakusan III (Kumikae DNA Gijutu)"), Tokyo Kagaku Dozin (1992); R. Wu ed., "Methods in Enzymology", Vol. 68 (Recombinant DNA), Academic Press, New York (1980); R. Wu et al. ed., "Methods in Enzymology", Vol. 100 (Recombinant DNA, Part B) & 101 (Recombinant DNA, Part C), Academic Press, New York (1983); R. Wu et al. ed., "Methods in Enzymology", Vol. 153 (Recombinant DNA, Part D), 154 (Recombinant DNA, Part E) & 155 (Recombinant DNA, Part F), Academic Press, New York (1987); or methods described in references cited by these, or methods substantially the same as those, or modifications thereof. Further, various proteins and peptides, and DNAs coding for them, used in the present invention are available from existing database such as the National Center for Biotechnology Information database.

EXAMPLES

Figure 4:
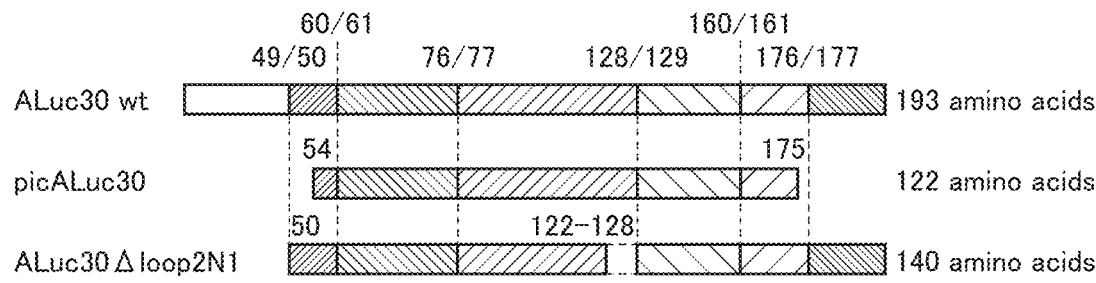
FIG. 4 is a schematic view illustrating the structure of an ALuc30 variant prepared in Examples.

Next, a more detailed description will be given of the present invention referring to Examples, which are not intended to limit the scope of the present invention.
Experiment 1: Preparation of picALuc Plasmid A luciferase that had an amino acid sequence corresponding to positions 20 to 221 of SEQ ID NO: 1 and also had an amino acid sequence of positions 20 to 212 of ALuc30 (SEQ ID NO: 28) (without a signal sequence) was defined as ALuc30 wt. The sequence of ALuc30 wt is shown in FIG. 4. The molecular weight of ALuc30 wt is about 21 kDa.

ALuc consists of two helix structures, a loop structure, a helix structure, a (helix structure)-(loop structure)-(helix structure), two small helix structures, a helix structure, and a small helix structure, in this order from the N terminus. As shown in FIG. 4, picALuc30 (SEQ ID NO: 51) including amino acids at positions 54 to 175 of ALuc30 wt, without the N terminus and the C terminus of ALuc30 wt was prepared. picALuc30 was inserted into a pcDNA3.1(+) vector (Thermo Fisher Scientific™, Waltham, MA). In the same manner, with the use of ALuc16 (SEQ ID NO: 15) and ALuc48 (SEQ ID NO: 40) instead of ALuc30, expression plasmids picALuc16 (SEQ ID NO: 52) and picALuc48 (SEQ ID NO: 53) each having an amino acid sequence corresponding to picALuc30 were prepared. picALuc30 had a size of 13 kDa. To the N terminus of each variant, His-tag was added, and to the C terminus, Flag-tag was added. "picALuc" herein corresponds to "miniALuc" recited in a priority application JP2021-084687.

Figure 6:
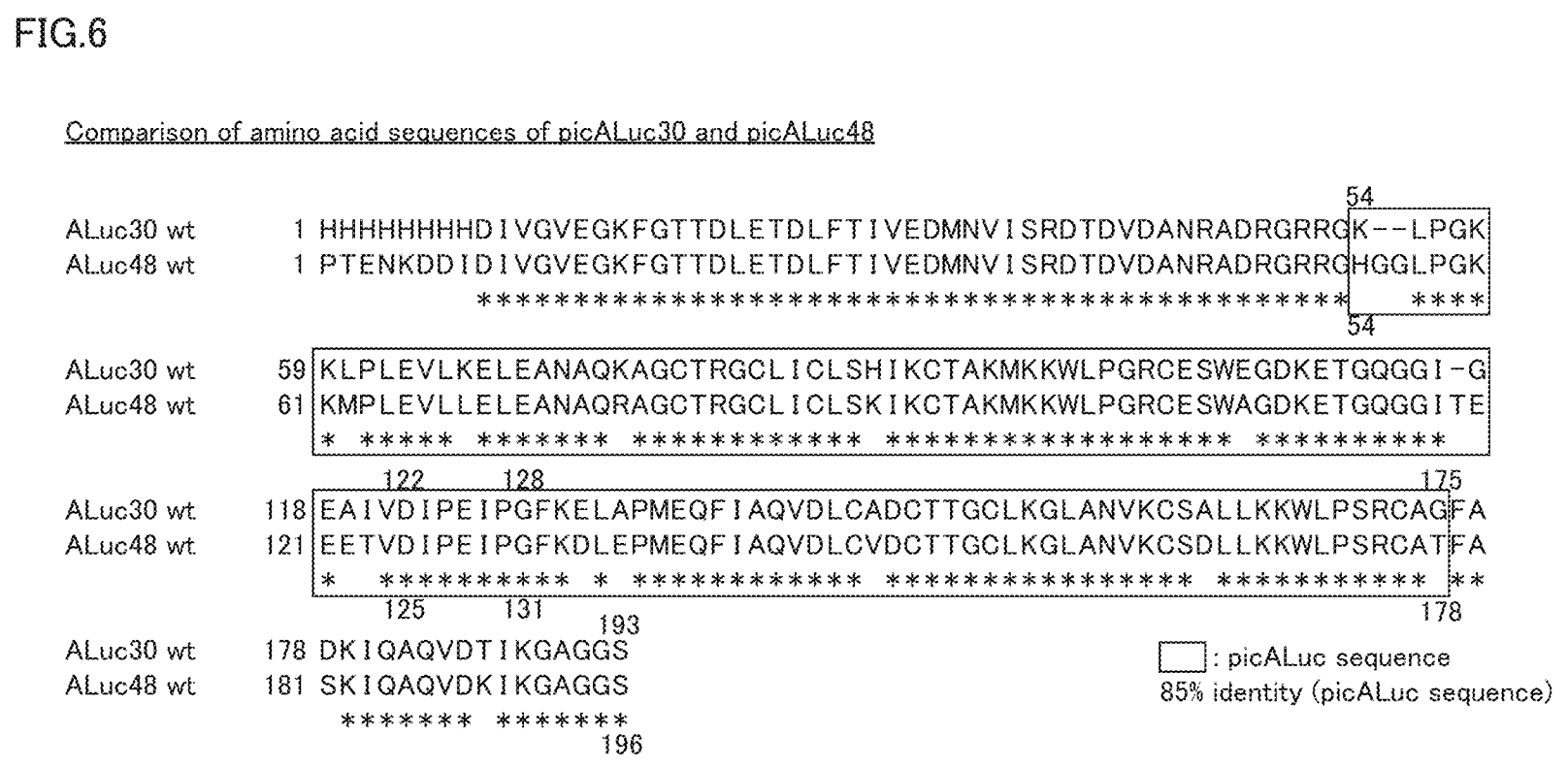

The amino acid sequences of picALuc30 (SEQ ID NO:51) and picALuc16 (SEQ ID NO:52) had 96% identity (FIG. 5); the amino acid sequences of picALuc30 (SEQ ID NO:51) and picALuc48 (SEQ ID NO:53) had 85% identity (FIG. 6); and the amino acid sequences of picALuc48 (SEQ ID NO:53) and picALuc16 (SEQ ID NO:52) had 90% identity (FIG. 7).
Experiment 2: Measurement of Emission Value of picALuc (1) COS-7 cells derived from the kidney of African green monkey were inoculated in a 24-well dish, and on the next day, subconfluency was attained.

(2) 25 μL of Opti-MEM (Thermo Fisher Scientific™), 400 ng (2 μL) of the plasmid, and 1 μL of P3000 (Invitrogen™, Waltham, MA) were mixed.

(3) 25 μL of Opti-MEM and 1 μL of lipofectoamine 3000 (Invitrogen™) were mixed.

(4) (2) and (3) were mixed together, followed by incubation at room temperature for 5 minutes.

(5) The mixture was added to the medium of (1).

(6) 500 μL of Dulbecco's modified Eagle's medium was added, followed by culturing the cells at 37° C. for 1 day and then collecting the medium. The medium contained secretion-expressed luciferase.

Figure 8:
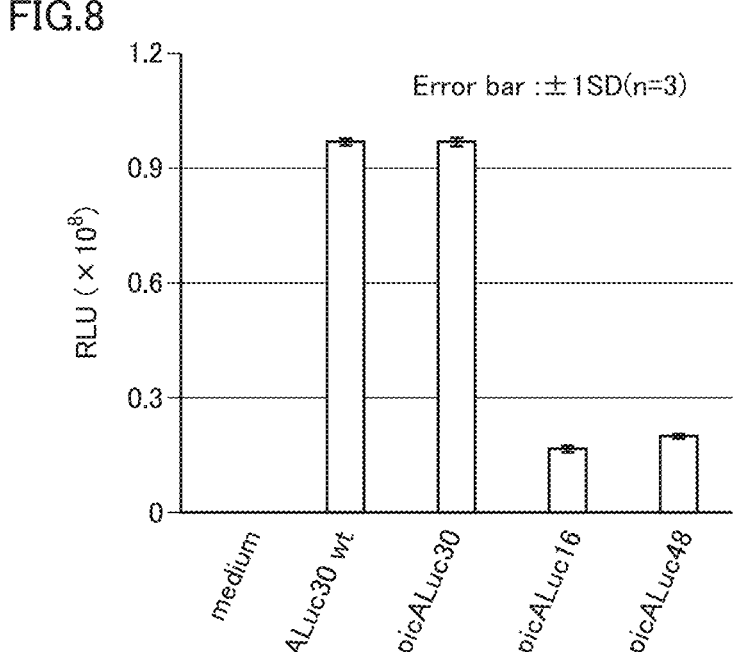
FIG. 8 is a graph showing the emission value of picALuc in Experiment 2.
Figure 9:
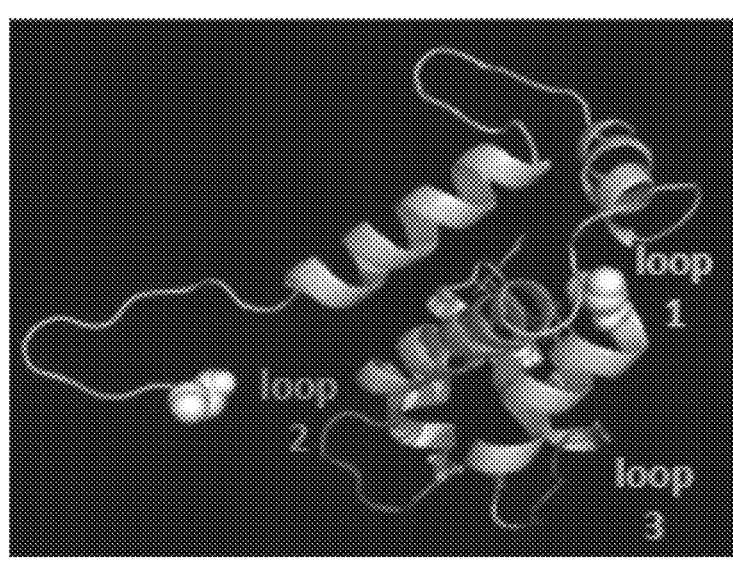
FIG. 9 shows the conformation of picALuc30.

(7) To 100 μL of the medium, coelenterazine was added as a substrate at a final concentration of 5 μM, followed by measuring the emission value by using Enspire multi-mode plate reader (PerkinElmer™, Waltham, MA).

picALuc30 exhibited an emission value the same as or higher than that of ALuc30 wt (FIG. 8). For both picALuc16 and picALuc48, sufficiently high emission values were measured.
Experiment 3: Preparation of ΔLoop Plasmid A putative conformation of picALuc30 is shown in FIG. 9. picALuc30 had a plurality of loop structures. Among these, the amino acid sequences for three loops (loop 1, loop 2, and loop 3) were deleted to prepare variants. An amino acid sequence for loop 1 (position 96 to position 100 of ALuc30 wt), that for loop 2 (position 122 to position 128 of ALuc30 wt), or that for loop 3 (position 156 to position 161 of ALuc30 wt) was deleted from ALuc30 wt, and Gly-Ser was inserted. Further, the N terminus of ALuc30 wt (position 1 to position 49) was also deleted. Thus, expression plasmids ALuc30Δloop1N1, ALuc30Δloop2N1 (SEQ ID NO: 54), and ALuc30Δloop3N1, in each of which the N terminus and a loop were deleted, were prepared. ALuc30Δloop2N1 had a size of 14 kDa.

Experiment 4: Measurement of Emission Value of ALucΔLoop

Figure 10:
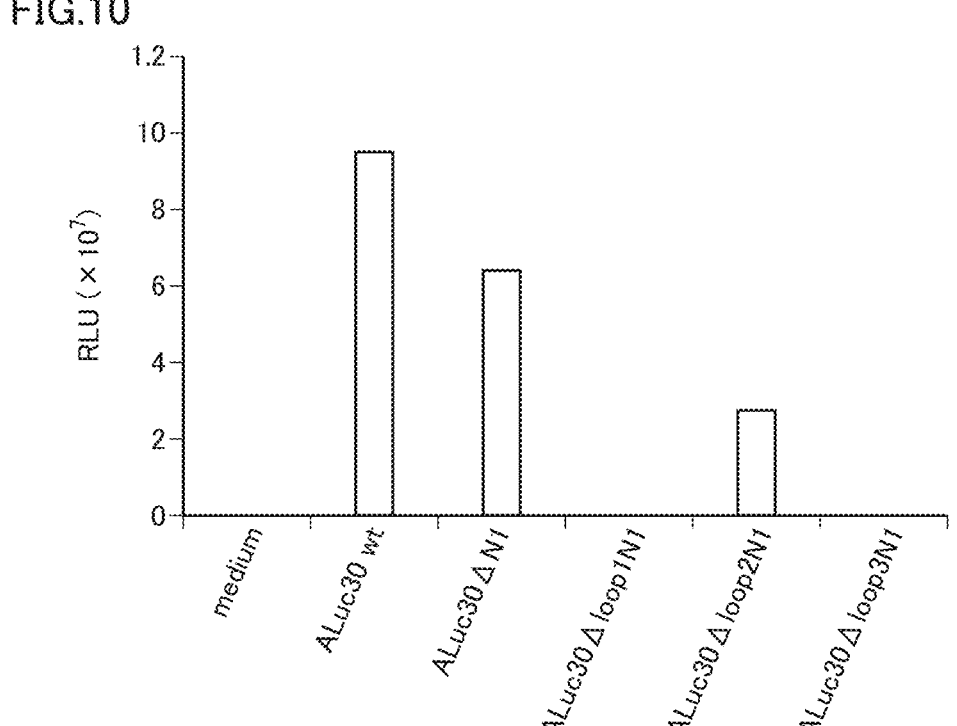
FIG. 10 is a graph showing the emission value of ΔloopN1 in Experiment 4.

By the same manner as in Experiment 2, the emission value was measured. ALuc30Δloop2N1 had about half the emission value of ALuc30ΔN1, which only lacked the N terminus as compared thereto (FIG. 10). The emission values of ALuc30Δloop1N1 and ALuc30Δloop3N1 were markedly low.

Experiment 5: Comparison with Known Luciferases picALuc prepared in Experiment 1 was compared with known NanoLuc®, TurboLuc™, and GLuc. NanoLuc® is known to have a small size of about 19 kDa, a very high emission value, and a high thermal stability. TurboLuc™ is known to have a small size of about 16 kDa, a relatively high emission value, and a high thermal stability. GLuc is known to have a small size of 20 kDa, and when it is secretion expressed from cells, have a low emission value as compared to ALuc, and have a high thermal stability. As NanoLuc®, TurboLuc™, and GLuc, plasmids having sequences in SEQ ID NO: 73, SEQ ID NO: 74, and SEQ ID NO: 75, respectively, inserted into a pcDNA3.1 vector were used.

Figure 11:
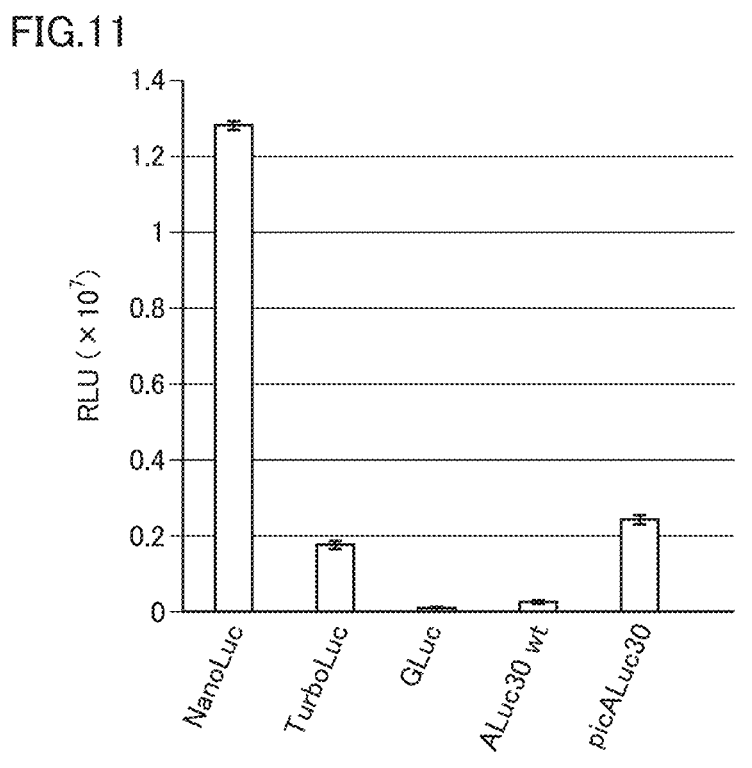
Figure 12:
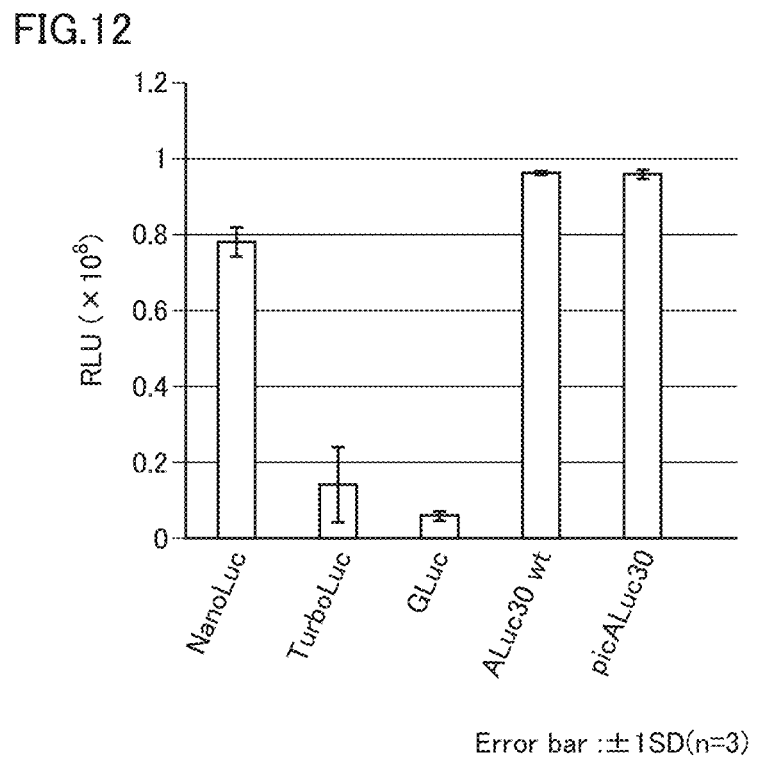

The emission value was measured in the same manner as in Experiment 2 except that the final concentration of coelenterazine was changed to 0.5 μM. The emission values were as follows: NanoLuc®>>picALuc30>TurboLuc™>ALuc30 wt>GLuc (FIG. 11). The emission value was measured in the same manner as in Experiment 2 except that the final concentration of coelenterazine was changed to 5 μM. The emission values were as follows: ALuc30 wt=picALuc30>NanoLuc®>TurboLuc™>GLuc (FIG. 12).

Figure 13:
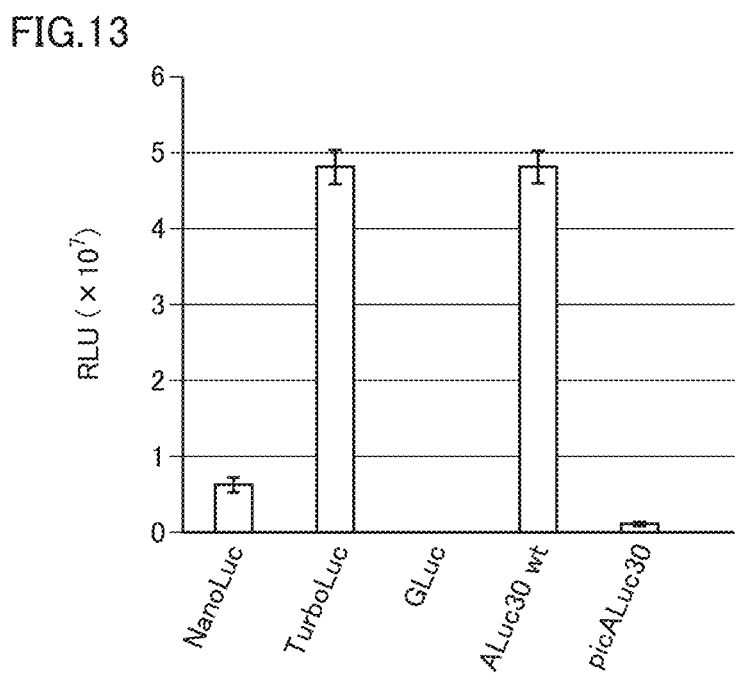
Figure 14:
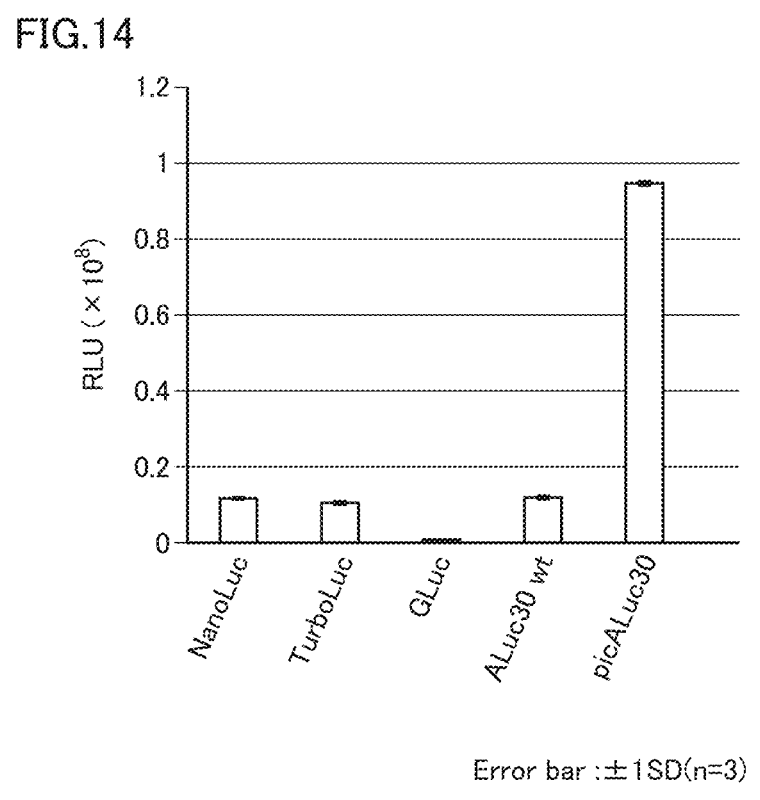

The emission value was measured in the same manner as in Experiment 2 except that coelenterazine h was used as a substrate in a final concentration of 5 μM. The emission values were as follows: TurboLuc™=ALuc30 wt>>NanoLuc®>picALuc30>GLuc (FIG. 13). The emission value was measured in the same manner as in Experiment 2 except that coelenterazine h was used as a substrate in a final concentration of 25 μM. The emission values were as follows: picALuc30>>NanoLuc®=TurboLuc™=ALuc30 wt>>GLuc (FIG. 14).

Figure 15:
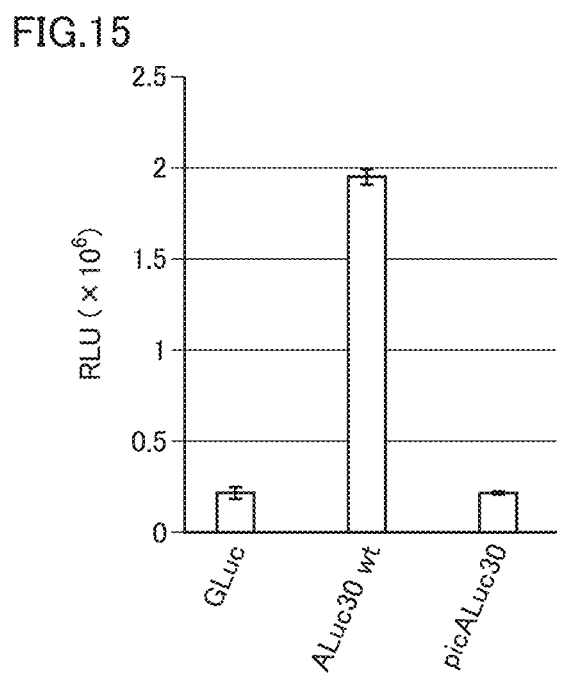
Figure 16:
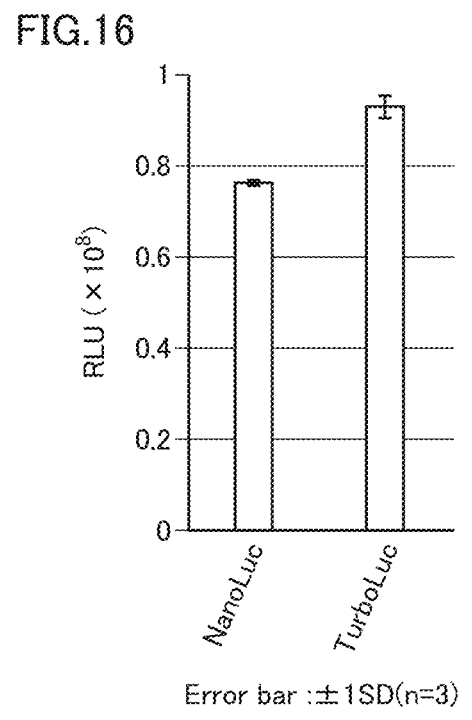

The emission value was measured in the same manner as in Experiment 2 except that furimazine, which was available from Promega™ as a NanoLuc® substrate, was used as a substrate in the concentration recommended by the manufacturer. Emission was detected with GLuc, ALuc30 wt, and picALuc30, which was low as compared to NanoLuc® and TurboLuc™ (FIG. 15 and FIG. 16). NanoLuc® and TurboLuc™ exhibited high emission values, where the emission value of NanoLuc® was the same as when coelenterazine or coelenterazine h was used (FIG. 16).

The above results suggested that coelenterazine and coelenterazine h were more suitable than furimazine as a substrate for picALuc30, and that secretion-expressed picALuc30, when reacted with substrate coelenterazine or coelenterazine h in a high concentration, exhibited an emission value that was equal to or higher than NanoLuc® and TurboLuc™.

Experiment 6: Stability of Protein Terminus

Figure 17:
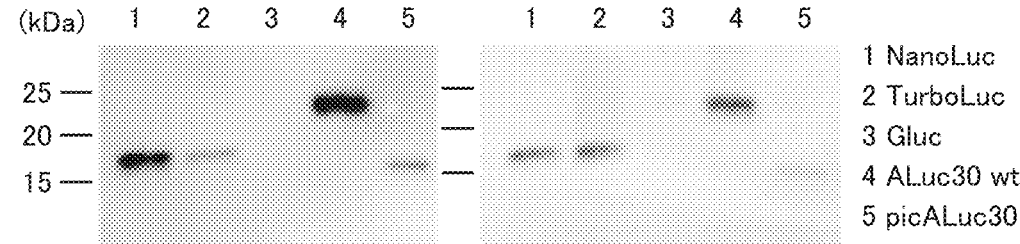
FIG. 17 shows Western blot detection of enzyme protein in supernatant in Experiment 6. The left shows flag-tag detection, and the right shows His-tag detection.

In the same manner as in Experiment 2, the plasmid was transfected into COS-7 cells and culture supernatant was collected. Flag-tag added to the N terminus of each secretion-expressed luciferase and His-tag added to the C terminus thereof were detected by Western blotting (SDS-PAGE, Mini-PROTEAN TGX Gel StainFree 4-15% (Bio-Rad™, Hercules, CA)) (FIG. 17). The antibodies used were Anti 6×Histidine, Monoclonal Antibody (9C11), Peroxidase Conjugated (manufactured by FUJIFILM Wako Pure Chemical Corporation, 1:1000) and Monoclonal ANTI-FLAG (R) M2-Peroxidase (HRP) antibody produced in mouse, clone M2 (manufactured by Sigma-Aldrich™, St. Louis, MO, 1/1000), respectively, and detection was performed with Amesham Imager 680 (Cytiva™, Marlborough, MA). Flag-tag and His-tag on GLuc were lower than the detection limit. Signal intensity comparison between Flag-tag and His-tag on GLuc and TurboLuc™ indicated that Flag-tag on Tur-boLuc™ gave a low detection value and its N terminus was lost. In contrast, ALuc30 wt and picALuc30 had their both termini remaining, and showed high stability as compared to GLuc and TurboLuc™.

Experiment 7: Measurement of Specific Activity

Figure 18:
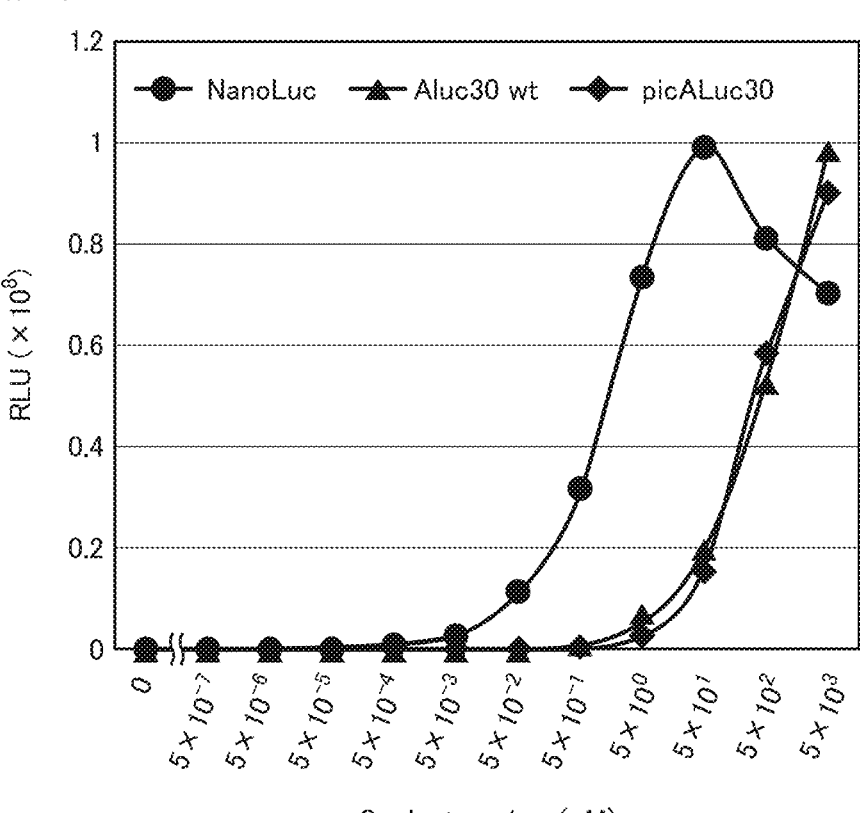
FIG. 18 is a graph of specific activity obtained when coelenterazine was used as a substrate in Experiment 7.
Figure 19:
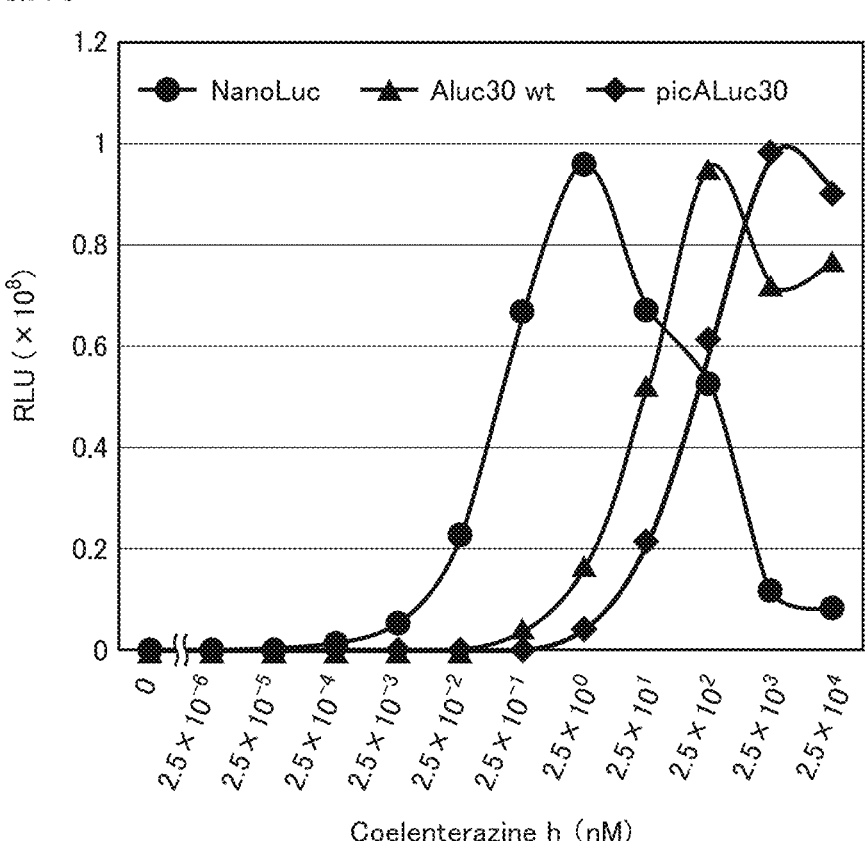
FIG. 19 is a graph of specific activity obtained when coelenterazine h was used as a substrate in Experiment 7.

The specific activities of NanoLuc®, ALuc30 wt, and picALuc30 were measured, with their enzyme concentrations adjusted based on the Western blot signal intensity obtained in Experiment 6. When coelenterazine or coelenterazine h was reacted as a substrate, the specific activity of ALuc was the same as the specific activity of picALuc (FIG. 18 and FIG. 19). ALuc30 wt and picALuc30 had the same maximum emission value as NanoLuc®, indicating that they had high emission activities.

Figure 20:
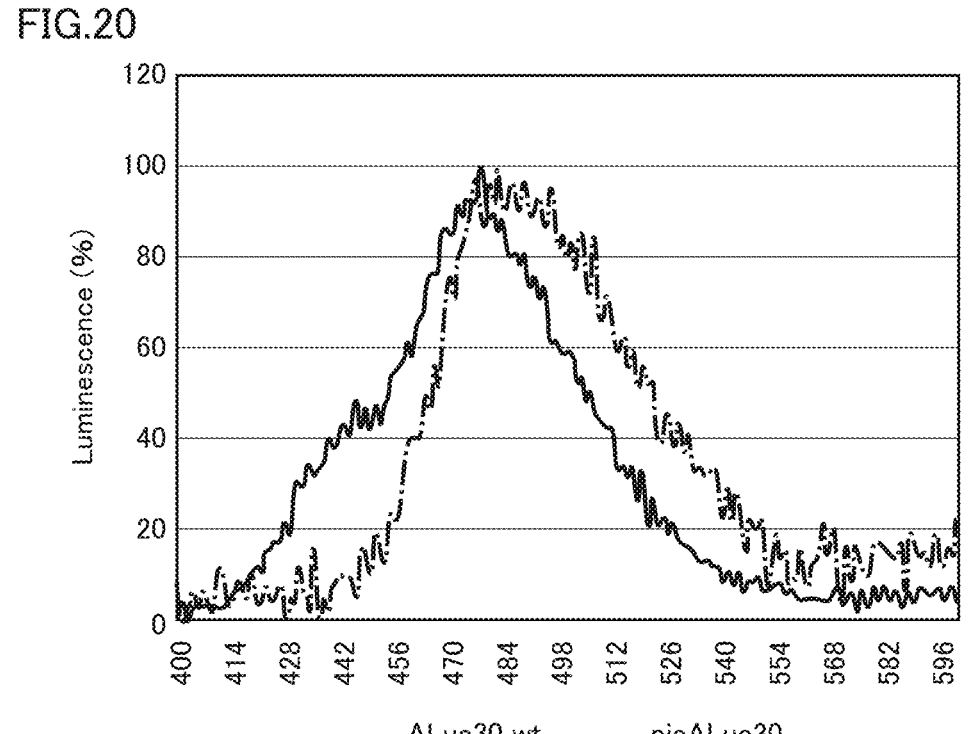
FIG. 20 shows emission spectra obtained when coelenterazine was used as a substrate in Experiment 8.
Figure 21:
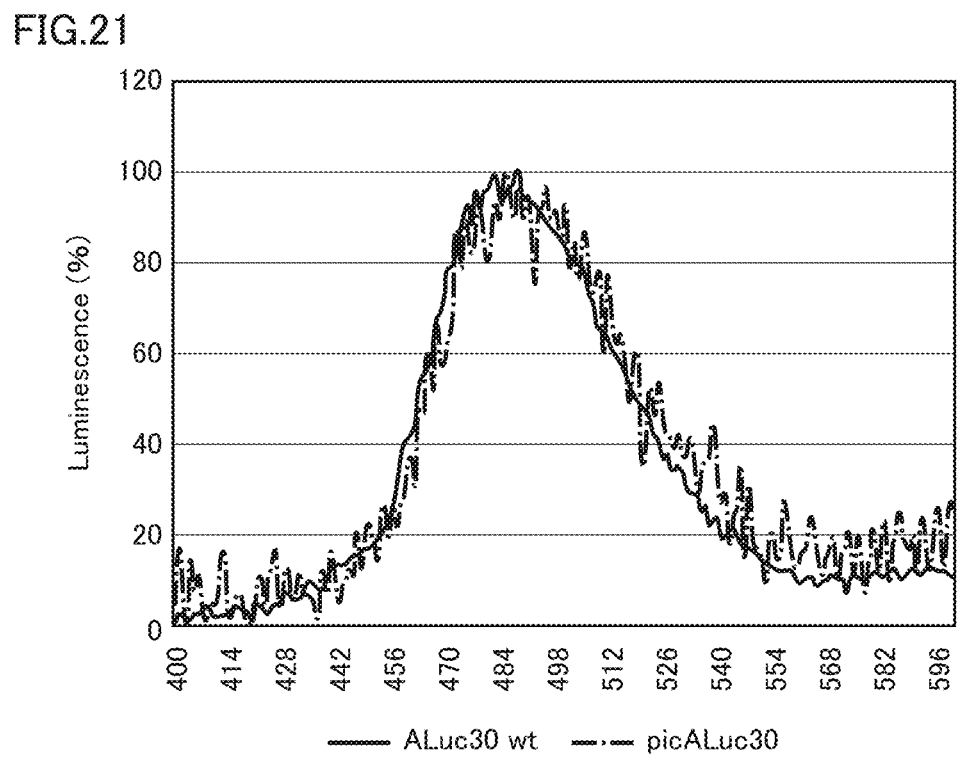

Experiment 8: Measurement of Emission Spectrum picALuc30 showed a wavelength peak at 482 nm when reacted with coelenterazine (FIG. 20), and at 488 nm when reacted with coelenterazine h (FIG. 21). picALuc30 showed a wavelength peak approximately the same as ALuc30 wt. The emission spectrum had a characteristic wider tail on the longer wavelength side than on the shorter wavelength side.

Experiment 9: Investigation of Thermal Stability

Figure 22:
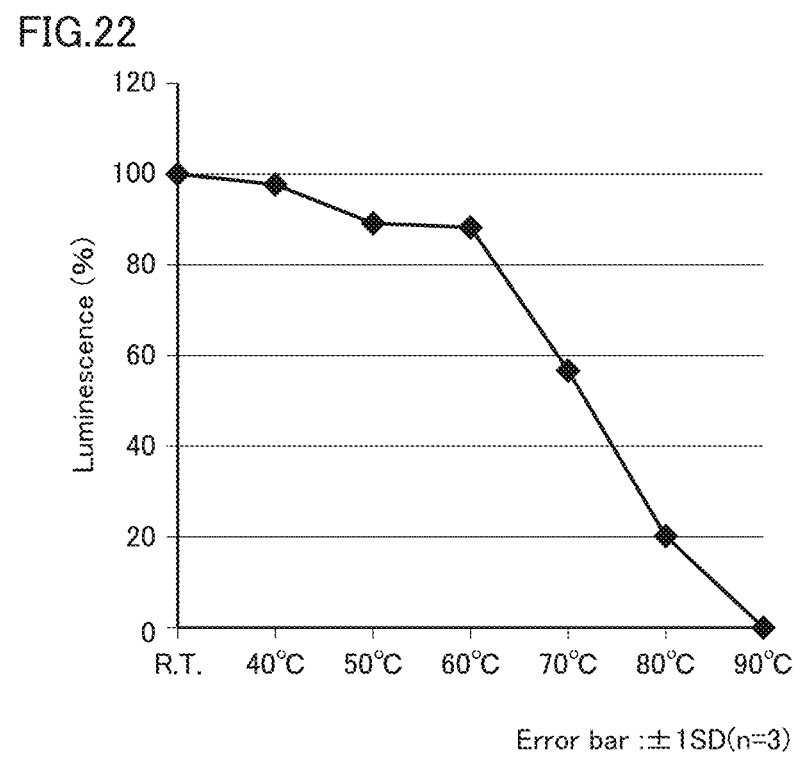

In the same manner as in Experiment 2, the plasmid was transfected into COS-7 cells and the medium was collected. The culture supernatant containing picALuc30 was incubated for 10 minutes at room temperature (25° C.), 40° C., 50° C., 60° C., 70° C., 80° C., or 90° C., and then the emission value was measured. Results showed that 80% or more of the activity remained after 10-minute incubation at 50° C. or 10-minute incubation at 60° C., and 50% or more remained after 10-minute incubation at 70° C. (FIG. 22), indicating a sufficient level of practical utility.

Experiment 10: Luciferase Expression in *Escherichia coli*

(1) A DNA sequence coding for picALuc30 was inserted into a pET32 vector to prepare a plasmid. Transformation was carried out into *Escherichia coli* SHuffle T7 express lysY (New England Biolab).

(2) *Escherichia coli* from (1) was inoculated into an LB plate (containing 100 μg/μL of ampicillin).

(3) Next day, one colony was taken out, and cultured with shaking overnight at 30° C. in a test tube containing 2 mL of LB medium (containing 100 μg/μL of ampicillin).

(4) 1 mL of (3) was added to 100 mL of LB medium (containing 100 μg/μL of ampicillin), followed by shaking culture at 30° C. in a 500-mL flask until the absorbance $OD_{600}$ reached about 0.4.

(5) When the absorbance $OD_{600}$ reached about 0.4, 40 μL of 1-M isopropyl-β-thiogalactopyranoside was added, followed by overnight culture at 16° C.

(6) The bacterial cells were collected, followed by purification of the protein using HisTALON Buffer Set and TALON Metal Affinity Resin (both from Takara Bio Inc.). From 100 mL of the medium, 1.7 mg of picALuc30 was obtained.

Figure 23:
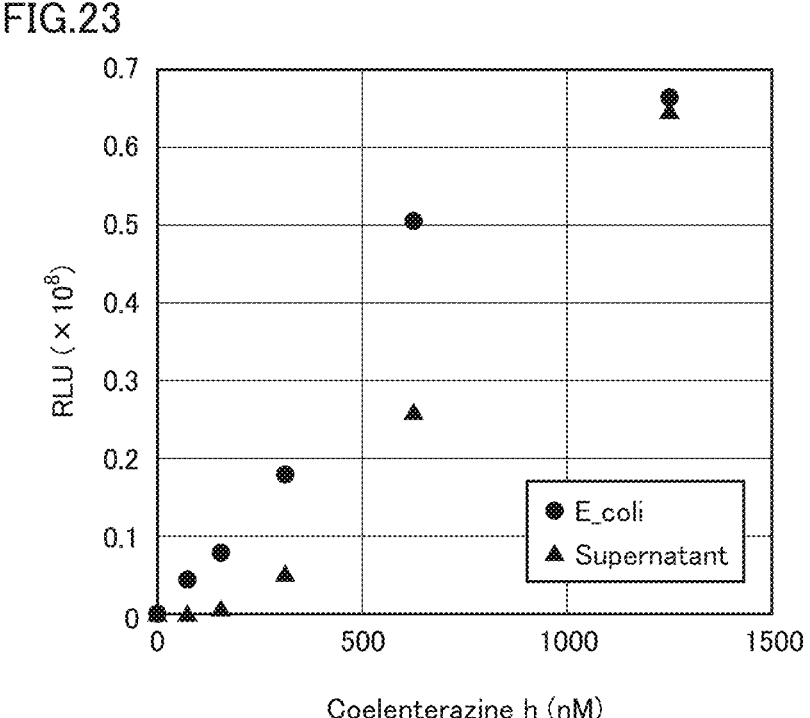
FIG. 23 is a graph showing the emission values of picALuc that was secretion-expressed and picALuc that was expressed in Escherichia coli in Experiment 10.

Specific activity was measured with the concentrations adjusted by way of Western blotting, and results showed that the specific activity of picALuc30 secretion expressed by COS-7 cells was approximately the same as the specific activity of picALuc30 prepared in *Escherichia coli* (FIG. 23). It indicates that picALuc30 can be not only secretion-expressed from mammalian cells but also expressed in *Escherichia coli*, and also a large-scale production is possible.

picALuc30 purified from *Escherichia coli* was incubated for 10 minutes at room temperature (25° C.), 60° C., 70° C., 80° C., or 90° C., followed by measurement of the emission value (FIG. 24). picALuc30 expressed in *Escherichia coli* lost little activity after 10-minute incubation at 60° C.; 90% or more of the activity remained after 10-minute incubation at 70° C., and 80% or more of the activity remained after 10-minute incubation at 80° C., indicating its excellent thermal stability.

Experiment 11-1: Emission Activity of Divided Enzyme picALuc30 was divided to prepare plasmids (pET32 vectors) for expression of polypeptides from position 4 to 22, from position 23 to 120, from position 4 to 47, from position 48 to 120, from position 4 to 77, from position 80 to 120, from position 4 to 90, and from position 91 to 120 of the amino acid sequence in SEQ ID NO: 51. In the same manner as in Experiment 10, the plasmid was introduced into *Escherichia coli* SHuffle T7 Express lysY, and from the cultured bacterial cells, a lysate was obtained. To 100 µL of a single lysate or a mixture of lysates as specified in FIG. 25, coelenterazine was added as a substrate at a final concentration of 5 µM, followed by measuring the emission value by using an Infinite (registered trademark) 200 PRO plate reader (TECAN). Because the lysate contained luciferase fragments at high concentrations, it was expected that when fragment-containing lysates were mixed, two types of fragments were highly likely to encounter each other and these two fragments could form the original luciferase structure.

Figure 25:
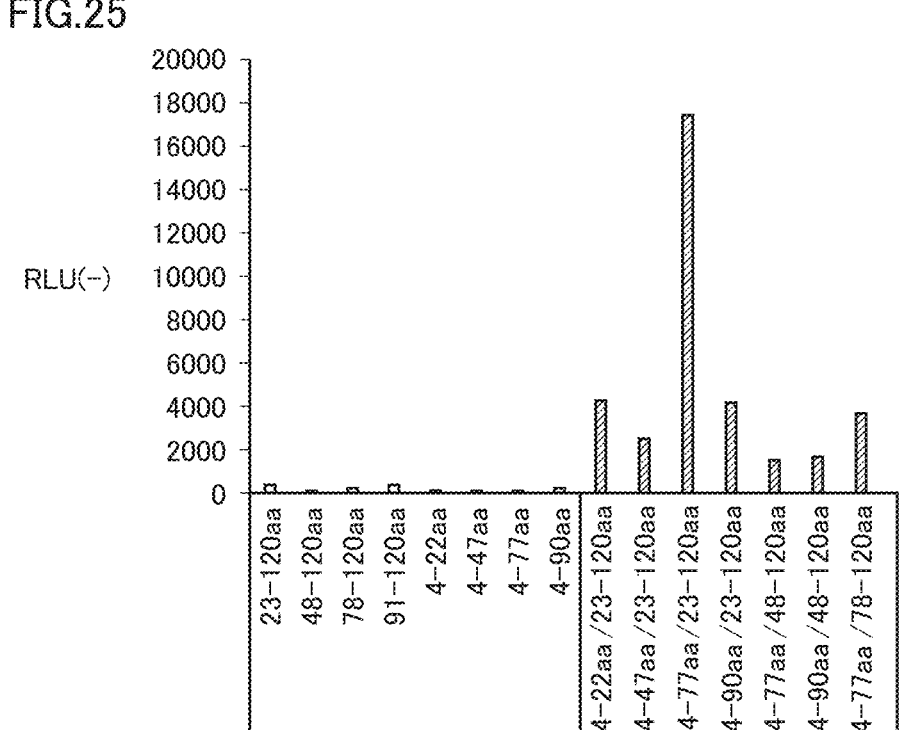
FIG. 25 is a graph showing the emission values of divided picALuc and combinations thereof in Experiment 11-1.

As shown in FIG. 25, single lysates each containing a luciferase fragment polypeptide gave low emission values, while a mixture of a plurality of lysates gave a high emission value as compared to the single lysates. Neither a combination of a polypeptide consisting of an amino acid sequence from position 4 to 22 of the amino acid sequence in SEQ ID NO: 51 and a polypeptide consisting of an amino acid sequence from position 23 to 120 of the same (Combination 1), nor a combination of a polypeptide consisting of an amino acid sequence from position 4 to 77 of the same and a polypeptide consisting of an amino acid sequence from position 78 to 122 of the same (Combination 2) has any overlapping between the amino acid sequences, and each combination, when in the form of combination, has the same sequence as that of picALuc30 with deletion of three N-terminal amino acid residues and two C-terminal amino acid residues. A combination of a polypeptide consisting of an amino acid sequence from position 4 to 77 of the amino acid sequence in SEQ ID NO: 51 and a polypeptide consisting of an amino acid sequence from position 23 to 120 of the same (Combination 3) has partial overlapping between the amino acid sequences, but it gave a high emission value. It is shown that a polypeptide (first polypeptide) containing a partial luciferase sequence and not having luciferase activity, in the presence of another polypeptide (second polypeptide) containing a partial luciferase sequence and not having luciferase activity, exhibits luciferase activity.

Experiment 11-2: Emission Activity of Divided Enzyme picALuc30 was divided to further prepare plasmids (pET32 vectors) for expression of polypeptides from position 4 to 58, from position 4 to 64, from position 4 to 72, from position 65 to 120, from position 73 to 120, and from position 104 to 120 of the amino acid sequence in SEQ ID NO: 51. In Experiment 11-2, emission values were measured in the same manner as in Experiment 11-1 except that an Enspire multi-mode plate reader (PerkinElmer™) was used for emission value detection.

Figure 26:
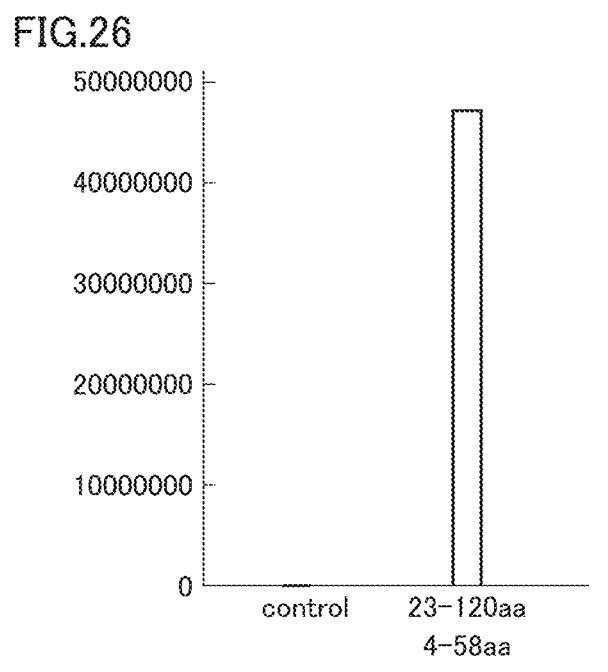
Figure 27:
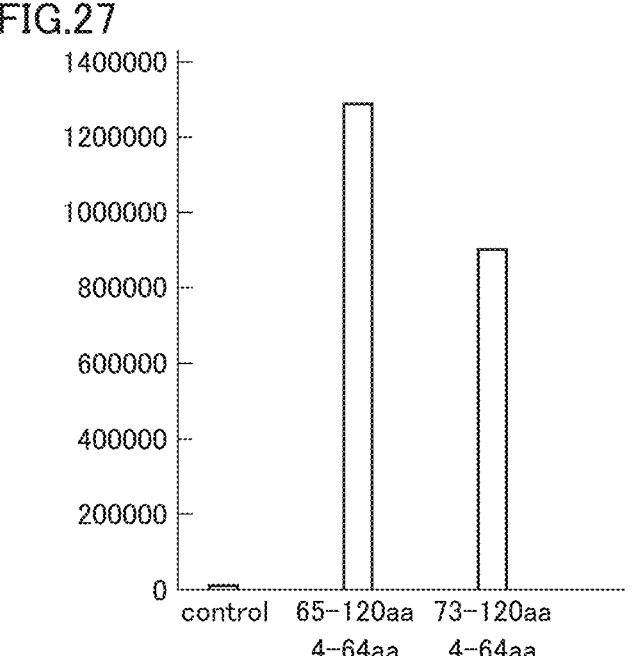
FIG. 27 is a graph showing the emission values of divided picALuc and combinations thereof in Experiment 11-2.
Figure 28:
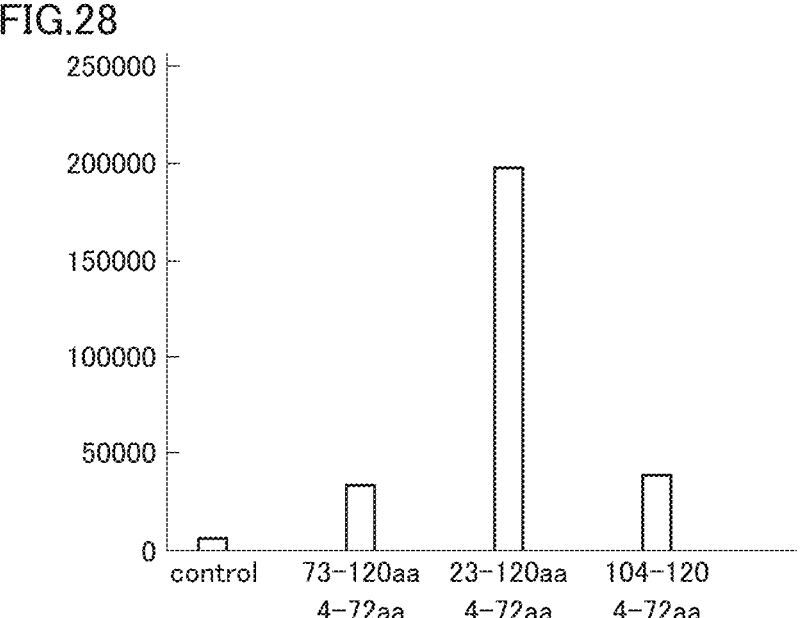
FIG. 28 is a graph showing the emission values of divided picALuc and combinations thereof in Experiment 11-2.
Figure 29:
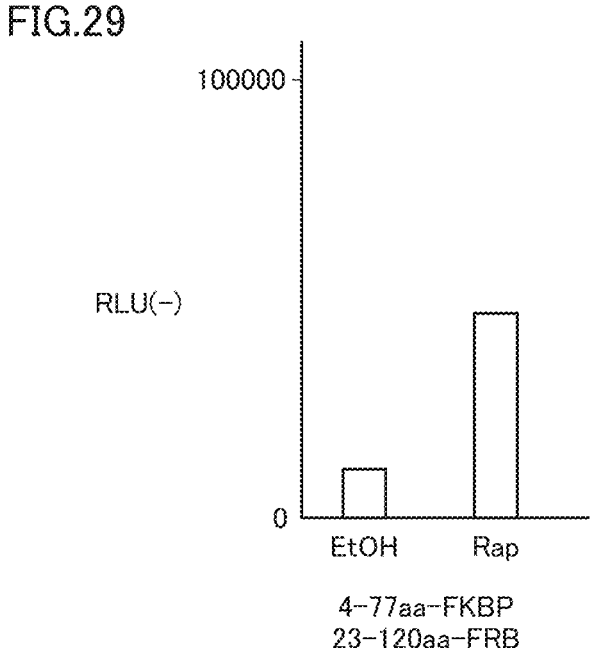
FIG. 29 is a graph showing results of detecting interactions between two molecules with the use of divided picA-Luc in Experiment 12.
Figure 30:
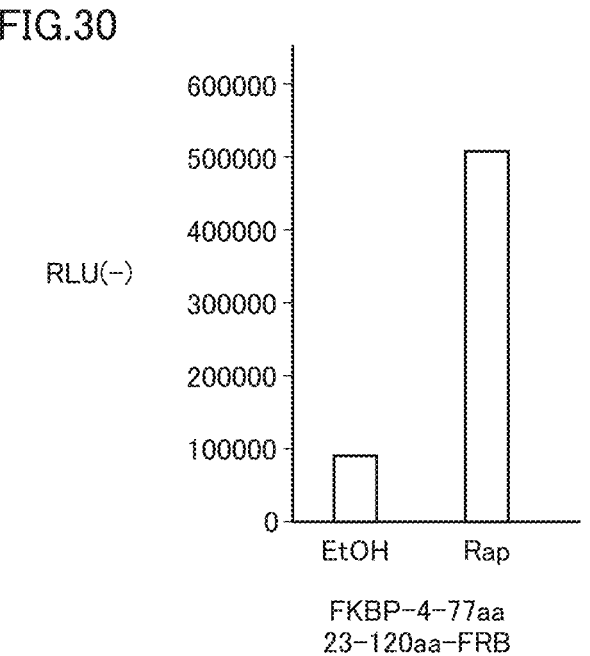
FIG. 30 is a graph showing results of detecting interactions between two molecules with the use of divided picA-Luc in Experiment 12.
Figure 31:
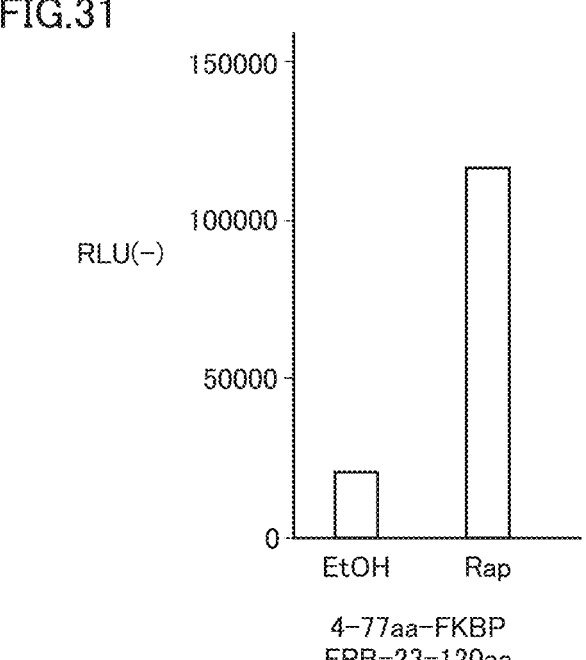
FIG. 31 is a graph showing results of detecting interactions between two molecules with the use of divided picA-Luc in Experiment 12.
Figure 32:
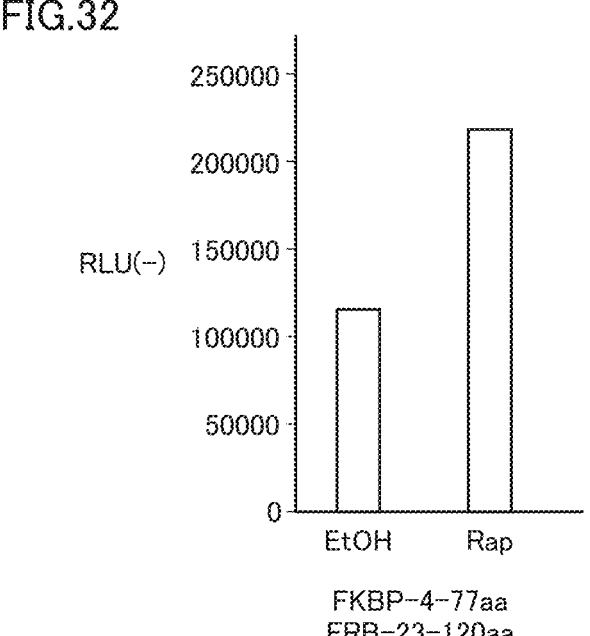
FIG. 32 is a graph showing results of detecting interactions between two molecules with the use of divided picA-Luc in Experiment 12.
Figure 33:
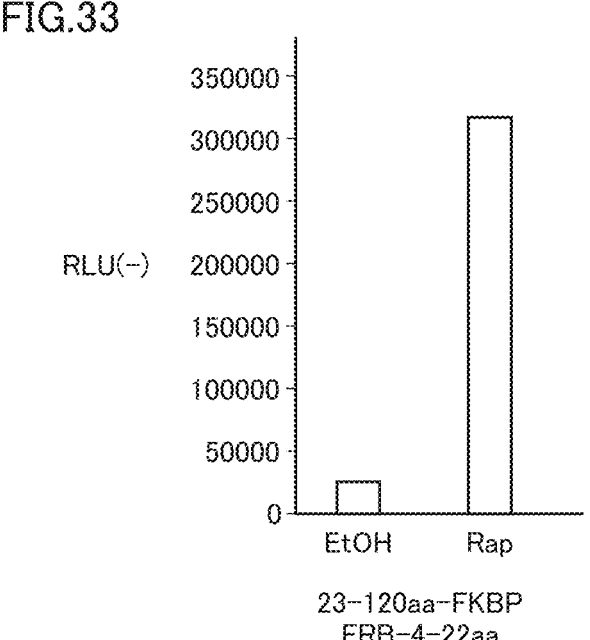
FIG. 33 is a graph showing results of detecting interactions between two molecules with the use of divided picA-Luc in Experiment 12.
Figure 36:
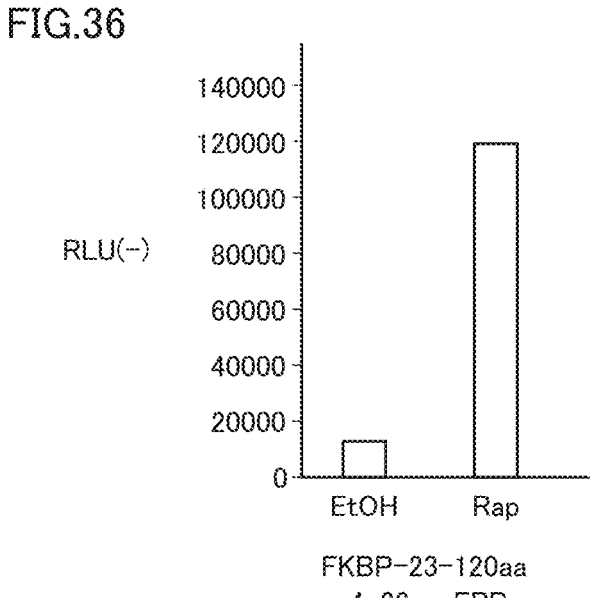
FIG. 36 is a graph showing results of detecting interactions between two molecules with the use of divided picA-Luc in Experiment 12.

The combination of a polypeptide consisting of an amino acid sequence from position 4 to 58 of the amino acid sequence in SEQ ID NO: 51 and a polypeptide consisting of an amino acid sequence from position 23 to 120 of the same gave a high emission value (FIG. 26). The combination of a polypeptide consisting of an amino acid sequence from position 4 to 64 of the amino acid sequence in SEQ ID NO: 51 and a polypeptide consisting of an amino acid sequence from position 65 to 120 or from position 73 to 120 of the same gave a high emission value (FIG. 27). The combination of a polypeptide consisting of an amino acid sequence from position 4 to 72 of the amino acid sequence in SEQ ID NO: 51 and a polypeptide consisting of an amino acid sequence from position 73 to 120, or from position 23 to 120, or from position 104 to 120 of the same gave a high emission value (FIG. 28).

Experiment 12: Intermolecular Interaction Detection Using Divided Luciferase

FKBP (FK506-binding protein) and FRB (FKBP12-rapamycin-associated protein 1), which are known to bind in a rapamycin (Rap) dependent manner, were used to investigate if intermolecular interactions could be detected by means of divided luciferase. The above-described polypeptide combinations 1 and 3 were used in the investigation. First, a fusion protein having FKBP connected to the N terminus or the C terminus of an amino acid sequence from position 4 to 77 of the amino acid sequence in SEQ ID NO: 51 (FKBP-4-77aa, 4-77aa-FKBP), a fusion protein having FRB connected to the N terminus (FRB-4-77aa); a fusion protein having FRB connected to the N terminus or the C terminus of an amino acid sequence from position 4 to 22 of the amino acid sequence in SEQ ID NO: 51 (FRB-4-22aa, 4-22aa-FRB); a fusion protein having FKBP connected to the N terminus or the C terminus of an amino acid sequence from position 23 to 120 of the amino acid sequence in SEQ ID NO: 51 (FKBP-23-120aa, 23-120aa-FKBP), and a fusion protein having FRB connected to the N terminus or the C terminus (FRB-23-120aa, 23-120aa-FRB) were prepared. The polypeptide was connected to FKBP or FRB via a linker sequence (SEQ ID NO: 87). The sequences of FKBP and FRB are in SEQ ID NO: 88 and SEQ ID NO: 89, respectively.

A plasmid coding for the above-described fusion protein (pET32 vector) was introduced into *Escherichia coli* to make it express the fusion protein. The *Escherichia coli* was collected, followed by protein purification with the use of an HisTALON Buffer Set (Clontech™) and a TALON Metal Affinity Resin (Clontech™). The emission values were measured. To the purified fusion protein, rapamycin was added at a concentration of 50 nM. Ethanol was used as a negative control. Other experiment procedures were the same as in Experiment 11-2.

As shown in FIGS. 29 to 36, the fusion protein combinations gave high emission values in the presence of rapamycin. It was shown that a polypeptide containing a partial luciferase sequence and not having luciferase activity (first polypeptide) was suitably usable in combination with the second polypeptide, for detecting interactions between two molecules or detecting the presence of an interaction-inducing molecule. It was also shown that interactions were detected regardless of which of the N terminus or the C terminus of the target protein the polypeptide was attached to.

Experiment 13: Intermolecular Interaction Detection Using Divided Luciferase

FKBP, FRB, and divided polypeptide portions were connected together via linker sequences to prepare a fusion protein. This fusion protein is a circular permutated variant in which: FRB is connected to the N terminus of an amino acid sequence from position 23 to 120 of the amino acid sequence in SEQ ID NO: 51 via a linker sequence (SEQ ID NO: 87); FKBP is connected to the C terminus of an amino acid sequence from position 4 to 22 of the amino acid sequence in SEQ ID NO: 51 via a linker sequence (SEQ ID NO: 87); and an amino acid residue at position 120 of the amino acid sequence in SEQ ID NO: 51 is connected to an amino acid residue at position 4 of the same via a linker sequence (SEQ ID NO: 86).

The fusion protein was expressed by *Escherichia coli*, and purified, followed by measurement of emission values in the same manner as in Experiment 12. Rapamycin was added in concentrations of 0 nM, 12.5 nM, 25 nM, 50 nM, and 100 nM.

Figure 34:
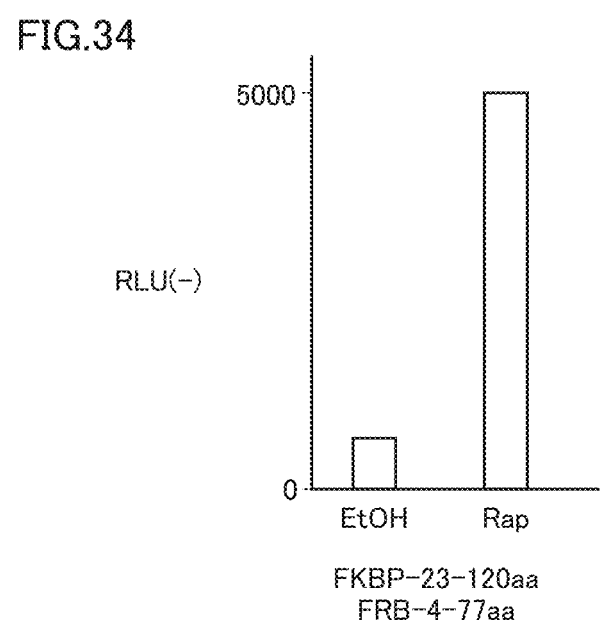

As shown in FIG. 34, an increase of emission values in a rapamycin-concentration-dependent manner was detected. It was found that the fusion protein of the first polypeptide, the second polypeptide, and the target molecules connected together was suitably usable for detecting the target molecule interactions or an interaction-inducing molecule.

[Aspects]

As will be appreciated by those skilled in the art, the above-described example embodiments and Examples are specific examples of the below aspects.

(Item 1)

A reagent kit comprising:

a first polypeptide including a part in any one of amino acid sequences (A) to (C); and a second polypeptide including a part in any one of amino acid sequences (A) to (C), which are consistent of different sequences from a sequence of the first polypeptide, and exhibiting luciferase activity when in close proximity to the first polypeptide;

(A) an amino acid sequence in SEQ ID NO: 1 with deletion of an amino acid sequence from position 1 to 69 and an amino acid sequence from position 204 to 221, (B) an amino acid sequence in SEQ ID NO: 1 with deletion of an amino acid sequence from position 1 to 69 and deletion or substitution of at least one of amino acid residues at positions 146 to 156, (C) the amino acid sequence (A) or (B) with further deletion of at least one of amino acid residues at positions 70 to 74.

The reagent kit according to Item 1 can be used as a probe for detecting intermolecular interactions. Each polypeptide in the reagent kit according to Item 1 is small, and therefore less likely to inhibit the expression and function of target molecules that are to be investigated their interactions.

(Item 2)

In the reagent kit according to Item 1, any one of the amino acid sequences (A) to (C) is any one of amino acid sequences (a) to (c):

(a) an amino acid sequence in any one of SEQ ID NOs: 51 to 56;

(b) an amino acid sequence having at least 85% homology with an amino acid sequence in any one of SEQ ID NOs: 51 to 56; or (c) an amino acid sequence in any one of SEQ ID NOs: 51 to 56 with deletion, substitution, insertion, or addition of one or several amino acid residues.

The reagent kit according to Item 2 makes it possible to obtain a probe capable of exhibiting a high emission activity.

(Item 3)

In the reagent kit according to Item 1 or Item 2, at least one of the first polypeptide and the second polypeptide has, in amino acid sequences in SEQ ID NOs: 51 to 53, an amino acid sequence corresponding to one selected from amino acid sequences from position 4 to 20, from position 4 to 21, from position 4 to 22, from position 4 to 23, from position 4 to 24, from position 4 to 33, from position 4 to 34, from position 4 to 35, from position 4 to 36, from position 4 to 37, from position 4 to 45, from position 4 to 46, from position 4 to 47, from position 4 to 48, from position 4 to 49, from position 4 to 56, from position 4 to 57, from position 4 to 58, from position 4 to 59, from position 4 to 60, from position 4 to 62, from position 4 to 63, from position 4 to 64, from position 4 to 65, from position 4 to 66, from position 4 to 67, from position 4 to 70, from position 4 to 71, from position 4 to 72, from position 4 to 73, from position 4 to 74, from position 4 to 75, from position 4 to 76, from position 4 to 77, from position 4 to 78, from position 4 to 79, from position 4 to 88, from position 4 to 89, from position 4 to 90, from position 4 to 91, from position 4 to 92, from position 4 to 101, from position 4 to 102, from position 4 to 103, from position 4 to 104, from position 4 to 105, from position 21 to 120, from position 22 to 120, from position 23 to 120, from position 24 to 120, from position 25 to 120, from position 34 to 120, from position 35 to 120, from position 36 to 120, from position 37 to 120, from position 38 to 120, from position 46 to 120, from position 47 to 120, from position 48 to 120, from position 49 to 120, from position 50 to 120, from position 57 to 120, from position 58 to 120, from position 59 to 120, from position 60 to 120, from position 61 to 120, from position 63 to 120, from position 64 to 120, from position 65 to 120, from position 66 to 120, from position 67 to 120, from position 68 to 120, from position 69 to 120, from position 70 to 120, from position 71 to 120, from position 72 to 120, from position 73 to 120, from position 74 to 120, from position 75 to 120, from position 76 to 120, from position 77 to 120, from position 78 to 120, from position 79 to 120, from position 80 to 120, from position 89 to 120, from position 90 to 120, from position 91 to 120, from position 92 to 120, from position 93 to 120, from position 102 to 120, from position 103 to 120, from position 104 to 120, from position 105 to 120, and from position 106 to 120 of the amino acid sequence in SEQ ID NO: 51.

The reagent kit according to Item 3 makes it possible to obtain a probe capable of exhibiting a high emission activity.

(Item 4)

In the reagent kit according to any one of Item 1 to Item 3, at least one of the first polypeptide and the second polypeptide has any one of amino acid sequences (1) to (3):

(1) an amino acid sequence in any one of SEQ ID NOs: 76 to 85;

(2) an amino acid sequence having at least 85% homology with an amino acid sequence in any one of SEQ ID NOs: 76 to 85; or (3) an amino acid sequence in any one of SEQ ID NOs: 76 to 85 with deletion, substitution, insertion, or addition of one or several amino acid residues.

The reagent kit according to Item 4 makes it possible to obtain a probe capable of exhibiting a high emission activity.

(Item 5)

In the reagent kit according to any one of Item 1 to Item 4, an amino acid sequence constituting the first polypeptide partially overlaps with an amino acid sequence constituting the second polypeptide.

The reagent kit according to Item 5 makes it possible to obtain a smaller probe capable of exhibiting a high emission activity.

(Item 6)

In the reagent kit according to any one of Item 1 to Item 4, an amino acid sequence constituting the first polypeptide does not overlap with an amino acid sequence constituting the second polypeptide.

The polypeptide according to Item 6 makes it possible to obtain a smaller probe capable of exhibiting a higher emission activity.

(Item 7)

In the reagent kit according to any one of Item 1 to Item 6, the first polypeptide and the second polypeptide are connected to each other via a linker sequence.

The reagent kit according to Item 7 makes it easy to detect a luminescence signal.

(Item 8)

In the reagent kit according to any one of Item 1 to Item 7, the first polypeptide is connected to a first target protein, and the second polypeptide is connected to a second target protein.

The reagent kit according to Item 8 is usable for detecting interactions between the first target protein and the second target protein.

(Item 9)

A first polypeptide including a part in any one of amino acid sequences (A) to (C), wherein the first polypeptide:

exhibits luciferase activity when in close proximity to a second polypeptide including a part in any one of amino acid sequences (A) to (C); and has a sequence different from the second polypeptide;

(A) an amino acid sequence in SEQ ID NO: 1 with deletion of an amino acid sequence from position 1 to 69 and an amino acid sequence from position 204 to 221, (B) an amino acid sequence in SEQ ID NO: 1 with deletion of an amino acid sequence from position 1 to 69 and deletion or substitution of at least one of amino acid residues at positions 146 to 156, (C) the amino acid sequence (A) or (B) with further deletion of at least one of amino acid residues at positions 70 to 74.

The polypeptide according to Item 9 is usable as a probe for detecting intermolecular interactions. The polypeptide according to Item 9 is small, and therefore less likely to inhibit the expression and function of target molecules that are to be investigated their interactions.

(Item 10)

A fusion protein comprising the first polypeptide according to any one of Item 1 to Item 9 and a first target protein.

The fusion protein according to Item 10 is usable for detecting interactions between the first target protein and other molecules.

(Item 11)

A nucleic acid coding for the first polypeptide according to any one of Item 1 to Item 9 or for the fusion protein according to Item 10.

The nucleic acid according to Item 11 makes it possible to produce the first polypeptide according to Item 1 to Item 9 or the fusion protein according to Item 10.

(Item 12)

A vector comprising the nucleic acid according to Item 11.

The vector according to Item 12 makes it possible to easily amplify and retain the nucleic acid according to Item 11. Moreover, by using the vector according to Item 12, it is possible to produce the first polypeptide according to Item 1 to Item 9 or the fusion protein according to Item 10.

(Item 13)

A transformed cell into which the nucleic acid according to Item 11 is introduced.

The transformed cell according to Item 13 is capable of expressing the first polypeptide according to Item 1 to Item 9 or the fusion protein according to Item 10.

(Item 14)

A protein interaction analysis method that uses the reagent kit according to Item 1 to Item 8.

The protein interaction analysis method according to Item 14 makes it possible to detect interactions between two proteins by way of luminescence. The polypeptide used in this method has a small molecular weight, and therefore its fusion protein with the target protein is likely to be expressed in a normal fashion. Moreover, the polypeptide used in this method is less likely to inhibit the function of the target protein.

Although the present invention has been described and illustrated in detail, it is clearly understood that the same is by way of illustration and example only and is not to be taken by way of limitation, the scope of the present invention being interpreted by the terms of the appended claims.

---

What is claimed is:

1. A reagent kit comprising:

a combination of a first polypeptide and a second polypeptide selected from (A), (B), (C) or (D):

(A) wherein the first polypeptide consists of an amino acid sequence selected from the group consisting of the amino acid sequence of positions 4 to 22, positions 4 to 23, positions 4 to 24, positions 4 to 33, positions 4 to 34, positions 4 to 35, positions 4 to 36, positions 4 to 37, positions 4 to 45, positions 4 to 46, positions 4 to 47, positions 4 to 48, positions 4 to 49, positions 4 to 56, positions 4 to 57, positions 4 to 58, positions 4 to 59, positions 4 to 60, positions 4 to 62, positions 4 to 63, positions 4 to 64, positions 4 to 65, positions 4 to 66, positions 4 to 67, positions 4 to 70, positions 4 to 71, positions 4 to 72, positions 4 to 73, positions 4 to 74, positions 4 to 75, positions 4 to 76, positions 4 to 77, positions 4 to 78, positions 4 to 79, positions 4 to 88, positions 4 to 89, and positions 4 to 90 of SEQ ID NO:51 and wherein the second polypeptide consists of the amino acid sequence of positions 23 to 120 of SEQ ID NO:51;

(B) wherein the first polypeptide consists of an amino acid sequence selected from the group consisting of the amino acid sequence of positions 4 to 77, positions 4 to 78, positions 4 to 79, positions 4 to 88, positions 4 to 89, and positions 4 to 90 of SEQ ID NO:51 and wherein the second polypeptide consists of an amino acid sequence selected from the group consisting of the amino acid sequence of positions 48 to 120, positions 49 to 120, positions 50 to 120, positions 57 to 120, positions 58 to 120, positions 59 to 120, positions 60 to 120, positions 61 to 120, positions 63 to 120, positions 64 to 120, positions 65 to 120, positions 66 to 120, positions 67 to 120, positions 68 to 120, positions 69 to 120, positions 70 to 120, positions 71 to 120, positions 72 to 120, positions 73 to 120, positions 74 to 120, positions 75 to 120, positions 76 to 120, positions 77 to 120, and positions 78 to 120 of SEQ ID NO:51;

(C) wherein the first polypeptide consists of the amino acid sequence of positions 4 to 64 of SEQ ID NO:51 and wherein the second polypeptide consists of an amino acid sequence selected from the group consisting of the amino acid sequence of positions 65 to 120, positions 66 to 120, positions 67 to 120, positions 68 to 120, positions 69 to 120, positions 70 to 120, positions 71 to 120, positions 72 to 120, and positions 73 to 120 of SEQ ID NO:51; or (D) wherein the first polypeptide consists of the amino acid sequence of positions 4 to 72 of SEQ ID NO:51 and wherein the second polypeptide consists of an amino acid sequence selected from the group consisting of the amino acid sequence of positions 23 to 120, positions 73 to 120, and positions 104 to 120 of SEQ ID NO:51;

wherein the combination exhibits luciferase activity when a solution containing the first polypeptide is mixed with a solution containing the second polypeptide.

2. The reagent kit according to claim 1, wherein an amino acid sequence constituting the first polypeptide does not overlap with an amino acid sequence constituting the second polypeptide.

3. The reagent kit according to claim 1, wherein the first polypeptide and the second polypeptide are connected to each other via a linker sequence.

4. The reagent kit according to claim 1, wherein the first polypeptide is connected to a first target protein, and the second polypeptide is connected to a second target protein.

\* \* \* \* \*